(12) United States Patent
Cascao-Pereira et al.

(10) Patent No.: US 8,999,692 B2
(45) Date of Patent: Apr. 7, 2015

(54) COMPOSITIONS AND METHODS COMPRISING CELLULASE VARIANTS WITH REDUCED AFFINITY TO NON-CELLULOSIC MATERIALS

(75) Inventors: Luis G. Cascao-Pereira, Redwood City, CA (US); Thijs Kaper, Half Moon Bay, CA (US); Bradley R. Kelemen, Menlo Park, CA (US); Amy D. Liu, Sunnyvale, CA (US)

(73) Assignee: Danisco US Inc., Palo Alto, CA (US)

( * ) Notice: Subject to any disclaimer, the term of this patent is extended or adjusted under 35 U.S.C. 154(b) by 249 days.

(21) Appl. No.: 13/543,627

(22) Filed: Jul. 6, 2012

(65) Prior Publication Data

US 2012/0276595 A1 Nov. 1, 2012

Related U.S. Application Data

(62) Division of application No. 12/477,887, filed on Jun. 3, 2009, now Pat. No. 8,236,542.

(60) Provisional application No. 61/059,506, filed on Jun. 6, 2008.

(51) Int. Cl.
*C12N 9/42* (2006.01)
(52) U.S. Cl.
CPC ....... *C12N 9/2437* (2013.01); *C12Y 302/01091* (2013.01); *Y02E 50/17* (2013.01)
(58) Field of Classification Search
CPC ..................... C12Y 302/01091; C12N 9/2437; Y02E 50/17
USPC ................................................ 435/161, 195
See application file for complete search history.

(56) References Cited

U.S. PATENT DOCUMENTS

| 5,246,853 | A | 9/1993 | Clarkson et al. |
| 5,475,101 | A | 12/1995 | Ward et al. |
| 6,162,782 | A | 12/2000 | Clarkson et al. |
| 2006/0205042 | A1 | 9/2006 | Aehle et al. |

FOREIGN PATENT DOCUMENTS

| EP | 1726644 A1 | 11/2006 |
| EP | 1350843 B1 | 3/2007 |
| WO | WO 2004/056981 | 7/2004 |
| WO | WO 2006/074005 A2 | 7/2006 |
| WO | WO 2008/025164 A1 | 3/2008 |
| WO | WO 2008/153925 A2 | 12/2008 |

OTHER PUBLICATIONS

Sequence alignment between Accession No. S70602 and Applicants' SEQ ID No. 3 (2004).*
Altschul, S.F., et al., "Basic Local Alignment Search Tool." *J. Mol. Biol.* 215:403-410, 1990.
Baker, J.O., et al., "Hydrolysis of Cellulose Using Ternary Mixtures of Purified Cellulases." *Appl. Biochem. Biotechnol.* 70-72: 395-403, 1998.
Berges, T., et al., "Isolation of uridine auxotrophs from *Trichoderma reesei* and efficient transformation with the cloned ura3 and ura5 genes." *Curr. Genet.* 19:359-365, 1991.
Filho, E.X.F., "Purification and characterization of a β-glucosidase from solid-state cultures of *humicola* grisea var. thermoidea." *Can. .., Microbiol.* 42:1-5, 1996.
Goedegebuur, F., et al., "Cloning and relational analysis of 15 novel fungal endoglucanases from family 12 glycosyl hydrolases." *Curr. Genet* 41: 89-98, 2002.
Himmel, M.E., et al. In *Fuels and Chemicals from Biomass*, Chapter 1, "Advanced Dioethanol Production Technologies: A Perspective." ACS Symposium Series 666, eds. B. C. Saha and J. Woodward, pp. 2-45, 1997.
Knowles, J., et al., "Cellulase families and their genes." TIBTECH 5: 255-261, 1987.
Linder, M., et al., "The roles and function of cellulose-binding domains." *J. Biotechnol.* 57:15-28, 1997.
Nevalainen, H., et al., In *The Mycota: II Genetics and Biotechnology*, Chapter 18, "Molecular Biology of Cellulolytic Fungi." Eds. U. Kück, et al., Springer-Verlag, pp. 303-319, 1995.
Schell, D.J., et al., "Dilute-Sulfuric Acid Pretreatment of Corn Stover in Pilot-Scale Reactor." *J. Appl. Biochem. Biotechnol.* 105:69-86, 2003.
Sheir-Neiss, G., et al., "Characterization of the secreted cellulases of *Trichoderma reesei* wild type and mutants during controlled fermentations." *Appl. Microbiol. Biotechnology* 20: 46-53, 1984.
Shoemaker, S. et al., "Molecular Cloning Of ExoOCellobiohydrolase I Derived From *Trichoderma Reesei* Strain L27." *Bio/Technology* 1:691-696, 1983.
Sparks, D.L., et al., "Quantitative measurement of lipoprotein surface charge by agarose gel electrophoresis." *Journal of Lipid Research* 33:123-130, 1992.
Teeri, T., et al., "Homologous domains in *Trichoderma reesei* cellulolytic enzymes: gene sequence and expression of cellobiohydrolase II." *Gene* 51:43-52, 1987.
Tomme, P., et al., "Studies of the cellulolytic system of *Trichoderma reesei* QM 9414: Analysis of domain function in two cellobiohydrolases by limited proteolysis" *Eur. J. Biochem.* 170: 575-581, 1988.
Tormo J., et al., "Crystal structure of a bacterial family-III cellulose-binding domain: a general mechanism for attachment to cellulose." *EMBO J.* 15(21): 5739-5751, 1996.
Van Tilbeurgh, H., et al., "Limited proteolysis of the cellobiohydrolase I from *Trichoderma reesei.*" *FEBS Lett.* 204(2): 223-227, 1986.

(Continued)

*Primary Examiner* — Tekchand Saidha
(74) *Attorney, Agent, or Firm* — Danisco US Inc.

(57) ABSTRACT

The present disclosure relates to cellulase variants. In particular the present disclosure relates to cellulase variants having reduced binding to non-cellulosic materials. Also described are nucleic acids encoding the cellulase, compositions comprising said cellulase, methods of identifying cellulose variants and methods of using the compositions.

14 Claims, 6 Drawing Sheets

(56) References Cited

OTHER PUBLICATIONS

Zou, J.-Y., et al., "Crystallographic evidence for substrate ring distortion and protein conformational changes during catalysis in cellobiohydrolase." *Structure* 7(9): 1035-1045, 1999.
International Search Report and Written Opinion of International Application No. PCT/US2009/046159, dated Feb. 19, 2010.

Murray P.G., et al, "Molecular cloning, transcriptional, and expression analysis of the first cellulase gene (cbh2), encoding cellobiohydrolase II, from the moderately thermophilic fungus *Talaromyces emersonii* and structure prediction of the gene product," 301 (2), 280-286. 2003.

* cited by examiner

```
T. reesei CBH #3           ------------------------------QACSSVWGQCGGQN----W
H. koningii CBH #4         ------------------------------QACSSVWGQCGGQN----W
H. insolens CBH #5         ----------------------APVVEERQNCAPTWGQCGGIG----F
A. cellulolyticus CBH #6   -------------MLRYLSIVAATAILTGVEAQQSVWGQCGGQG----W
A. bisporus CBH #7         ---------------------QSPV-----------WGQCGGNG----W
F. oxysporum EG #8         ----------------------APVEERQSCSNGVWAQCGGQN----W
P. chrysosporium CBH #9    ----------MKSTAFFAALVTLLPAYVAGQASE--WGCGGIG----W
T. emersonii CBH #10       --------------MRNLLALAPAALLVGAAEAQQSLWGQCGGSS----W
T. fusc CBH #11            -AGCSVDYTVN-SWGTGFTANVTITNLGSAINGWTLEWDFPGNQQVTNLW
T. fusc EG #12             ----------------------NDSPFYVNPNMSSAEWVRNNPND-----
C. fimi EG #13             APGCRVDYAVTNQWPGGFGANVTITNLGDPVSSWKLDWTYTAGQRIQQLW
                                                              *

T. reesei CBH #3           SGPTCCASGSTCVYSNDYYSQCLP--GA---ASSSSSTRAAST----TSR
H. koningii CBH #4         SGPTCCASGSTCVYSNDYYSQCLP--GA--------ASSSSSTRASSTTA
H. insolens CBH #5         NGPTCCQSGSTCVKQNDWYSQCLP--GSQVTTSTTSTSSSST----TSR
A. cellulolyticus CBH #6   SGATSCAAGSTCSTLNPYYAQCIP--GT--------ATSTTLV----KTT
A. bisporus CBH #7         TGPTTCASGSTCVKQNDFYSQCLP--NN-------------------Q
F. oxysporum EG #8         SGTPCCTSGNKCVKLNDFYSQCQP--GS----------AEPS----STA
P. chrysosporium CBH #9    TGPTTCVSGTTCTVLNPYYSQCLP--GS-AVTTTSVITSHSSS----VSS
T. emersonii CBH #10       TGATSCAAGATCSTINPYYAQCVP--AT--------ATPTTLT----TTT
T. fusc CBH #11            NGTYTQSGQHVSVSNAPYNASI-PANGTVEFGFNGSYSGSNDIPSSFKLN
T. fusc EG #12             PRTPVIRDRIASVPQGTWFAHHNP--GQ--------ITGQVDA----LMS
C. fimi EG #13             NGTASTNGGQVSVTSLPWNGSI-PTGGTASFGFNGSWAGSNPTPASFSLN
                                .       .    : .   *

T. reesei CBH #3           VSPTTSR---SSSATPPFGSTTTRVPP-VGSGTATYSGNPFVGVTPWANA
H. koningii CBH #4         RASSTTS---RSSATPPPGSSTTRVPP-VGSGTATYSGNPFVGVTPWANA
H. insolens CBH #5         ATSTTRT---GGVTSITTAPTRTVTIPGGATTTASYNGNPFEGVQLWANN
A. cellulolyticus CBH #6   SSTSVGT--------TSPPTTTTTKAST-TATTTAAASGNPFSGYQLYANP
A. bisporus CBH #7         APPSTTT---QPGTTPPATTTSGGTGP-TSGA------GNPYTGKTVWLSP
F. oxysporum EG #8         AGPSTT----ATKTTATGGSSTTAGGS-VTSAPPAASDNPYAGVDLWANN
P. chrysosporium CBH #9    VSSHSGS---STSTSSPTGPTGTNPPP-PPSA-----NNPWTGFQIFLSP
T. emersonii CBH #10       KPTSTGG---AAPTTPPPTTTGTTTSP-VVTRPASASGNPFEGYQLYANP
T. fusc CBH #11            GVTCDGSDDPDPEPSPSFSPSPSPTDPDEPGGPTNPPTNPGEKVD---NP
T. fusc EG #12             AAQAAGK---IPILVVYNAPGRDCGNH-SSGGAPSHS-----AYRSWIDE
C. fimi EG #13             GTTCTGT---VPTTSPTPTPTTPTP-TPTPTPTPT--PTVTPQPTSGF
                                                           .

T. reesei CBH #3           YYASEVSSLAIPSLTG-AMATAAAAVAKVPSFMWLDTL-----DKTP-LM
H. koningii CBH #4         YYASEVSSLAIPSLTG-AMATAAAAVAKVPSSMWLDTF-----DKTP-LM
H. insolens CBH #5         YYRSEVHTLAIPQITDPALRAAASAVAEVPSFQWLDRN-----VTVDTLL
A. cellulolyticus CBH #6   YYSSEVHTLAIPSLTG-SLAAAATKAAEIPSFVWLDTA-----AKVP-TM
A. bisporus CBH #7         FYADEVAQ-AAADISNPSLATKAASVAKIPTFVWFDTV-----AKVP-DL
F. oxysporum EG #8         YYRSEVMNLAVPKLSG-AKATAAAKVADVPSFQWMDTY-----DHIS-LM
P. chrysosporium CBH #9    YYANEVAA-AAKQITDPTLSSKAASVANIPTFTWLDSV-----AKIP-DL
T. emersonii CBH #10       YYASEVISLAIPSLSS-ELVPKASEVAKVPSFVWLDQA-----AKVP-SM
T. fusc CBH #11            FEGAKLYVNPVWSAKA-AAEPGGSAVANESTAVWLDRIGAIEGNDSPTTG
T. fusc EG #12             F-AAGLKNRPAYIIVEPDLISLMSSCMQHVQQEVLETM-----AYAGKAL
C. fimi EG #13             YVDPTTQGYRAWQAASGTDKALLEKIALTPQAYWVGNW-----ADAS---
                                :
```

*FIG. 3A*

```
T. reesei CBH #3            EQTLAD-IRTANKNGGN--YAGQFVVYDLPDRDCAALASNGEYSIADGGV
H. koningii CBH #4          EQTLAD-IRTANKNGGN--YAGQFVVYDLPDRDCAALASNGEYSIADGGV
H. insolens CBH #5          VETLSE-IRAANQAGANPPYAAQIVVYDLPDRDCAAAASNGEWAIANNGA
A. cellulolyticus CBH #6    GTYLAN-IEAANKAGASPPIAGIFVVYDLPDRDCAAAASNGEYTVANNGV
A. bisporus CBH #7          GGYLAD-ARSKNQ-------LVQIVVYDLPDRDCAALASNGEFSLANDGL
F. oxysporum EG #8          EDTLAD-IRKANKAGGK--YAGQFVVYDLPNRDCAAAASNGEYSLDKDGA
P. chrysosporium CBH #9     GTYLAS--ASALGKSTGTKQLVQIVIYDLPDRDCAAKASNGEFSIANNGQ
T. emersonii CBH #10        GDYLKD-IQSQNAAGADPPIAGIFVVYDLPDRDCAAAASNGEFSIANNGV
T. fusc CBH #11             SMGLRDHLEEAVRQSGGDPLTIQVVIYNLPGRDCAALASNGELGP--DEL
T. fusc EG #12              KAGSSQ-ARIYFDAGHSAWHSPAQMASWL----QQADISNSAHGIA-TNT
C. fimi EG #13              -HAQAE-VADYTGRAVAAGKTPMLVVYAIPGRDCGSHSGGG------VSE
                                         :       :         :    ...

T. reesei CBH #3            AKYKN-YIDTIRQIVVEYSD---IRTLLVIEPDSLANLVTNLGTPK----
H. koningii CBH #4          DKYKN-YIDTIRQIVVEYSD---IRTLLVIEPDSLANLVTNLGTPK----
H. insolens CBH #5          NNYKG-YINRIREILISFSD---VRTILVIEPDSLANMVTNMNVAK----
A. cellulolyticus CBH #6    ANYKA-YIDSIVAQLKAYPD---VHTILIIEPDSLANMVTNLSTAK----
A. bisporus CBH #7          NKYKN-YVDQIAAQIKQFPD---VSVVAVIEPDSLANLVTNLNVQK----
F. oxysporum EG #8          NKYKA-YIAKIKGILQNYSD---TKVILVIEPDSLANLVTNLNVDK----
P. chrysosporium CBH #9     ANYEN-YIDQIVAQIQQFPD---VRVVAVIEPDSLANLVTNLNVQK----
T. emersonii CBH #10        ALYKQ-YIDSIREQLTTYSD---VHTILVIEPDSLANVVTNLNVPK----
T. fusc CBH #11             DRYKSEYIDPIADIMWDFADYENLRIVAIIEIDSLPNLVTNVGGNGGTEL
T. fusc EG #12              SNYRW-TADEVA-----YAK---AVLSAIGNPSLRAVIDTSRNGNG----
C. fimi EG #13              SEYAR-WVDTVAQGIK-------GNPIVILEPDALAQLGD----------
                                 *            :           : :  .  .  :

T. reesei CBH #3            CA--NAQSAYLECINYAVTQL-NLPNVAMYLDAGHAGWLGWPANQDPAAQ
H. koningii CBH #4          CA--NAQSAYLECINYAVTQL-NLPNVAMYLDAGHAGWLGWPANQDPAAQ
H. insolens CBH #5          CS--GAASTYRELTIYALKQL-DLPHVAMYMDAGHAGWLGWPANIQPAAE
A. cellulolyticus CBH #6    CA--EAQSAYYECVNYALINL-NLANVAMYIDAGHAGWLGWSANLSPAAQ
A. bisporus CBH #7          CA--NAQSAYKEGVIYAVQKL-NAVGVTMYIDAGHAGWLGWPANLSPAAQ
F. oxysporum EG #8          CA--KAESAYKELTVYAIKEL-NLPNVSMYLDAGHGGWLGWPANIGPAAK
P. chrysosporium CBH #9     CA--NAKTTYLACVNYALTNL-AKVGVYMYMDAGHAGWLGWPANLSPAAQ
T. emersonii CBH #10        CA--NAQDAYLECINYAITQL-DLPNVAMYLDAGHAGWLGWQANLAPAAQ
T. fusc CBH #11             CAYMKQNGGYVNGVGYALRKLGEIPNVYNYIDAAHHGWIGWDSNFGPSVD
T. fusc EG #12              ----PAGNEWCDPSGRAIGTPSTTNTGDPMIDAFL--WIKLPGEADGCIA
C. fimi EG #13              CS---GQGDRVGFLKYAAKSL-TLKGARVYIDAGHAKWLSVDTPVNRLNQ
                                          *              ;**    *;

T. reesei CBH #3            LFANVYKNAS-SPRALRGLATNVANYNGWNIT-------------SPPSY
H. koningii CBH #4          LFANVYKNAS-SPRALRGLATNVANYNGWNIT-------------SPPSY
H. insolens CBH #5          LFAKIYEDAG-KPRAVRGLATNVANYNAWSIS-------------SPPPY
A. cellulolyticus CBH #6    LFATVYKNAS-APASLRGLATNVANYNAWSIS-------------SPPSY
A. bisporus CBH #7          LFAQIYRDAG-SPRNLRGIATNVANFNALRAS-------------SPDPI
F. oxysporum EG #8          LYAQIYKDAG-KPSRVRGLVTNVSNYNGWKLS-------------TKPDY
P. chrysosporium CBH #9     LFTQVWQNAG-KSPFIKGLATNVANYNALQAA-------------SPDPI
T. emersonii CBH #10        LFASVYKNAS-SPASVRGLATNVANYNAWSIS-------------RCPSY
T. fusc CBH #11             IFYEAANASGSTVDYVHGFISNTANYSATVEPYLDVNGTVNGQLIRQSKW
T. fusc EG #12              GAGQFVPAAYEMAIAAGGTNPNPNPNP--TP-------------TPTPT
C. fimi EG #13              V---------GFEYAVGFALNTSNYQT-----------------------
                                  *    . *  .
```

FIG. 3B

| | |
|---|---|
| T. reesei CBH #3 | TQGNAVYNEKLYIHAIGPLLANHGWSN-AFFITDQGRSGK----QPTGQQ |
| H. koningii CBH #4 | TQGNAVYNEQLYIHAIGPLLANHGWSN-AFFITDQGRSGK----QPTGQQ |
| H. insolens CBH #5 | TSPNPNYDEKHYIEAFRPLLEARGFP--AQFIVDQGRSGK----QPTGQK |
| A. cellulolyticus CBH #6 | TSGDSNYDEKLYINALSPLLTSNGWPN-AHFIMDTSRNGV----QPTKQQ |
| A. bisporus CBH #7 | TQGNSNYDEIHYIEALAPMLSNAGFP--AHFIVDQGRSGV-----QNIRD |
| F. oxysporum EG #8 | TESNPNYDEQRYINAFAPLLAQEGWSN-VKFIVDQGRSGK----QPTGQK |
| P. chrysosporium CBH #9 | TQGNPNYDEIHYINALAPLLQQAGWD--ATFIVDQGRSGV-----QNIRQ |
| T. emersonii CBH #10 | TQGDANCDEEDYVNALGPLFQEQGFP--AYFIIDTSRNGV----RPTKQS |
| T. fusc CBH #11 | VDWNQYVDELSFVQDLRQALIAKGFRSDIGMLIDTSRNGWGGPNRPTGPS |
| T. fusc EG #12 | PTPPPGSSGACTATYTIANEWNDGFQATVTVTANQNITGW--------TV |
| C. fimi EG #13 | -----TADSKAYGQQISQRLGG------KKFVIDTSRNGN---------G |
| | .    :..* |

| | |
|---|---|
| T. reesei CBH #3 | QWGD----------------WCNVIGTGFGIRPSANTGDSLLDSFVWV |
| H. koningii CBH #4 | QWGD----------------WCNVIGTGFGIRPSANTGDSLLDSFVWI |
| H. insolens CBH #5 | EWGH----------------WCNAIGTGFGMRPTANTGHQYVDAFVWV |
| A. cellulolyticus CBH #6 | AWGD----------------WCNVIGTGFGVQPTTNTGDPLEDAFVWV |
| A. bisporus CBH #7 | QWGD----------------WCNVKGAGFGQRPTTNTGSSLIDAIVWV |
| F. oxysporum EG #8 | AQGD----------------WCNAKGTGFGLRPSTNTGDALADAFVWV |
| P. chrysosporium CBH #9 | QWGD----------------WCNIKGAGFGTRPTTNTGSQFIDSIVWV |
| T. emersonii CBH #10 | QWGD----------------WCNVIGTGFGVRPTTDTGNPLEDAFVWV |
| T. fusc CBH #11 | SSTDLNTYVDESRIDRRIHPGNWCNQAGAGLGERPTVNPA-PGVDAYVWV |
| T. fusc EG #12 | TWT------------------FTDGQTITNAWNADVSTSGSSVTARNVG |
| C. fimi EG #13 | SNGE----------------WCNPRGRALGERPVAVNDSGLDALLWV |
| | :  :     , ... : |

| | |
|---|---|
| T. reesei CBH #3 | KPGGECDGTSDSS----APRFDSHCA-----------LPDALQPAPQAG |
| H. koningii CBH #4 | KPGGECDGTSDSS----APRFDSHCA-----------LPDALQPAPQAG |
| H. insolens CBH #5 | KPGGECDGTSDTT----AARYDYHCG-----------LEDALKPAPEAG |
| A. cellulolyticus CBH #6 | KPGGESDGTSNSS----ATRYDFHCG-----------YSDALQPAPEAG |
| A. bisporus CBH #7 | KPGGECDGTSDNS----SPRFDSHCS-----------LSDAHQPAPEAG |
| F. oxysporum EG #8 | KPGGESDGTSDTS----AARYDYHCG-----------LDDALKPAPEAG |
| P. chrysosporium CBH #9 | KPGGECDGTSNSS----SPRYDSTCS-----------LPDAAQPAPEAG |
| T. emersonii CBH #10 | KPGGESDGTSNTT----SPRYDYHCG-----------LSDALQPAPEAG |
| T. fusc CBH #11 | KPPGESDGASEEIPNDEGKGFDRMCDPTYQGNARNGNNPSGALPNAPISG |
| T. fusc EG #12 | HNGTLSQGASTEF-------------------------GFVG |
| C. fimi EG #13 | KLPGESDGACNGG-------------------------PAAG |
| | :     .:*:.                              * |

| | |
|---|---|
| T. reesei CBH #3 | AWFQAYFVQLLTNANPSFL |
| H. koningii CBH #4 | AWFQAYFVQLLTNANPSFL |
| H. insolens CBH #5 | QWFQAYFEQLLRNANPPF- |
| A. cellulolyticus CBH #6 | TWFQAYFVQLLTNANPALV |
| A. bisporus CBH #7 | TWFQAYFETLVANANPAL- |
| F. oxysporum EG #8 | TWFQAYFEQLLDNANPSFL |
| P. chrysosporium CBH #9 | TWFQAYFQTLVSAANPPL- |
| T. emersonii CBH #10 | TWFQAYFEQLLTNANPLF- |
| T. fusc CBH #11 | HWFSAQFRELLANAYPPL- |
| T. fusc EG #12 | SKGNSNSVPTLTCAAS--- |
| C. fimi EG #13 | QWWQEIALEMARNARW--- |
| | * |

*FIG. 3C*

SEQUENCE LISTING

<160> NUMBER OF SEQ ID NOS: 16

<210> SEQ ID NO 1
<211> LENGTH: 1416
<212> TYPE: DNA
<213> ORGANISM: Hypocrea jecorina
<220> FEATURE:
<221> NAME/KEY: misc_feature
<223> OTHER INFORMATION: reference Hypocrea jecorina CBH2 coding DNA
      sequence

<400> SEQUENCE: 1

| | | |
|---|---|---|
| atgattgtcg gcattctcac cacgctggct acgctggcca cactcgcagc tagtgtgcct | 60 |
| ctagaggagc ggcaagcttg ctcaagcgtc tggggccaat gtggtggcca gaattggtcg | 120 |
| ggtccgactt gctgtgcttc cggaagcaca tgcgtctact ccaacgacta ttactcccag | 180 |
| tgtcttcccg cgctgcaag ctcaagctcg tccacgcgcg ccgcgtcgac gacttctcga | 240 |
| gtatccccca caacatcccg gtcgagctcc gcgacgcctc cacctggttc tactactacc | 300 |
| agagtaccct cagtcggatc gggaaccgct acgtattcag caacccttt tgttggggtc | 360 |
| actccttggg ccaatgcata ttacgcctct gaagttagca gcctcgctat tcctagcttg | 420 |
| actggagcca tggccactgc tgcagcagct gtcgcaaagg ttccctcttt tatgtggcta | 480 |
| gatactcttg acaagacccc tctcatggag caaaccttgg ccgacatccg caccgccaac | 540 |
| aagaatggcg gtaactatgc cggacagttt gtggtgtatg acttgccgga tcgcgattgc | 600 |
| gctgcccttg cctcgaatgg cgaatactct attgccgatg gtggcgtcgc caaatataag | 660 |
| aactatatcg acaccattcg tcaaattgtc gtggaatatt ccgatatccg gaccctcctg | 720 |
| gttattgagc ctgactctct tgccaacctg gtgaccaacc tcggtactcc aaagtgtgcc | 780 |
| aatgctcagt cagcctacct tgagtgcatc aactacgccg tcacacagct gaaccttcca | 840 |
| aatgttgcga tgtatttgga cgctggccat gcaggatggc ttggctggcc ggcaaaccaa | 900 |
| gacccggccg ctcagctatt tgcaaatgtt tacaagaatg catcgtctcc gagagctctt | 960 |
| cgcggattgg caaccaatgt cgccaactac aacgggtgga acattaccag ccccccatcg | 1020 |
| tacacgcaag gcaacgctgt ctacaacgag aagctgtaca tccacgctat ggacctcttt | 1080 |
| cttgccaatc acggctggtc aacgccttc ttcatcactg atcaaggtcg atcgggaaag | 1140 |
| cagcctaccg gacagcaaca gtggggagac tggtgcaatg tgatcggcac cggatttggt | 1200 |
| attcgcccat ccgcaaacac tgggactcg ttgctggatt cgtttgtctg ggtcaagcca | 1260 |
| ggcggcgagt gtgacggcac cagcgacagc agtgcgccac gatttgactc ccactgtgcg | 1320 |
| ctcccagatg ccttgcaacc ggcgcctcaa gctggtgctt ggttccaagc ctactttgtg | 1380 |
| cagcttctca aaacgcaaa cccatcgttc ctgtaa | 1416 |

<210> SEQ ID NO 2
<211> LENGTH: 471
<212> TYPE: PRT
<213> ORGANISM: Hypocrea jecorina
<220> FEATURE:
<221> NAME/KEY: misc_feature
<223> OTHER INFORMATION: Hypocrea jecorina CBH2 full length protein
      sequence

<400> SEQUENCE: 2

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

```
Gln Cys Gly Gly Gln Asn Trp Ser Gly Pro Thr Cys Ala Ser Gly
         35                  40                  45

Ser Thr Cys Val Tyr Ser Asn Asp Tyr Tyr Ser Gln Cys Leu Pro Gly
 50                  55                  60

Ala Ala Ser Ser Ser Ser Thr Arg Ala Ala Ser Thr Thr Ser Arg
 65                  70                  75                  80

Val Ser Pro Thr Thr Ser Arg Ser Ser Ser Ala Thr Pro Pro Gly
                 85                  90                  95

Ser Thr Thr Thr Arg Val Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Asn Tyr Ala Gly Gln Phe Val Val
                180                 185                 190

Tyr Asp Leu Pro Asp Arg Asp Cys Ala Ala Leu Ala Ser Asn Gly Glu
    195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
    275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
    355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
    435                 440                 445
```

```
Pro Gln Ala Gly Ala Trp Phe Gln Ala Tyr Phe Val Gln Leu Leu Thr
            450                 455                 460

Asn Ala Asn Pro Ser Phe Leu
465                 470

<210> SEQ ID NO 3
<211> LENGTH: 447
<212> TYPE: PRT
<213> ORGANISM: Hypocrea jecorina
<220> FEATURE:
<221> NAME/KEY: misc_feature
<223> OTHER INFORMATION: Hypocrea jecorina CBH2 mature protein sequence

<400> SEQUENCE: 3

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335
```

-continued

```
Leu Ala Asn His Gly Trp Ser Asn Ala Phe Phe Ile Thr Asp Gln Gly
                340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445
```

<210> SEQ ID NO 4
<211> LENGTH: 446
<212> TYPE: PRT
<213> ORGANISM: H. koningii

<400> SEQUENCE: 4

```
Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ser Ser Thr Thr Ala Arg Ala Ser Ser Thr Thr Ser Arg Ser
    50                  55                  60

Ser Ala Thr Pro Pro Pro Gly Ser Ser Thr Thr Arg Val Pro Pro Val
65                  70                  75                  80

Gly Ser Gly Thr Ala Thr Tyr Ser Gly Asn Pro Phe Val Gly Val Thr
                85                  90                  95

Pro Trp Ala Asn Ala Tyr Tyr Ala Ser Glu Val Ser Ser Leu Ala Ile
            100                 105                 110

Pro Ser Leu Thr Gly Ala Met Ala Thr Ala Ala Ala Val Ala Lys
        115                 120                 125

Val Pro Ser Ser Met Trp Leu Asp Thr Phe Asp Lys Thr Pro Leu Met
    130                 135                 140

Glu Gln Thr Leu Ala Asp Ile Arg Thr Ala Asn Lys Asn Gly Gly Asn
145                 150                 155                 160

Tyr Ala Gly Gln Phe Val Val Tyr Asp Leu Pro Asp Arg Asp Cys Ala
                165                 170                 175

Ala Leu Ala Ser Asn Gly Glu Tyr Ser Ile Ala Asp Gly Gly Val Asp
            180                 185                 190

Lys Tyr Lys Asn Tyr Ile Asp Thr Ile Arg Gln Ile Val Val Glu Tyr
        195                 200                 205

Ser Asp Ile Arg Thr Leu Leu Val Ile Glu Pro Asp Ser Leu Ala Asn
    210                 215                 220

Leu Val Thr Asn Leu Gly Thr Pro Lys Cys Ala Asn Ala Gln Ser Ala
225                 230                 235                 240

Tyr Leu Glu Cys Ile Asn Tyr Ala Val Thr Gln Leu Asn Leu Pro Asn
                245                 250                 255

Val Ala Met Tyr Leu Asp Ala Gly His Ala Gly Trp Leu Gly Trp Pro
```

```
                    260                 265                 270
Ala Asn Gln Asp Pro Ala Ala Gln Leu Phe Ala Asn Val Tyr Lys Asn
                275                 280                 285

Ala Ser Ser Pro Arg Ala Leu Arg Gly Leu Ala Thr Asn Val Ala Asn
            290                 295                 300

Tyr Asn Gly Trp Asn Ile Thr Ser Pro Pro Ser Tyr Thr Gln Gly Asn
305                 310                 315                 320

Ala Val Tyr Asn Glu Gln Leu Tyr Ile His Ala Ile Gly Pro Leu Leu
                325                 330                 335

Ala Asn His Gly Trp Ser Asn Ala Phe Phe Ile Thr Asp Gln Gly Arg
            340                 345                 350

Ser Gly Lys Gln Pro Thr Gly Gln Gln Gln Trp Gly Asp Trp Cys Asn
                355                 360                 365

Val Ile Gly Thr Gly Phe Gly Ile Arg Pro Ser Ala Asn Thr Gly Asp
            370                 375                 380

Ser Leu Leu Asp Ser Phe Val Trp Ile Lys Pro Gly Gly Glu Cys Asp
385                 390                 395                 400

Gly Thr Ser Asp Ser Ser Ala Pro Arg Phe Asp Ser His Cys Ala Leu
                405                 410                 415

Pro Asp Ala Leu Gln Pro Ala Pro Gln Ala Gly Ala Trp Phe Gln Ala
            420                 425                 430

Tyr Phe Val Gln Leu Leu Thr Asn Ala Asn Pro Ser Phe Leu
                435                 440                 445

<210> SEQ ID NO 5
<211> LENGTH: 460
<212> TYPE: PRT
<213> ORGANISM: H. insolens

<400> SEQUENCE: 5

Ala Pro Val Val Glu Glu Arg Gln Asn Cys Ala Pro Thr Trp Gly Gln
1               5                   10                  15

Cys Gly Gly Ile Gly Phe Asn Gly Pro Thr Cys Cys Gln Ser Gly Ser
                20                  25                  30

Thr Cys Val Lys Gln Asn Asp Trp Tyr Ser Gln Cys Leu Pro Gly Ser
            35                  40                  45

Gln Val Thr Thr Thr Ser Thr Thr Ser Thr Ser Ser Ser Ser Thr Thr
        50                  55                  60

Ser Arg Ala Thr Ser Thr Thr Arg Thr Gly Gly Val Thr Ser Ile Thr
65                  70                  75                  80

Thr Ala Pro Thr Arg Thr Val Thr Ile Pro Gly Gly Ala Thr Thr Thr
                85                  90                  95

Ala Ser Tyr Asn Gly Asn Pro Phe Glu Gly Val Gln Leu Trp Ala Asn
                100                 105                 110

Asn Tyr Tyr Arg Ser Glu Val His Thr Leu Ala Ile Pro Gln Ile Thr
            115                 120                 125

Asp Pro Ala Leu Arg Ala Ala Ala Ser Ala Val Ala Glu Val Pro Ser
        130                 135                 140

Phe Gln Trp Leu Asp Arg Asn Val Thr Val Asp Thr Leu Leu Val Glu
145                 150                 155                 160

Thr Leu Ser Glu Ile Arg Ala Ala Asn Gln Ala Gly Ala Asn Pro Pro
                165                 170                 175

Tyr Ala Ala Gln Ile Val Val Tyr Asp Leu Pro Asp Arg Asp Cys Ala
            180                 185                 190
```

```
Ala Ala Ala Ser Asn Gly Glu Trp Ala Ile Ala Asn Gly Ala Asn
            195                 200                 205

Asn Tyr Lys Gly Tyr Ile Asn Arg Ile Arg Glu Ile Leu Ile Ser Phe
        210                 215                 220

Ser Asp Val Arg Thr Ile Leu Val Ile Glu Pro Asp Ser Leu Ala Asn
225                 230                 235                 240

Met Val Thr Asn Met Asn Val Ala Lys Cys Ser Gly Ala Ala Ser Thr
                245                 250                 255

Tyr Arg Glu Leu Thr Ile Tyr Ala Leu Lys Gln Leu Asp Leu Pro His
            260                 265                 270

Val Ala Met Tyr Met Asp Ala Gly His Ala Gly Trp Leu Gly Trp Pro
        275                 280                 285

Ala Asn Ile Gln Pro Ala Ala Glu Leu Phe Ala Lys Ile Tyr Glu Asp
    290                 295                 300

Ala Gly Lys Pro Arg Ala Val Arg Gly Leu Ala Thr Asn Val Ala Asn
305                 310                 315                 320

Tyr Asn Ala Trp Ser Ile Ser Ser Pro Pro Tyr Thr Ser Pro Asn
                325                 330                 335

Pro Asn Tyr Asp Glu Lys His Tyr Ile Glu Ala Phe Arg Pro Leu Leu
            340                 345                 350

Glu Ala Arg Gly Phe Pro Ala Gln Phe Ile Val Asp Gln Gly Arg Ser
        355                 360                 365

Gly Lys Gln Pro Thr Gly Gln Lys Glu Trp Gly His Trp Cys Asn Ala
    370                 375                 380

Ile Gly Thr Gly Phe Gly Met Arg Pro Thr Ala Asn Thr Gly His Gln
385                 390                 395                 400

Tyr Val Asp Ala Phe Val Trp Val Lys Pro Gly Gly Glu Cys Asp Gly
                405                 410                 415

Thr Ser Asp Thr Thr Ala Ala Arg Tyr Asp Tyr His Cys Gly Leu Glu
            420                 425                 430

Asp Ala Leu Lys Pro Ala Pro Glu Ala Gly Gln Trp Phe Gln Ala Tyr
        435                 440                 445

Phe Glu Gln Leu Leu Arg Asn Ala Asn Pro Pro Phe
    450                 455                 460

<210> SEQ ID NO 6
<211> LENGTH: 457
<212> TYPE: PRT
<213> ORGANISM: A. cellulolyticus

<400> SEQUENCE: 6

Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Val Gly Thr Thr Ser Pro Pro Thr
65                  70                  75                  80

Thr Thr Thr Thr Lys Ala Ser Thr Thr Thr Thr Ala Ala Ala
                85                  90                  95

Ser Gly Asn Pro Phe Ser Gly Tyr Gln Leu Tyr Ala Asn Pro Tyr Tyr
            100                 105                 110
```

```
Ser Ser Glu Val His Thr Leu Ala Ile Pro Ser Leu Thr Gly Ser Leu
        115                 120                 125

Ala Ala Ala Ala Thr Lys Ala Glu Ile Pro Ser Phe Val Trp Leu
        130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Ile Ala Gly Ile Phe
                165                 170                 175

Val Val Tyr Asp Leu Pro Asp Arg Asp Cys Ala Ala Ala Ser Asn
        180                 185                 190

Gly Glu Tyr Thr Val Ala Asn Asn Gly Val Ala Asn Tyr Lys Ala Tyr
        195                 200                 205

Ile Asp Ser Ile Val Ala Gln Leu Lys Ala Tyr Pro Asp Val His Thr
        210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
                245                 250                 255

Asn Tyr Ala Leu Ile Asn Leu Asn Leu Ala Asn Val Ala Met Tyr Ile
                260                 265                 270

Asp Ala Gly His Ala Gly Trp Leu Gly Trp Ser Ala Asn Leu Ser Pro
        275                 280                 285

Ala Ala Gln Leu Phe Ala Thr Val Tyr Lys Asn Ala Ser Ala Pro Ala
        290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
                340                 345                 350

Pro Asn Ala His Phe Ile Met Asp Thr Ser Arg Asn Gly Val Gln Pro
        355                 360                 365

Thr Lys Gln Gln Ala Trp Gly Asp Trp Cys Asn Val Ile Gly Thr Gly
        370                 375                 380

Phe Gly Val Gln Pro Thr Thr Asn Thr Gly Asp Pro Leu Glu Asp Ala
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Asp Ala Leu Gln
                420                 425                 430

Pro Ala Pro Glu Ala Gly Thr Trp Phe Gln Ala Tyr Phe Val Gln Leu
        435                 440                 445

Leu Thr Asn Ala Asn Pro Ala Leu Val
        450                 455

<210> SEQ ID NO 7
<211> LENGTH: 418
<212> TYPE: PRT
<213> ORGANISM: A. bisporus

<400> SEQUENCE: 7

Gln Ser Pro Val Trp Gly Gln Cys Gly Gly Asn Gly Trp Thr Gly Pro
1               5                   10                  15

Thr Thr Cys Ala Ser Gly Ser Thr Cys Val Lys Gln Asn Asp Phe Tyr
```

```
                20                  25                  30
Ser Gln Cys Leu Pro Asn Asn Gln Ala Pro Ser Thr Thr Thr Gln
            35                  40                  45

Pro Gly Thr Thr Pro Ala Thr Thr Ser Gly Gly Thr Gly Pro
        50                  55                  60

Thr Ser Gly Ala Gly Asn Pro Tyr Thr Gly Lys Thr Val Trp Leu Ser
65                  70                  75                  80

Pro Phe Tyr Ala Asp Glu Val Ala Gln Ala Ala Asp Ile Ser Asn
                85                  90                  95

Pro Ser Leu Ala Thr Lys Ala Ala Ser Val Ala Lys Ile Pro Thr Phe
                100                 105                 110

Val Trp Phe Asp Thr Val Ala Lys Val Pro Asp Leu Gly Gly Tyr Leu
            115                 120                 125

Ala Asp Ala Arg Ser Lys Asn Gln Leu Val Gln Ile Val Val Tyr Asp
            130                 135                 140

Leu Pro Asp Arg Asp Cys Ala Ala Leu Ala Ser Asn Gly Glu Phe Ser
145                 150                 155                 160

Leu Ala Asn Asp Gly Leu Asn Lys Tyr Lys Asn Tyr Val Asp Gln Leu
                165                 170                 175

Ala Ala Gln Ile Lys Gln Phe Pro Asp Val Ser Val Val Ala Val Ile
                180                 185                 190

Glu Pro Asp Ser Leu Ala Asn Leu Val Thr Asn Leu Asn Val Gln Lys
            195                 200                 205

Cys Ala Asn Ala Gln Ser Ala Tyr Lys Glu Gly Val Ile Tyr Ala Val
            210                 215                 220

Gln Lys Leu Asn Ala Val Gly Val Thr Met Tyr Ile Asp Ala Gly His
225                 230                 235                 240

Ala Gly Trp Leu Gly Trp Pro Ala Asn Leu Ser Pro Ala Ala Gln Leu
                245                 250                 255

Phe Ala Gln Ile Tyr Arg Asp Ala Gly Ser Pro Arg Asn Leu Arg Gly
                260                 265                 270

Ile Ala Thr Asn Val Ala Asn Phe Asn Ala Leu Arg Ala Ser Ser Pro
            275                 280                 285

Asp Pro Ile Thr Gln Gly Asn Ser Asn Tyr Asp Glu Ile His Tyr Ile
            290                 295                 300

Glu Ala Leu Ala Pro Met Leu Ser Asn Ala Gly Phe Pro Ala His Phe
305                 310                 315                 320

Ile Val Asp Gln Gly Arg Ser Gly Val Gln Asn Ile Arg Asp Gln Trp
                325                 330                 335

Gly Asp Trp Cys Asn Val Lys Gly Ala Gly Phe Gly Gln Arg Pro Thr
                340                 345                 350

Thr Asn Thr Gly Ser Ser Leu Ile Asp Ala Ile Val Trp Val Lys Pro
            355                 360                 365

Gly Gly Glu Cys Asp Gly Thr Ser Asp Asn Ser Ser Pro Arg Phe Asp
            370                 375                 380

Ser His Cys Ser Leu Ser Asp Ala His Gln Pro Ala Pro Glu Ala Gly
385                 390                 395                 400

Thr Trp Phe Gln Ala Tyr Phe Glu Thr Leu Val Ala Asn Ala Asn Pro
                405                 410                 415

Ala Leu

<210> SEQ ID NO 8
<211> LENGTH: 446
```

```
<212> TYPE: PRT
<213> ORGANISM: F. oxysporum

<400> SEQUENCE: 8

Ala Pro Val Glu Glu Arg Gln Ser Cys Ser Asn Gly Val Trp Ala Gln
1               5                   10                  15

Cys Gly Gly Gln Asn Trp Ser Gly Thr Pro Cys Cys Thr Ser Gly Asn
            20                  25                  30

Lys Cys Val Lys Leu Asn Asp Phe Tyr Ser Gln Cys Gln Pro Gly Ser
        35                  40                  45

Ala Glu Pro Ser Ser Thr Ala Ala Gly Pro Ser Ser Thr Thr Ala Thr
    50                  55                  60

Lys Thr Thr Ala Thr Gly Gly Ser Ser Thr Thr Ala Gly Gly Ser Val
65                  70                  75                  80

Thr Ser Ala Pro Pro Ala Ala Ser Asp Asn Pro Tyr Ala Gly Val Asp
                85                  90                  95

Leu Trp Ala Asn Asn Tyr Tyr Arg Ser Glu Val Met Asn Leu Ala Val
            100                 105                 110

Pro Lys Leu Ser Gly Ala Lys Ala Thr Ala Ala Lys Val Ala Asp
        115                 120                 125

Val Pro Ser Phe Gln Trp Met Asp Thr Tyr Asp His Ile Ser Leu Met
130                 135                 140

Glu Asp Thr Leu Ala Asp Ile Arg Lys Ala Asn Lys Ala Gly Gly Lys
145                 150                 155                 160

Tyr Ala Gly Gln Phe Val Val Tyr Asp Leu Pro Asn Arg Asp Cys Ala
                165                 170                 175

Ala Ala Ala Ser Asn Gly Glu Tyr Ser Leu Asp Lys Asp Gly Ala Asn
            180                 185                 190

Lys Tyr Lys Ala Tyr Ile Ala Lys Ile Lys Gly Ile Leu Gln Asn Tyr
        195                 200                 205

Ser Asp Thr Lys Val Ile Leu Val Ile Glu Pro Asp Ser Leu Ala Asn
    210                 215                 220

Leu Val Thr Asn Leu Asn Val Asp Lys Cys Ala Lys Ala Glu Ser Ala
225                 230                 235                 240

Tyr Lys Glu Leu Thr Val Tyr Ala Ile Lys Glu Leu Asn Leu Pro Asn
                245                 250                 255

Val Ser Met Tyr Leu Asp Ala Gly His Gly Gly Trp Leu Gly Trp Pro
            260                 265                 270

Ala Asn Ile Gly Pro Ala Ala Lys Leu Tyr Ala Gln Ile Tyr Lys Asp
        275                 280                 285

Ala Gly Lys Pro Ser Arg Val Arg Gly Leu Val Thr Asn Val Ser Asn
    290                 295                 300

Tyr Asn Gly Trp Lys Leu Ser Thr Lys Pro Asp Tyr Thr Glu Ser Asn
305                 310                 315                 320

Pro Asn Tyr Asp Glu Gln Arg Tyr Ile Asn Ala Phe Ala Pro Leu Leu
                325                 330                 335

Ala Gln Glu Gly Trp Ser Asn Val Lys Phe Ile Val Asp Gln Gly Arg
            340                 345                 350

Ser Gly Lys Gln Pro Thr Gly Gln Lys Ala Gln Gly Asp Trp Cys Asn
        355                 360                 365

Ala Lys Gly Thr Gly Phe Gly Leu Arg Pro Thr Asn Thr Gly Asp
    370                 375                 380

Ala Leu Ala Asp Ala Phe Val Trp Val Lys Pro Gly Gly Glu Ser Asp
385                 390                 395                 400
```

```
Gly Thr Ser Asp Thr Ser Ala Ala Arg Tyr Asp Tyr His Cys Gly Leu
                405                 410                 415

Asp Asp Ala Leu Lys Pro Ala Pro Glu Ala Gly Thr Trp Phe Gln Ala
            420                 425                 430

Tyr Phe Glu Gln Leu Leu Asp Asn Ala Asn Pro Ser Phe Leu
        435                 440                 445

<210> SEQ ID NO 9
<211> LENGTH: 460
<212> TYPE: PRT
<213> ORGANISM: P. chrysosporium

<400> SEQUENCE: 9

Met Lys Ser Thr Ala Phe Phe Ala Ala Leu Val Thr Leu Leu Pro Ala
1               5                   10                  15

Tyr Val Ala Gly Gln Ala Ser Glu Trp Gly Gln Cys Gly Gly Ile Gly
            20                  25                  30

Trp Thr Gly Pro Thr Thr Cys Val Ser Gly Thr Thr Cys Thr Val Leu
        35                  40                  45

Asn Pro Tyr Tyr Ser Gln Cys Leu Pro Gly Ser Ala Val Thr Thr Thr
50                  55                  60

Ser Val Ile Thr Ser His Ser Ser Val Ser Val Ser Ser His
65                  70                  75                  80

Ser Gly Ser Ser Thr Ser Thr Ser Ser Pro Thr Gly Pro Thr Gly Thr
                85                  90                  95

Asn Pro Pro Pro Pro Ser Ala Asn Asn Pro Trp Thr Gly Phe Gln
            100                 105                 110

Ile Phe Leu Ser Pro Tyr Tyr Ala Asn Glu Val Ala Ala Ala Ala Lys
        115                 120                 125

Gln Ile Thr Asp Pro Thr Leu Ser Ser Lys Ala Ala Ser Val Ala Asn
130                 135                 140

Ile Pro Thr Phe Thr Trp Leu Asp Ser Val Ala Lys Ile Pro Asp Leu
145                 150                 155                 160

Gly Thr Tyr Leu Ala Ser Ala Ser Ala Leu Gly Lys Ser Thr Gly Thr
                165                 170                 175

Lys Gln Leu Val Gln Ile Val Ile Tyr Asp Leu Pro Asp Arg Asp Cys
            180                 185                 190

Ala Ala Lys Ala Ser Asn Gly Glu Phe Ser Ile Ala Asn Asn Gly Gln
        195                 200                 205

Ala Asn Tyr Glu Asn Tyr Ile Asp Gln Ile Val Ala Gln Ile Gln Gln
210                 215                 220

Phe Pro Asp Val Arg Val Val Ala Val Ile Glu Pro Asp Ser Leu Ala
225                 230                 235                 240

Asn Leu Val Thr Asn Leu Asn Val Gln Lys Cys Ala Asn Ala Lys Thr
                245                 250                 255

Thr Tyr Leu Ala Cys Val Asn Tyr Ala Leu Thr Asn Leu Ala Lys Val
            260                 265                 270

Gly Val Tyr Met Tyr Met Asp Ala Gly His Ala Gly Trp Leu Gly Trp
        275                 280                 285

Pro Ala Asn Leu Ser Pro Ala Ala Gln Leu Phe Thr Gln Val Trp Gln
290                 295                 300

Asn Ala Gly Lys Ser Pro Phe Ile Lys Gly Leu Ala Thr Asn Val Ala
305                 310                 315                 320

Asn Tyr Asn Ala Leu Gln Ala Ala Ser Pro Asp Pro Ile Thr Gln Gly
```

```
                        325                 330                 335
Asn Pro Asn Tyr Asp Glu Ile His Tyr Ile Asn Ala Leu Ala Pro Leu
                340                 345                 350

Leu Gln Gln Ala Gly Trp Asp Ala Thr Phe Ile Val Asp Gln Gly Arg
            355                 360                 365

Ser Gly Val Gln Asn Ile Arg Gln Gln Trp Gly Asp Trp Cys Asn Ile
        370                 375                 380

Lys Gly Ala Gly Phe Gly Thr Arg Pro Thr Thr Asn Thr Gly Ser Gln
385                 390                 395                 400

Phe Ile Asp Ser Ile Val Trp Val Lys Pro Gly Gly Glu Cys Asp Gly
                405                 410                 415

Thr Ser Asn Ser Ser Ser Pro Arg Tyr Asp Ser Thr Cys Ser Leu Pro
                420                 425                 430

Asp Ala Ala Gln Pro Ala Pro Glu Ala Gly Thr Trp Phe Gln Ala Tyr
                435                 440                 445

Phe Gln Thr Leu Val Ser Ala Ala Asn Pro Pro Leu
                450                 455                 460

<210> SEQ ID NO 10
<211> LENGTH: 459
<212> TYPE: PRT
<213> ORGANISM: T. emersonii

<400> SEQUENCE: 10

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
                20                  25                  30

Thr Gly Ala Thr Ser Cys Ala Ala Gly Ala Thr Cys Ser Thr Ile Asn
            35                  40                  45

Pro Tyr Tyr Ala Gln Cys Val Pro Ala Thr Ala Thr Pro Thr Thr Leu
        50                  55                  60

Thr Thr Thr Thr Lys Pro Thr Ser Thr Gly Gly Ala Ala Pro Thr Thr
65              70                  75                  80

Pro Pro Pro Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Val Ile Glu Pro Asp Ser Leu Ala Asn Val
225                 230                 235                 240
```

-continued

```
Val Thr Asn Leu Asn Val Pro Lys Cys Ala Asn Ala Gln Asp Ala Tyr
            245                 250                 255

Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
            275                 280                 285

Asn Leu Ala Pro Ala Ala Gln Leu Phe Ala Ser Val Tyr Lys Asn Ala
            290                 295                 300

Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
            325                 330                 335

Asn Cys Asp Glu Glu Asp Tyr Val Asn Ala Leu Gly Pro Leu Phe Gln
            340                 345                 350

Glu Gln Gly Phe Pro Ala Tyr Phe Ile Ile Asp Thr Ser Arg Asn Gly
            355                 360                 365

Val Arg Pro Thr Lys Gln Ser Gln Trp Gly Asp Trp Cys Asn Val Ile
            370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
            405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
            435                 440                 445

Glu Gln Leu Leu Thr Asn Ala Asn Pro Leu Phe
    450                 455

<210> SEQ ID NO 11
<211> LENGTH: 558
<212> TYPE: PRT
<213> ORGANISM: T. fusca

<400> SEQUENCE: 11

Ala Gly Cys Ser Val Asp Tyr Thr Val Asn Ser Trp Gly Thr Gly Phe
1               5                   10                  15

Thr Ala Asn Val Thr Ile Thr Asn Leu Gly Ser Ala Ile Asn Gly Trp
            20                  25                  30

Thr Leu Glu Trp Asp Phe Pro Gly Asn Gln Gln Val Thr Asn Leu Trp
            35                  40                  45

Asn Gly Thr Tyr Thr Gln Ser Gly Gln His Val Ser Val Ser Asn Ala
    50                  55                  60

Pro Tyr Asn Ala Ser Ile Pro Ala Asn Gly Thr Val Glu Phe Gly Phe
65                  70                  75                  80

Asn Gly Ser Tyr Ser Gly Ser Asn Asp Ile Pro Ser Ser Phe Lys Leu
            85                  90                  95

Asn Gly Val Thr Cys Asp Gly Ser Asp Asp Pro Asp Glu Pro Ser
            100                 105                 110

Pro Ser Pro Ser Pro Ser Pro Thr Asp Pro Asp Glu Pro Gly
            115                 120                 125

Gly Pro Thr Asn Pro Pro Thr Asn Pro Gly Glu Lys Val Asp Asn Pro
    130                 135                 140

Phe Glu Gly Ala Lys Leu Tyr Val Asn Pro Val Trp Ser Ala Lys Ala
145                 150                 155                 160
```

```
Ala Ala Glu Pro Gly Gly Ser Ala Val Ala Asn Glu Ser Thr Ala Val
            165                 170                 175

Trp Leu Asp Arg Ile Gly Ala Ile Glu Gly Asn Asp Ser Pro Thr Thr
            180                 185                 190

Gly Ser Met Gly Leu Arg Asp His Leu Glu Glu Ala Val Arg Gln Ser
            195                 200                 205

Gly Gly Asp Pro Leu Thr Ile Gln Val Val Ile Tyr Asn Leu Pro Gly
            210                 215                 220

Arg Asp Cys Ala Ala Leu Ala Ser Asn Gly Glu Leu Gly Pro Asp Glu
225                 230                 235                 240

Leu Asp Arg Tyr Lys Ser Glu Tyr Ile Asp Pro Ile Ala Asp Ile Met
            245                 250                 255

Trp Asp Phe Ala Asp Tyr Glu Asn Leu Arg Ile Val Ala Ile Ile Glu
            260                 265                 270

Ile Asp Ser Leu Pro Asn Leu Val Thr Asn Val Gly Gly Asn Gly Gly
            275                 280                 285

Thr Glu Leu Cys Ala Tyr Met Lys Gln Asn Gly Gly Tyr Val Asn Gly
            290                 295                 300

Val Gly Tyr Ala Leu Arg Lys Leu Gly Glu Ile Pro Asn Val Tyr Asn
305                 310                 315                 320

Tyr Ile Asp Ala Ala His His Gly Trp Ile Gly Trp Asp Ser Asn Phe
            325                 330                 335

Gly Pro Ser Val Asp Ile Phe Tyr Glu Ala Ala Asn Ala Ser Gly Ser
            340                 345                 350

Thr Val Asp Tyr Val His Gly Phe Ile Ser Asn Thr Ala Asn Tyr Ser
            355                 360                 365

Ala Thr Val Glu Pro Tyr Leu Asp Val Asn Gly Thr Val Asn Gly Gln
            370                 375                 380

Leu Ile Arg Gln Ser Lys Trp Val Asp Trp Asn Gln Tyr Val Asp Glu
385                 390                 395                 400

Leu Ser Phe Val Gln Asp Leu Arg Gln Ala Leu Ile Ala Lys Gly Phe
            405                 410                 415

Arg Ser Asp Ile Gly Met Leu Ile Asp Thr Ser Arg Asn Gly Trp Gly
            420                 425                 430

Gly Pro Asn Arg Pro Thr Gly Pro Ser Ser Ser Thr Asp Leu Asn Thr
            435                 440                 445

Tyr Val Asp Glu Ser Arg Ile Asp Arg Arg Ile His Pro Gly Asn Trp
450                 455                 460

Cys Asn Gln Ala Gly Ala Gly Leu Gly Glu Arg Pro Thr Val Asn Pro
465                 470                 475                 480

Ala Pro Gly Val Asp Ala Tyr Val Trp Val Lys Pro Pro Gly Glu Ser
            485                 490                 495

Asp Gly Ala Ser Glu Glu Ile Pro Asn Asp Glu Gly Lys Gly Phe Asp
            500                 505                 510

Arg Met Cys Asp Pro Thr Tyr Gln Gly Asn Ala Arg Asn Gly Asn Asn
            515                 520                 525

Pro Ser Gly Ala Leu Pro Asn Ala Pro Ile Ser Gly His Trp Phe Ser
            530                 535                 540

Ala Gln Phe Arg Glu Leu Leu Ala Asn Ala Tyr Pro Pro Leu
545                 550                 555

<210> SEQ ID NO 12
<211> LENGTH: 410
```

```
<212> TYPE: PRT
<213> ORGANISM: T. fusca

<400> SEQUENCE: 12

Asn Asp Ser Pro Phe Tyr Val Asn Pro Asn Met Ser Ser Ala Glu Trp
1               5                   10                  15

Val Arg Asn Asn Pro Asn Asp Pro Arg Thr Pro Val Ile Arg Asp Arg
            20                  25                  30

Ile Ala Ser Val Pro Gln Gly Thr Trp Phe Ala His His Asn Pro Gly
        35                  40                  45

Gln Ile Thr Gly Gln Val Asp Ala Leu Met Ser Ala Gln Ala Ala
    50                  55                  60

Gly Lys Ile Pro Ile Leu Val Val Tyr Asn Ala Pro Gly Arg Asp Cys
65              70                  75                  80

Gly Asn His Ser Ser Gly Gly Ala Pro Ser His Ser Ala Tyr Arg Ser
                85                  90                  95

Trp Ile Asp Glu Phe Ala Ala Gly Leu Lys Asn Arg Pro Ala Tyr Ile
            100                 105                 110

Ile Val Glu Pro Asp Leu Ile Ser Leu Met Ser Ser Cys Met Gln His
        115                 120                 125

Val Gln Gln Glu Val Leu Glu Thr Met Ala Tyr Ala Gly Lys Ala Leu
130                 135                 140

Lys Ala Gly Ser Ser Gln Ala Arg Ile Tyr Phe Asp Ala Gly His Ser
145                 150                 155                 160

Ala Trp His Ser Pro Ala Gln Met Ala Ser Trp Leu Gln Gln Ala Asp
                165                 170                 175

Ile Ser Asn Ser Ala His Gly Ile Ala Thr Asn Thr Ser Asn Tyr Arg
            180                 185                 190

Trp Thr Ala Asp Glu Val Ala Tyr Ala Lys Ala Val Leu Ser Ala Ile
        195                 200                 205

Gly Asn Pro Ser Leu Arg Ala Val Ile Asp Thr Ser Arg Asn Gly Asn
210                 215                 220

Gly Pro Ala Gly Asn Glu Trp Cys Asp Pro Ser Gly Arg Ala Ile Gly
225                 230                 235                 240

Thr Pro Ser Thr Thr Asn Thr Gly Asp Pro Met Ile Asp Ala Phe Leu
                245                 250                 255

Trp Ile Lys Leu Pro Gly Glu Ala Asp Gly Cys Ile Ala Gly Ala Gly
            260                 265                 270

Gln Phe Val Pro Gln Ala Ala Tyr Glu Met Ala Leu Ala Ala Gly Gly
        275                 280                 285

Thr Asn Pro Asn Pro Asn Pro Asn Pro Thr Pro Thr Pro Thr Pro Thr
290                 295                 300

Pro Thr Pro Pro Gly Ser Ser Gly Ala Cys Thr Ala Thr Tyr Thr
305                 310                 315                 320

Ile Ala Asn Glu Trp Asn Asp Gly Phe Gln Ala Thr Val Thr Val Thr
                325                 330                 335

Ala Asn Gln Asn Ile Thr Gly Trp Thr Val Thr Trp Thr Phe Thr Asp
            340                 345                 350

Gly Gln Thr Ile Thr Asn Ala Trp Asn Ala Asp Val Ser Thr Ser Gly
        355                 360                 365

Ser Ser Val Thr Ala Arg Asn Val Gly His Asn Gly Thr Leu Ser Gln
370                 375                 380

Gly Ala Ser Thr Glu Phe Gly Phe Val Gly Ser Lys Gly Asn Ser Asn
385                 390                 395                 400
```

```
Ser Val Pro Thr Leu Thr Cys Ala Ala Ser
                405             410

<210> SEQ ID NO 13
<211> LENGTH: 418
<212> TYPE: PRT
<213> ORGANISM: C. fimi

<400> SEQUENCE: 13

Ala Pro Gly Cys Arg Val Asp Tyr Ala Val Thr Asn Gln Trp Pro Gly
1               5                   10                  15

Gly Phe Gly Ala Asn Val Thr Ile Thr Asn Leu Gly Asp Pro Val Ser
            20                  25                  30

Ser Trp Lys Leu Asp Trp Thr Tyr Thr Ala Gly Gln Arg Ile Gln Gln
        35                  40                  45

Leu Trp Asn Gly Thr Ala Ser Thr Asn Gly Gly Gln Val Ser Val Thr
    50                  55                  60

Ser Leu Pro Trp Asn Gly Ser Ile Pro Thr Gly Gly Thr Ala Ser Phe
65                  70                  75                  80

Gly Phe Asn Gly Ser Trp Ala Gly Ser Asn Pro Thr Pro Ala Ser Phe
                85                  90                  95

Ser Leu Asn Gly Thr Thr Cys Thr Gly Thr Val Pro Thr Thr Ser Pro
            100                 105                 110

Thr Pro Thr Pro Thr Pro Thr Pro Thr Pro Thr Pro Thr Pro Thr Pro Thr
        115                 120                 125

Pro Thr Pro Thr Pro Thr Val Thr Pro Gln Pro Thr Ser Gly Phe Tyr
    130                 135                 140

Val Asp Pro Thr Thr Gln Gly Tyr Arg Ala Trp Gln Ala Ala Ser Gly
145                 150                 155                 160

Thr Asp Lys Ala Leu Leu Glu Lys Ile Ala Leu Thr Pro Gln Ala Tyr
                165                 170                 175

Trp Val Gly Asn Trp Ala Asp Ala Ser His Ala Gln Ala Glu Val Ala
            180                 185                 190

Asp Tyr Thr Gly Arg Ala Val Ala Ala Gly Lys Thr Pro Met Leu Val
        195                 200                 205

Val Tyr Ala Ile Pro Gly Arg Asp Cys Gly Ser His Ser Gly Gly Gly
    210                 215                 220

Val Ser Glu Ser Glu Tyr Ala Arg Trp Val Asp Thr Val Ala Gln Gly
225                 230                 235                 240

Ile Lys Gly Asn Pro Ile Val Ile Leu Glu Pro Asp Ala Leu Ala Gln
                245                 250                 255

Leu Gly Asp Cys Ser Gly Gln Gly Asp Arg Val Gly Phe Leu Lys Tyr
            260                 265                 270

Ala Ala Lys Ser Leu Thr Leu Lys Gly Ala Arg Val Tyr Ile Asp Ala
        275                 280                 285

Gly His Ala Lys Trp Leu Ser Val Asp Thr Pro Val Asn Arg Leu Asn
    290                 295                 300

Gln Val Gly Phe Glu Tyr Ala Val Gly Phe Ala Leu Asn Thr Ser Asn
305                 310                 315                 320

Tyr Gln Thr Thr Ala Asp Ser Lys Ala Tyr Gln Gln Ile Ser Gln
                325                 330                 335

Arg Leu Gly Gly Lys Lys Phe Val Ile Asp Thr Ser Arg Asn Gly Asn
            340                 345                 350

Gly Ser Asn Gly Glu Trp Cys Asn Pro Arg Gly Arg Ala Leu Gly Glu
```

```
              355                 360                 365
Arg Pro Val Ala Val Asn Asp Gly Ser Gly Leu Asp Ala Leu Leu Trp
    370                 375                 380

Val Lys Leu Pro Gly Glu Ser Asp Gly Ala Cys Asn Gly Gly Pro Ala
385                 390                 395                 400

Ala Gly Gln Trp Trp Gln Glu Ile Ala Leu Gly Met Ala Arg Asn Ala
                405                 410                 415

Arg Trp

<210> SEQ ID NO 14
<211> LENGTH: 447
<212> TYPE: PRT
<213> ORGANISM: Artificial Sequence
<220> FEATURE:
<223> OTHER INFORMATION: Synthetic amino acid sequence of the mature
      CBH2 variant

<400> SEQUENCE: 14

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Leu Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Lys Val Pro Ser Phe Val Trp Leu Asp Thr Leu Asp Lys Thr Pro Leu
130                 135                 140

Met Glu Gln Thr Leu Ala Asp Ile Arg Ala Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Val Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
```

```
                    290                 295                 300
Asn Tyr Asn Gly Trp Asn Ile Thr Ser Pro Pro Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Tyr His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 15
<211> LENGTH: 29
<212> TYPE: DNA
<213> ORGANISM: Artificial Sequence
<220> FEATURE:
<223> OTHER INFORMATION: GGHTK22 forward synthetic primer

<400> SEQUENCE: 15
caccatgatc gtgggaattc ttactactc                                     29

<210> SEQ ID NO 16
<211> LENGTH: 24
<212> TYPE: DNA
<213> ORGANISM: Artificial Sequence
<220> FEATURE:
<223> OTHER INFORMATION: GGTHK23 reverse synthetic primer

<400> SEQUENCE: 16
ctacaaaaac gaagggttcg catt                                          24
```

COMPOSITIONS AND METHODS COMPRISING CELLULASE VARIANTS WITH REDUCED AFFINITY TO NON-CELLULOSIC MATERIALS

I. CROSS-REFERENCE TO RELATED APPLICATION

This application is a divisional of U.S. application Ser. No. 12/477,887, filed Jun. 3, 2009, which claims the benefit of U.S. Provisional Application No. 61/059,506, filed Jun. 6, 2008, each of which are incorporated herein by reference.

II. STATEMENT AS TO RIGHTS TO INVENTIONS MADE UNDER FEDERALLY SPONSORED RESEARCH AND DEVELOPMENT

This invention was made with Government support under conditional award no: DE-FC36-08GO18078 awarded by the Department of Energy. The Government has certain rights in this invention.

III. FIELD

The present disclosure relates to enzymes and in particular cellulase variants. Also described are nucleic acids encoding the cellulase variants, compositions comprising the cellulase variants, methods of identifying additional useful cellulase variants and methods of using the compositions.

IV. BACKGROUND

Cellulose and hemicellulose are the most abundant plant materials produced by photosynthesis. They can be degraded and used as an energy source by numerous microorganisms (e.g., bacteria, yeast and fungi) that produce extracellular enzymes capable of hydrolysis of the polymeric substrates to monomeric sugars (Aro et al., J Biol Chem, 276: 24309-24314, 2001). As the limits of non-renewable resources approach, the potential of cellulose to become a major renewable energy resource is enormous (Krishna et al., Bioresource Tech, 77: 193-196, 2001). The effective utilization of cellulose through biological processes is one approach to overcoming the shortage of foods, feeds, and fuels (Ohmiya et al., Biotechnol Gen Engineer Rev, 14: 365-414, 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., TIBTECH 5: 255-261, 1987; and Schulein, Methods Enzymol, 160: 234-243, 1988). Endoglucanases act mainly on the amorphous parts of the cellulose fibre, whereas cellobiohydrolases are also able to degrade crystalline cellulose (Nevalainen and Penttila, Mycota, 303-319, 1995). Thus, the presence of a cellobiohydrolase in a cellulase system is required for efficient solubilization of crystalline cellulose (Suurnakki et al., Cellulose 7: 189-209, 2000). Beta-glucosidase acts to liberate D-glucose units from cellobiose, cello-oligosaccharides, and other glucosides (Freer, J Biol Chem, 268: 9337-9342, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose (See, e.g., Wood et al., Methods in Enzymology, 160: 87-116, 1988).

The fungal cellulase classifications of CBH, EG and BG can be further expanded to include multiple components within each classification. For example, multiple CBHs, EGs and BGs have been isolated from a variety of fungal sources including *Trichoderma reesei* (also referred to as *Hypocrea jecorina*), which contains known genes for two CBHs, i.e., CBH I ("CBH1") and CBH II ("CBH2"), at least 8 EGs, i.e., EG I, EG II, EG III, EGIV, EGV, EGVI, EGVII and EGVIII, and at least 5 BGs, i.e., BG1, BG2, BG3, BG4 and BG5. EGIV, EGVI and EGVIII also have xyloglucanase activity.

In order to efficiently convert crystalline cellulose to glucose the complete cellulase system comprising components from each of the CBH, EG and BG classifications is required, with isolated components less effective in hydrolyzing crystalline cellulose (Filho et al., Can J Microbiol, 42:1-5, 1996). A synergistic relationship has been observed between cellulase components from different classifications. In particular, the EG-type cellulases and CBH-type cellulases synergistically interact to more efficiently degrade cellulose.

Cellulases are known in the art to be useful in the treatment of textiles for the purposes of enhancing the cleaning ability of detergent compositions, for use as a softening agent, for improving the feel and appearance of cotton fabrics, and the like (Kumar et al., Textile Chemist and Colorist, 29:37-42, 1997). Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; and GB App. No. 1,358,599), have been described. Hence, cellulases produced in fungi and bacteria have received significant attention. In particular, fermentation of *Trichoderma* spp. (e.g., *Trichoderma longibrachiatum* or *Trichoderma reesei*) has been shown to produce a complete cellulase system capable of degrading crystalline forms of cellulose.

Although cellulase compositions have been previously described, there remains a need for new and improved cellulase compositions. Improved cellulose compositions find used in household detergents, textile treatments, biomass conversion and paper manufacturing. Cellulases that exhibit improved performance are of particular interest.

V. SUMMARY

The present teachings relates to cellulase variants modified to reduce binding to non-cellulosic materials. In general, the cellulase variants have increased cellulolytic activity in the presence of non-cellulosic materials in comparison to wild type cellulases. In some embodiments the cellulase variants have a decreased net charge (i.e. is more negative) in comparison to wild type cellulases. In some embodiments, the cellulase variants are less positively charged than wild type cellulases. In some embodiments, a cellulase is modified by removing one or more positive charges. In some embodiments, a cellulase is modified by adding one or more negative charges. In some embodiments, a cellulase is modified by removing one or more positive charges and adding one or more negative charges.

In some embodiments, the present teachings relate to cellobiohydrolase I (CBH1) or cellobiohydrolase II (CBH2) variants. In some embodiments the cellulase variant is a mature form having cellulase activity and a substitution at one or more positions selected from the group consisting of 63, 77, 129, 147, 153, 157, 161, 194, 197, 203, 237, 239, 247, 254, 281, 285, 288, 289, 294, 327, 339, 344, 356, 378, and 382, wherein the positions are numbered by correspondence to a reference (e.g., wild type *Hypocrea jecorina* CBH2) cellulase having the amino acid sequence of SEQ ID NO:3, and wherein the substitution at one or more positions causes the cellulase variant to have a more negative net charge in comparison to the reference cellulase. In some embodiments, CBH2 is modified by removing one or more positive charges, which in some embodiments entails a replacement of a lysine or an arginine with a neutral amino acid (e.g., K or R replaced by N or Q or other neutral residue). In some embodiments, CBH2 is modified by adding one or more negative charges, which in some embodiments entails a replacement of a neutral amino acid with a negatively charged amino acid (e.g., No or Q or other neutral residue replaced by D or E). In some embodiments, CBH2 is modified by removing one or more positive charges and adding one or more negative charges, which in some embodiments entails a replacement of a lysine or an arginine with a negatively charged amino acid (e.g., K or R replaced by D or E). In general, the CBH2 variant has increased cellulolytic activity in the presence of lignin in comparison to the wild type *Hypocrea jecorina* CBH2 having the amino acid sequence of SEQ ID NO:3. The present teachings further provide CBH2 variants comprising one or more substitutions selected from the group consisting of K129E, K157E, K194E, K288E, K327E, K356E, R63Q, R77Q, R153Q, R203Q, R294Q, R378Q, N161D, N197D, N237D, N247D, N254D, N285D, N289D, N339D, N344D, N382D, Q147E, Q204E, Q239E, Q281E, D151N, D189N, D211N, D277N, D405N, E146Q, E208Q, and E244Q, in the mature form of CBH2, wherein said substitutions are numbered according to the mature form of *Hypocrea jecorina* CBH2 of SEQ ID NO:3. In some embodiments, the variant comprises a further substitution at one or more further positions selected from the group consisting of 146, 151, 189, 208, 211, 244, 277 and 405, wherein the further positions are numbered by correspondence with the amino acid sequence of the reference cellobiohydrolase II (CBH2) set forth as SEQ ID NO:3. In some embodiments, the further substitution at one or more further positions comprises a replacement of aspartic acid or glutamic acid with a neutral amino acid (e.g., D or E replaced by N or Q or other neutral residue). In some embodiments, the further substitution at one or more further positions comprises one or more of the group consisting of D151N, D189N, D211N, D277N, D405N, E146Q, E208Q, and E244Q, wherein the positions are numbered by correspondence with the amino acid sequence of the reference cellobiohydrolase II (CBH2) set forth as SEQ ID NO:3. In some preferred embodiments, the substitution at one or more positions is selected from the group consisting of 1, 2, 3, 4, 5, 6, 7, 8, 9 and 10 positions. In some preferred embodiments, the cellulase variant is derived from a parent cellulase selected from the group consisting of *Hypocrea jecorina* CBH2, *Hypocrea koningii* CBH2, *Humicola insolens* CBH2, *Acremonium cellulolyticus* CBH2, *Agaricus bisporus* CBH2, *Fusarium osysporum* EG, *Phanerochaete chrysosporium* CBH2, *Talaromyces emersonii* CBH2, *Thermobifida fusca* 6B/E3 CBH2, *Thermobifida fusca* 6A/E2 EG, and *Cellulomonas fimi* CenA EG. In some preferred embodiments, the cellulase variant is derived from a parent cellulase whose amino acid sequence is at least 75%, 80%, 85%, 90%, 95%, 96%, 97%, 98% or 99% identical to a member of the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13. In some embodiments, the more negative net charge is a −1 or −2 in comparison to the reference CBH2.

The present disclosure further provides cellulase variants, wherein the variant is a mature form having cellulase activity and comprising a chemical modification of a lysine residue to remove positive charge of the lysine residue. In some preferred embodiments, the chemical modification comprises a treatment with a compound selected from the group consisting of succinic anhydride, acetoxysuccinic anhydride, maleic anhydride, tartaric anhydride, phthalic anhydride, trimetallitic anhydride, cis-aconitic anhydride, t-nitrophthalic anhydride, acetic anhydride, butyric anhydride, isobutyric anhydride, hexanoic anhydride, valeric anhydride, isovaleric anhydride, and pivalic anhydride. In some preferred embodiments, the cellulase variant is derived from a parent cellulase selected from the group consisting of a *Hypocrea jecorina* cellobiohydrolase I, *Hypocrea jecorina* cellobiohydrolase II, *Hypocrea jecorina* endoglucanase I, *Hypocrea jecorina* endoglucanase II, and *Hypocrea jecorina* beta-glucosidase. In some preferred embodiments, the cellulase variant is derived from a parent cellulase selected from the group consisting of *Hypocrea jecorina* CBH2, *Hypocrea koningii* CBH2, *Humicola insolens* CBH2, *Acremonium cellulolyticus* CBH2, *Agaricus bisporus* CBH2, *Fusarium osysporum* EG, *Phanerochaete chrysosporium* CBH2, *Talaromyces emersonii* CBH2, *Thermobifida. fusca* 6B/E3 CBH2, *Thermobifida fusca* 6A/E2 EG, and *Cellulomonas fimi* CenA EG. Also provided are cellulase variants derived from a parent cellulase whose amino acid sequence is at least 75%, 80%, 85%, 90%, 95%, 96%, 97%, 98% or 99% identical to a member of the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13. In some embodiments, the cellulase variant comprises a substitution at one or more positions selected from the group consisting of 63, 77, 129, 147, 153, 157, 161, 194, 197, 203, 237, 239, 247, 254, 281, 285, 288, 289, 294, 327, 339, 344, 356, 378, and 382, wherein the positions are numbered by correspondence with the amino acid sequence of a reference cellobiohydrolase II (CBH2) set forth as SEQ ID NO:3.

The present teachings further relates to CBH2 variant comprising from one to twenty six substitutions selected from the group consisting of K129E, K157E, K194E, K288E, K327E, K356E, R63Q, R77Q, R153Q, R203Q, R294Q, R378Q, N161D, N197D, N237D, N247D, N254D, N285D, N289D, N339D, N344D, N382D, Q147E, Q204E, Q239E, and Q281E. In some embodiments, the CBH2 variant comprises a combination of substitutions selected from the group consisting of: i) K157E/K129E; ii) K157E/K129E/K288E/K194E; iii) K157E/K129E/K288E/K194E/K356E/K327E; iv) K157E/K129E/K288E/K194E/K356E/K327E/R153Q/R294Q/R203Q/R378Q; v) K157E/K129E/K288E/K194E/K356E/K327E/R153Q/R294Q/R203Q/R378Q/N382D/N344D/N327D/N339D; vi) K157E/K129E/K288E/K194E/K356E/K327E/R153Q/R294Q/R203Q/R378Q/N382D/N344D/N327D/N339D/N289D/N161D/Q204E/Q147E; vii) K157E/K129E/K288E/K194E/K356E/K327E/R153Q/R294Q/R203Q/R378Q  N382D/N344D/N327D/N339D/N289D/N161D/Q204E/Q147E/N285D/N197D/N254D/N247D; and viii) K157E/K129E/K288E/K194E/K356E/K327E/R153Q/R294Q/R203Q/R378Q  N382D/N344D/N327D/N339D/N289D/N161D/Q204E/Q147E/N285D/N197D/N254D/N247D/Q239E/Q281E/R63Q/R77Q.

In some embodiments, the CBH2 variant comprises from one to eight substitutions selected from the group consisting of D151N, D189N, D211N, D277N, D405N, E146Q, E208Q, and E244Q. In some embodiments, the CBH2 variant comprises a combination of substitutions selected from the group consisting: i) D189N/E208Q/D211N/D405; and ii) D189N/E208Q/D211N/D405/E244Q/D277N/D151/E146Q.

Also described are isolated nucleic acids encoding a CBH2 variant having cellobiohydrolase activity as described in the preceding paragraphs. In a first aspect, the disclosure encompasses an isolated nucleic acid encoding a polypeptide having cellobiohydrolase activity, which polypeptide is a variant of a glycosyl hydrolase of family 6, and wherein said nucleic acid encodes a substitution at a residue which decreases the net charge in comparison to the wild type *Hypocrea jecorina* CBH2.

In another aspect, the disclosure is directed to an isolated nucleic acid encoding a CBH2 variant, wherein said variant comprises a substitution at a position selected from the group consisting of K129E, K157E, K194E, K288E, K327E, K356E, R63Q, R77Q, R153Q, R203Q, R294Q, R378Q, N161D, N197D, N237D, N247D, N254D, N285D, N289D, N339D, N344D, N382D, Q147E, Q204E, Q239E, Q281E, D151N, D189N, D211N, D277N, D405N, E146Q, E208Q, and E244Q, in the mature form of CBH2, wherein said substitutions are numbered according to the mature form of *Hypocrea jecorina* CBH2 of SEQ ID NO:3.

In some embodiments, the disclosure is directed to an expression cassette comprising a nucleic acid encoding a CBH2 variant, a constructs comprising the nucleic acid of encoding the CBH2 variant operably linked to a regulatory sequence, a vector comprising a nucleic acid encoding a CBH2 variant, and host cell transformed with the vector comprising a nucleic acid encoding a CBH2 variant. The present teachings further provide methods producing a CBH2 variant by culturing the host cells expressing a CBH2 variant in a culture medium under suitable conditions to produce the CBH2 variant.

Also provided are compositions comprising the cellulase variant of the preceding paragraphs. In some preferred embodiments, the composition further comprises at least one additional enzyme selected from the group consisting of a subtilisin, a neutral metalloprotease, a lipase, a cutinize, an amylase, a carbohydrase, a pectinase, a manganese, an Arabians, a galantines, a xylanase, an oxidase, and a peroxidase Provided herein, are methods of converting biomass to sugars comprising contacting said biomass with a cellulase variant. Also provided are methods of producing a fuel by contacting a biomass composition with an enzymatic composition comprising the cellulase variant to yield a sugar solution and culturing with a fermentative microorganism under conditions sufficient to produce a fuel.

Also provided are compositions comprising cellulase variants including detergent compositions, feed additives for example, and methods of cleaning or fabric care by contacting a surface and/or an article comprising a fabric with the detergent composition. Also, provided are methods of fabric care treatment, including devilling and surface finishing, by contacting a surface and/or an article comprising a fabric with a cellulase variant.

Other objects, features and advantages of the present disclosure will become apparent from the following detailed description. It should be understood, however, that the detailed description and specific examples, while indicating preferred embodiments of the disclosure, are given by way of illustration only, since various changes and modifications within the scope and spirit of the disclosure will become apparent to one skilled in the art from this detailed description.

VI. BRIEF DESCRIPTION OF THE DRAWINGS

FIG. 1 illustrates saccharification of APB by modified (squares) and unmodified (circles) *Trichoderma* sp. cellulase preparations in the presence of increasing amounts of lignin inhibitor.

FIG. 3 provides an alignment of the amino acid sequences of the mature form of various cellulases: *Hypocrea jecorina* (also known as *T. reesei*) CBH2 (SEQ ID NO:3), *Hypocrea koningii* CBH2 (SEQ ID NO:4), *Humicola insolens* CBH2 (SEQ ID NO:5), *Acremonium* cellulolyticus CBH2 (SEQ ID NO:6), *Agaricus bisporus* CBH2 (SEQ ID NO:7), *Fusarium osysporum* EG (SEQ ID NO:8), *Phanerochaete chrysosporium* CBH2 (SEQ ID NO:9), Talaromyces emersonii CBH2 (SEQ ID NO:10), *Thermobifida. fusca* 6B/E3 CBH2 (SEQ ID NO:11), *Thermobifida fusca* 6A/E2 EG (SEQ ID NO:12), and *Cellulomonas fimi* CenA EG (SEQ ID NO:13).

Figure 4:
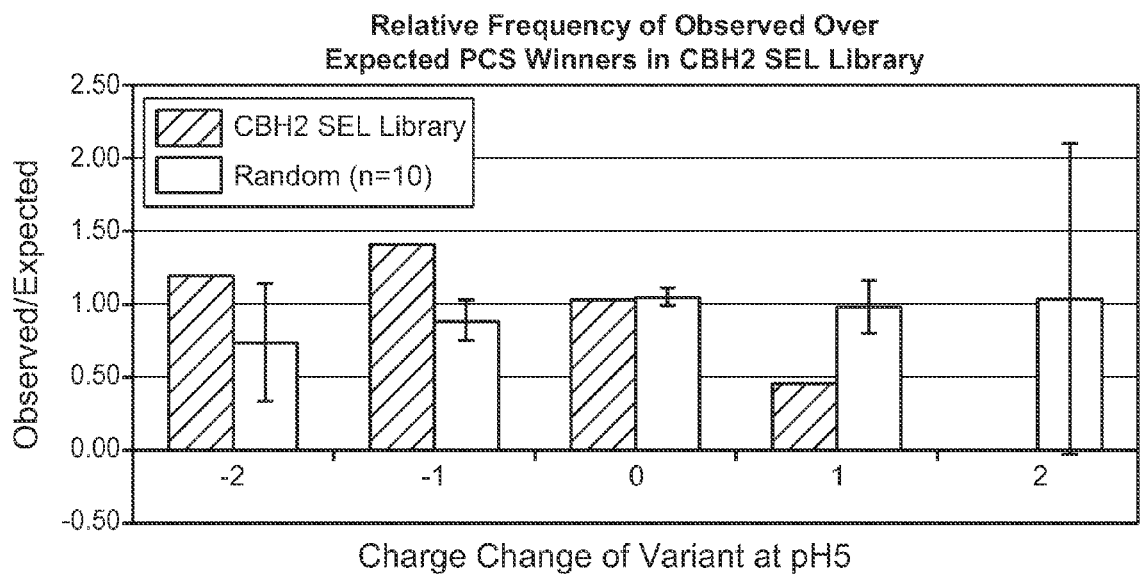

FIG. 4 provides a graph of the relative frequency of observed over expected pretreated corn stover (PCS) assay winners of the CBH2 variant Sells as a product of charge change. Decreasing CBH2 charge results in a significantly higher frequency of PCS winners.

Figure 5:
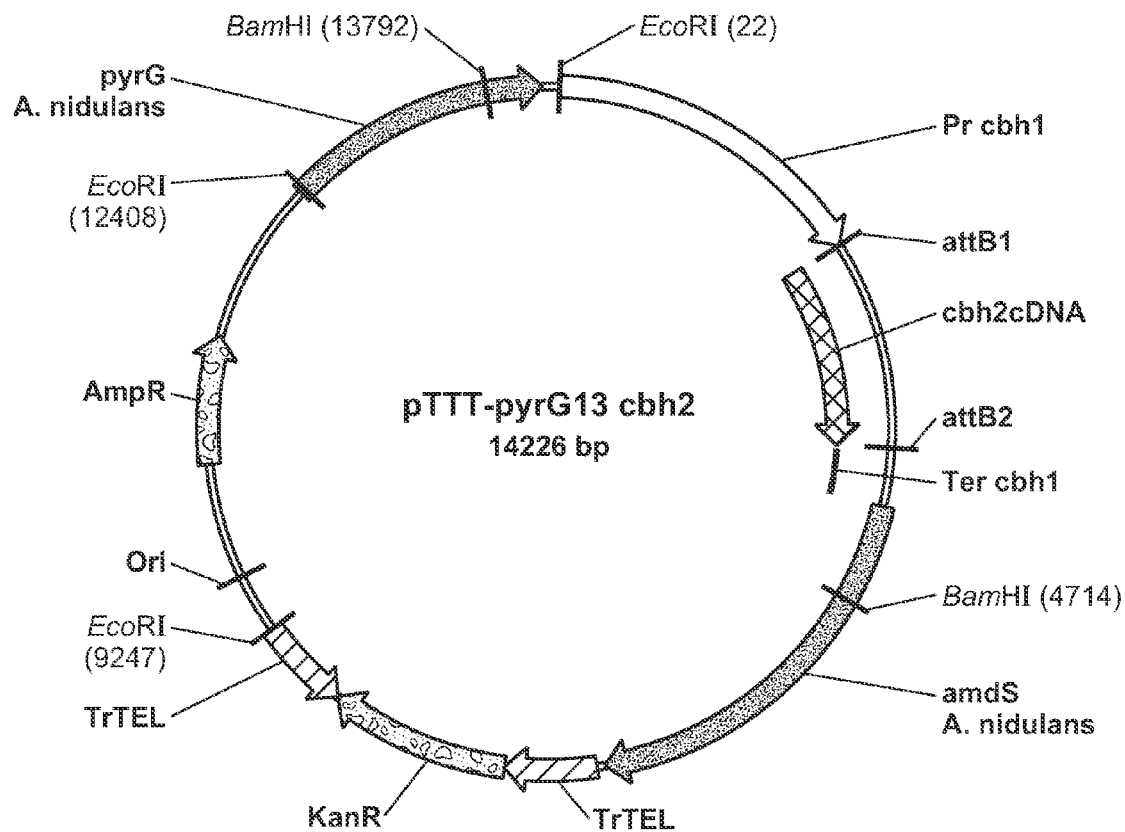

FIG. 5 provides a plasmid map of pTTTpyr-cbh2.

VII. DETAILED DESCRIPTION OF VARIOUS EMBODIMENTS

The present teachings relates to cellulase variants modified to reduce binding to non-cellulosic materials. In general, the cellulase variant has increased cellulolytic activity in the presence of non-cellulosic materials in comparison to the wild type cellulase. In some embodiments the variant cellulase has a decreased net charge (i.e. is more negative) in comparison to the wild type cellulase. In some embodiments, the cellulase variants are less positively charged than wild type cellulase. In some embodiments, a cellulase is modified by removing one or more positive charges. In some embodiments, a cellulase is modified by adding one or more negative charges. In some embodiments, a cellulase is modified by removing one or more positive charges and adding one or more negative charges.

It is to be understood that both the foregoing general description and the following detailed description are exemplary and explanatory only and are not restrictive of the compositions and methods described herein. Unless defined otherwise herein, all technical and scientific terms used herein have the same meaning as commonly understood by one of ordinary skill in the art to which this disclosure belongs. In this application, the use of the singular includes the plural unless specifically stated otherwise. The use of "or" means "and/or" unless stated otherwise. Likewise, the terms "comprise," "comprising," "comprises," "include," "including" and "includes" are not intended to be limiting. All patents and publications, including all amino acid and nucleotide sequences disclosed within such patents and publications, referred to herein are expressly incorporated by reference. The headings provided herein are not limitations of the various aspects or embodiments of the disclosure which can be had by reference to the specification as a whole. Accordingly, the terms herein are more fully defined by reference to the specification as a whole.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure. Although any methods and materials similar or equivalent to those described herein can be used in the practice or testing of the present disclosure, the preferred methods and materials are described. Numeric ranges are inclusive of the numbers defining the range. Unless otherwise indicated, nucleic acids are written left to right in 5' to 3' orientation; amino acid sequences are written left to right in amino to carboxyl orientation, respectively. Practitioners are particularly directed to Sambrook et al., MOLECULAR CLONING: A LABORATORY MANUAL (Second Edition), Cold Spring Harbor Press, Plainview, N.Y., 1989, and Ausubel F M et al., Current Protocols in Molecular Biology, John Wiley & Sons, New York, N.Y., 1993, for definitions and terms of the art. It is to be understood that this disclosure is not limited to the particular methodology, protocols, and reagents described, as these may vary.

I. Definitions

The terms below are more fully defined by reference to the specification as a whole.

The term "polypeptide" as used herein refers to a compound made up of a single chain of amino acid residues linked by peptide bonds. The term "protein" as used herein may be synonymous with the term "polypeptide".

"Variant" means a protein which is derived from a precursor protein (e.g., the native protein) by addition of one or more amino acids to either or both the C- and N-terminal end, substitution of one or more amino acids at one or a number of different sites in the amino acid sequence, or deletion of one or more amino acids at either or both ends of the protein or at one or more sites in the amino acid sequence, or one or more amino acids is modified by changing the charge (i.e. by removing a positive charge, adding a negative charge, or by both removing a positive charge and adding a negative charge). The preparation of a cellulase variant may be performed by any means know in the art, including chemical modification of amino acids, by modifying a DNA sequence which encodes for the native protein, transformation of the modified DNA sequence into a suitable host, and expression of the modified DNA sequence to form the variant enzyme. The variant cellulase of the disclosure includes peptides comprising altered amino acid sequences in comparison with a precursor enzyme amino acid sequence wherein the variant cellulase retains the characteristic cellulolytic nature of the precursor enzyme but which may have altered properties in some specific aspect. For example, a variant cellulase may have an increased pH optimum or increased temperature or oxidative stability or decreased affinity or binding to non-cellulosic materials but will retain its characteristic cellulolytic activity. It is contemplated that the variants according to the present disclosure may be derived from a DNA fragment encoding a cellulase variant wherein the functional activity of the expressed cellulase variant is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained. The terms variant and derivative may be used interchangeably herein.

"Equivalent residues" may also be defined by determining homology at the level of tertiary structure for a precursor cellulase whose tertiary structure has been determined by x-ray crystallography. Equivalent residues are defined as those for which the atomic coordinates of two or more of the main chain atoms of a particular amino acid residue of a cellulase and *Hypocrea jecorina* CBH2 (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the *H. jecorina* CBH2. The best model is the crystallographic model giving the lowest R factor for experimental diffraction data at the highest resolution available see for examples US 2006/0205042.

Equivalent residues which are functionally analogous to a specific residue of *H. jecorina* CBH2 are defined as those amino acids of a cellulase which may adopt a conformation such that they either alter, modify or contribute to protein structure, substrate binding or catalysis in a manner defined and attributed to a specific residue of the *H. jecorina* CBH2. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *H. jecorina* CBH2. The crystal structure of *H. jecorina* CBH2 is shown in Zou et al. (1999) (Ref. 5, supra).

The term "nucleic acid molecule" includes RNA, DNA and cDNA molecules. It will be understood that, as a result of the degeneracy of the genetic code, a multitude of nucleotide sequences encoding a given protein such as CBH2 and/or variants thereof may be produced. The present disclosure contemplates every possible variant nucleotide sequence, encoding variant cellulase such as CBH2, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring, for example, antibiotic resistance to transformed cells. A typical chimeric gene of the present disclosure, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode the variant cellulase such as CBH2 will hybridize, under moderate to high stringency conditions to the wild type sequence such as provided herein as SEQ ID NO:1. However, in some cases a CBH2-encoding nucleotide sequence is employed that possesses a substantially different codon usage, while the protein encoded by the CBH2-encoding nucleotide sequence has the same or substantially the same amino acid sequence as the native protein. For example, the coding sequence may be modified to facilitate faster expression of CBH2 in a particular prokaryotic or eukaryotic expression system, in accordance with the frequency with which a particular codon is utilized by the host (Te'o et al., FEMS Microbiology Letters, 190: 13-19, 2000, for example, describes the optimization of genes for expression in filamentous fungi).

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$-5° C. (5° C. below the $T_m$ of the probe); "high stringency" at about 5-10° C. below the $T_m$; "moderate" or "intermediate stringency" at about 10-20° C. below the Tm of the probe; and "low stringency" at about 20-25° C. below the $T_m$. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5 timesDenhardt's solution, 0.5% SDS and 100 ug/ml denatured carrier DNA followed by washing two times in 2 timesSSC and 0.5% SDS at room temperature and two additional times in 0.1×SSC and 0.5% SDS at 42° degreeC.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "CBH2 expression" refers to transcription and translation of the cbh2 gene or variants thereof, the products of which include precursor RNA, mRNA, polypeptide, post-translationally processed polypeptides, and derivatives thereof, including CBH2 from related species such as *Trichoderma koningii, Hypocrea jecorina* (also known as *Trichoderma longibrachiatum, Trichoderma reesei* or *Trichoderma viride*) and *Hypocrea schweinitzii*. By way of example, assays for CBH2 expression include Western blot for CBH2 protein, Northern blot analysis and reverse transcriptase polymerase chain reaction (RT-PCR) assays for cbh2 mRNA, and Phosphoric Acid Swollen Cellulose (PASC) and p-hydroxybenzoic acid hydrazide (PAHBAH) assays as described in the following: (a) PASC: (Karlsson, J. et al. (2001), Eur. J. Biochem, 268, 6498-6507, Wood, T. (1988) in Methods in Enzymology, Vol. 160. Biomass Part a Cellulose and Hemicellulose (Wood, W. & Kellog, S. Eds.), pp. 19-25, Academic Press, San Diego, Calif., USA) and (b) PAHBAH: (Lever, M. (1972) Analytical Biochemistry, 47, 273, Blakeney, A. B. & Mutton, L. L. (1980) Journal of Science of Food and Agriculture, 31, 889, Henry, R. J. (1984) Journal of the Institute of Brewing, 90, 37).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein that facilitates the secretion of the mature form of the protein outside the cell. The mature form of the extracellular protein lacks the signal sequence that is cleaved off during the secretion process.

By the term "host cell" is meant a cell that contains a vector and supports the replication, and/or transcription or transcription and translation (expression) of the expression construct. Host cells for use in the present disclosure can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*. It has now been demonstrated that the asexual industrial fungus *Trichoderma reesei* is a clonal derivative of the ascomycete *Hypocrea jecorina* (See, Kuhls et al., PNAS, 93:7755-7760, 1996).

The term "cellooligosaccharide" refers to oligosaccharide groups containing from 2-8 glucose units and having beta-1,4 linkages, e.g., cellobiose.

The terms "cellulase" "cellulolytic enzymes" or "cellulase enzymes" refer to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria. The enzymes made by these microbes are mixtures of proteins with three types of actions useful in the conversion of cellulose to glucose: endoglucanases (EG), cellobiohydrolases (CBH), and beta-glucosidase (BGL or Bglu). These three different types of cellulase enzymes act synergistically to convert cellulose and its derivatives to glucose.

Many microbes make enzymes that hydrolyze cellulose, including the wood rotting fungus *Trichoderma*, the compost bacteria *Thermomonospora, Bacillus*, and *Cellulomonas; Streptomyces*; and the fungi *Humicola, Aspergillus* and *Fusarium*.

CBH2 from *Hypocrea jecorina* is a member of the Glycosyl Hydrolase Family 6 (hence Cel6) and, specifically, was the first member of that family identified in *Hypocrea jecorina* (hence Cel6A). The Glycosyl Hydrolase Family 6 contains both Endoglucanases and Cellobiohydrolases/exoglucanases, and that CBH2 is the latter. Thus, the phrases CBH2, CBH2-type protein and Cel6 cellobiohydrolases may be used interchangeably herein.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity. Cellulose binding domain and cellulose binding module may be used interchangeably herein.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present disclosure, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the cbh2 gene" means that either that the cbh2 gene has been deleted from the genome and therefore cannot be expressed by the recombinant host microorganism; or that the cbh2 gene or transcript has been modified such that a functional CBH2 enzyme is not produced by the host microorganism or at levels that are significantly less than the unmodified cbh2 gene or transcript.

The term "variant cbh2 gene" means that the nucleic acid sequence of the cbh2 gene from *H. jecorina* has been altered by removing, adding, and/or manipulating the coding sequence.

As used herein, the term "purifying" generally refers to subjecting transgenic nucleic acid or protein containing cells to biochemical purification and/or column chromatography.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

As used herein, the term "enriched" means that the cellulase such as CBH2 is found in a concentration that is greater relative to the CBH2 concentration found in a wild-type, or naturally occurring, fungal cellulase composition. The terms enriched, elevated and enhanced may be used interchangeably herein.

A wild type fungal cellulase composition is one produced by a naturally occurring fungal source and which comprises one or more BGL, CBH and EG components wherein each of these components is found at the ratio produced by the fungal source. Thus, an enriched CBH composition would have CBH at an altered ratio wherein the ratio of CBH to other cellulase components (i.e., EGs, beta-glucosidases and other endoglucanases) is elevated. This ratio may be increased by either increasing CBH or decreasing (or eliminating) at least one other component by any means known in the art.

The term "isolated" or "purified" as used herein refers to a nucleic acid or amino acid that is removed from at least one component with which it is naturally associated.

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified CBH may then be added to the enzymatic solution resulting in an enriched CBH solution. It is also possible to elevate the amount of CBH produced by a microbe using molecular genetics methods to overexpress the gene encoding CBH, possibly in conjunction with deletion of one or more genes encoding other cellulases.

Fungal cellulases may contain more than one CBH component. The different components generally have different isoelectric points which allow for their separation via ion exchange chromatography and the like. Either a single CBH component or a combination of CBH components may be employed in an enzymatic solution.

When employed in enzymatic solutions, the homolog or variant CBH2 component is generally added in an amount sufficient to allow the highest rate of release of soluble sugars from the biomass. The amount of homolog or variant CBH2 component added depends, upon the type of biomass to be saccharified, which can be readily determined by the skilled artisan when employed, the weight percent of the homolog or variant CBH2 component present in the cellulase composition is from preferably between 1 and 100 with illustrative examples being about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 60 weight percent, from about 15 to about 65 weight percent, from about 15 to about 70 weight percent, from about 15 to about 75 weight percent, from about 15 to about 80 weight percent, from about 15 to about 85 weight percent, from about 15 to about 95 weight percent. However, when employed, the weight percent of the homolog or variant CBH2 component relative to any EG type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. Cellulases

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG").

Certain fungi produce complete cellulase systems which include exo-cellobiohydrolases or CBH-type cellulases, endoglucanases or EG-type cellulases and beta-glucosidases or BG-type cellulases. However, sometimes these systems lack CBH-type cellulases and bacterial cellulases also typically include little or no CBH-type cellulases. In addition, it has been shown that the EG components and CBH components synergistically interact to more efficiently degrade cellulose. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl beta.-D-glucosides such as methyl.beta.-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Cellulases also find a number of uses in detergent compositions including to enhance cleaning ability, as a softening agent and to improve the feel of cotton fabrics (Hemmpel, ITB Dyeing/Printing/Finishing 3:5-14, 1991; Tyndall, Textile Chemist and Colorist 24:23-26, 1992; and Kumar et al., Textile Chemist and Colorist, 29:37-42, 1997). While the mechanism is not part of the disclosure, softening and color restoration properties of cellulase have been attributed to the alkaline endoglucanase components in cellulase compositions, as exemplified by U.S. Pat. Nos. 5,648,263, 5,691,178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776,757).

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulose biomass to ethanol (wherein the cellulase degrades cellulose to glucose and yeast or other microbes further ferment the glucose into ethanol), in the treatment of mechanical pulp (Pere et al., In Proc. Tappi Pulping Conf., Nashville, Tenn., 27-31, pp. 693-696, 1996), for use as a feed additive (WO 91/04673) and in grain wet milling.

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., FEBS Lett. 204:223-227, 1986; Tomme et al., Eur. J. Biochem. 170:575-581, 1988). The CBDs are particularly important in the hydrolysis of crystalline cellulose. It has been shown that the ability of cellobiohydrolases to degrade crystalline cellulose clearly decreases when the CBD is absent (Linder and Teeri, J. Biotechnol. 57:15-28, 1997). However, the exact role and action mechanism of CBDs is still a matter of speculation. It has been suggested that the CBD enhances the enzymatic activity merely by increasing the effective enzyme concentration at the surface of cellulose (Stahlberg et al., Bio/Technol. 9:286-290, 1991), and/or by loosening single cellulose chains from the cellulose surface (Tormo et al., EMBO J. vol. 15, no. 21, pp. 5739-5751, 1996). Most studies concerning the effects of cellulase domains on different substrates have been carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei*: Shoemaker, S. et al., Bio/Technology, 1:691-696, 1983, which discloses CBH1; Teeri, T. et al., Gene, 51:43-52, 1987, which discloses CBH2. Cellulases from species other than *Trichoderma* have also been described e.g., Ooi et al., Nucleic Acids Research, vol. 18, no. 19, 1990, which discloses the cDNA sequence coding for endoglucanase F1-CMC produced by *Aspergillus aculeatus*; Kawaguchi T et al., Gene 173(2):287-8, 1996, which discloses the cloning and sequencing of the cDNA encoding beta-glucosidase 1 from *Aspergillus aculeatus*; Sakamoto et al., Curr. Genet. 27:435-439, 1995, which discloses the cDNA sequence encoding the endoglucanase CMCase-1 from *Aspergillus kawachii* IFO 4308; Saarilahti et al., Gene 90:9-14, 1990, which discloses an endoglucanase from *Erwinia carotovara*; Spilliaert R, et al., Eur J. Biochem. 224 (3):923-30, 1994, which discloses the cloning and sequencing of bglA, coding for a thermostable beta-glucanase from *Rhodothermus marinus*; and Halldorsdottir S et al., Appl Microbiol Biotechnol. 49(3):277-84, 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type, EG-type and BG-type cellulases is of interest for use: (1) in compositions for degrading wood pulp or other biomass into sugars (e.g., for biochemicals production such as bio-fuels); (2) in detergent compositions that exhibit enhanced cleaning ability (3) function as a softening agent and/or improve the feel of cotton fabrics (e.g., "stone washing" or "biopolishing"); and/ or (3) in feed compositions, for example.

Also provided herein are whole cellulase preparations comprising cellulase variants. As used herein, the phrase "whole cellulase preparation" refers to both naturally occurring and non-naturally occurring cellulase containing compositions. A "naturally occurring" composition is one produced by a naturally occurring source and which comprises one or more cellobiohydrolase-type, one or more endoglucanase-type, and one or more beta-glucosidase components wherein each of these components is found at the ratio produced by the source. A naturally occurring composition is one that is produced by an organism unmodified with respect to the cellulolytic enzymes such that the ratio of the component enzymes is unaltered from that produced by the native organism. A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzyme; or (3) modifying an organism such that at least one cellulolytic enzyme is deleted. Accordingly, in some embodiments, the whole cellulase preparation can have one or more of the various EGs and/or CBHs, and/or beta-glucosidase deleted. For example, EG1 may be deleted alone or in combination with other EGs and/or CBHs.

In general, the whole cellulase preparation includes enzymes including, but are not limited to: (i) endoglucanases (EG) or 1,4-β-d-glucan-4-glucanohydrolases (EC 3.2.1.4), (ii) exoglucanases, including 1,4-β-d-glucan glucanohydrolases (also known as cellodextrinases) (EC 3.2.1.74) and 1,4-β-d-glucan cellobiohydrolases (exo-cellobiohydrolases, CBH) (EC 3.2.1.91), and (iii) β-glucosidase (BG) or β-glucoside glucohydrolases (EC 3.2.1.21).

In the present disclosure, the whole cellulase preparation can be from any microorganism that is useful for the hydrolysis of a cellulosic material. In some embodiments, the whole cellulase preparation is a filamentous fungi whole cellulase. "Filamentous fungi" include all filamentous forms of the subdivision Eumycota and Oomycota. In some embodiments, the whole cellulase preparation is an *Acremonium, Aspergillus, Emericella, Fusarium, Humicola, Mucor, Myceliophthora, Neurospora, Scytalidium, Thielavia, Tolypocladium*, or *Trichoderma* species, whole cellulase. In some embodiments, the whole cellulase preparation is an *Aspergillus aculeatus, Aspergillus awamori, Aspergillus foetidus, Aspergillus japonicus, Aspergillus nidulans, Aspergillus niger*, or *Aspergillus oryzae* whole cellulase. In another aspect, whole cellulase preparation is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* whole cellulase. In another aspect, the whole cellulase preparation is a *Humicola insolens, Humicola lanuginosa, Mucor miehei, Myceliophthora thermophila, Neurospora crassa, Scytalidium thermophilum*, or *Thielavia terrestris* whole cellulase. In another aspect, the whole cellulase preparation a *Trichoderma harzianum, Trichoderma koningii, Trichoderma longibrachiatum, Trichoderma reesei* e.g., RL-P37 (Sheir-Neiss et al., Appl. Microbiol. Biotechnology, 20 (1984) pp. 46-53; Montenecourt B. S., Can., 1-20, 1987), QM9414 (ATCC No. 26921), NRRL 15709, ATCC 13631, 56764, 56466, 56767, or *Trichoderma viride* e.g., ATCC 32098 and 32086, whole cellulase. In some embodiments, the whole cellulase preparation is a *Trichoderma reesei* RutC30 whole cellulase, which is available from the American Type Culture Collection as *Trichoderma reesei* ATCC 56765.

Examples of commercial cellulase preparations suitable for use in the present disclosure include, for example, CELLUCLAST™ (available from Novozymes A/S) and LAMINEX™ IndiAge™ and Primafast™ LAMINEX BG enzyme, ACCELLERASE™ 100 and ACCELLERASE™ 1500 (available Genencor Division, Danisco US. Inc.)

In the present disclosure, the whole cellulase preparation can be from any microorganism cultivation method known in the art resulting in the expression of enzymes capable of hydrolyzing a cellulosic material. Fermentation can include shake flask cultivation, small- or large-scale fermentation, such as continuous, batch, fed-batch, or solid state fermentations in laboratory or industrial fermenters performed in a suitable medium and under conditions allowing the cellulase to be expressed or isolated.

Generally, the microorganism is cultivated in a cell culture medium suitable for production of enzymes capable of hydrolyzing a cellulosic material. The cultivation takes place in a suitable nutrient medium comprising carbon and nitrogen sources and inorganic salts, using procedures known in the art. Suitable culture media, temperature ranges and other conditions suitable for growth and cellulase production are known in the art. As a non-limiting example, the normal temperature range for the production of cellulases by *Trichoderma reesei* is 24° C. to 28° C.

Generally, the whole cellulase preparation is used as is produced by fermentation with no or minimal recovery and/or purification. For example, once cellulases are secreted by a cell into the cell culture medium, the cell culture medium containing the cellulases can be used. In some embodiments the whole cellulase preparation comprises the unfractionated contents of fermentation material, including cell culture medium, extracellular enzymes and cells. Alternatively, the whole cellulase preparation can be processed by any convenient method, e.g., by precipitation, centrifugation, affinity, filtration or any other method known in the art. In some embodiments, the whole cellulase preparation can be concentrated, for example, and then used without further purification. In some embodiments the whole cellulase preparation comprises chemical agents that decrease cell viability or kills the cells. In some embodiments, the cells are lysed or permeabilized using methods known in the art.

III. Molecular Biology

In one embodiment this disclosure provides for the expression of variant cbh2 genes under control of a promoter functional in a filamentous fungus. Therefore, this disclosure relies on routine techniques in the field of recombinant genetics (See, e.g., Sambrook et al., Molecular Cloning, A Laboratory Manual, 2nd ed., 1989; Kriegler, Gene Transfer and Expression: A Laboratory Manual, 1990; and Ausubel et al., eds., CURRENT PROTOCOLS IN MOLECULAR BIOLOGY, Greene Publishing and Wiley-Interscience, New York, 1994).

Methods of Mutating cbh2 Nucleic Acid Sequences

Any method known in the art that can introduce mutations is contemplated by the present disclosure.

The present disclosure relates to the expression, purification and/or isolation and use of variant CBH2. These enzymes are preferably prepared by recombinant methods utilizing the cbh2 gene from *H. jecorina*. The fermentation broth may be used with or without purification.

After the isolation and cloning of the cbh2 gene from *H. jecorina*, other methods known in the art, such as site directed mutagenesis, are used to make the substitutions, additions or deletions that correspond to substituted amino acids in the expressed CBH2 variant. Again, site directed mutagenesis and other methods of incorporating amino acid changes in expressed proteins at the DNA level are known in the art (Sambrook et al., supra; and Ausubel et al., supra).

DNA encoding an amino acid sequence variant of the *H. jecorina* CBH2 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *H. jecorina* CBH2.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *H. jecorina* CBH2. See Higuchi, in PCR Protocols, pp. 177-183 (Academic Press, 1990); and Vallette et al., Nuc. Acids Res. 17:723-733 (1989). See, also, for example Cadwell et al., PCR Methods and Applications, Vol 2, 28-33 (1992). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a variant CBH2 can be determined, and a nucleic acid sequence encoding such amino acid sequence variant can be generated synthetically.

The variant CBH2(s) so prepared may be subjected to further modifications, oftentimes depending on the intended use of the cellulase. Such modifications may involve further alteration of the amino acid sequence, fusion to heterologous polypeptide(s) and/or covalent modifications.

IV. cbh2 Nucleic Acids and CBH2 Polypeptides

A. Variant cbh2-Type Nucleic Acids

The nucleic acid sequence for the wild type cbh2 is shown in SEQ ID NO:1. The disclosure encompasses a nucleic acid molecule encoding the variant cellulases described herein. The nucleic acid may be a DNA molecule.

After DNA sequences that encode the CBH2 variants have been cloned into DNA constructs, the DNA is used to transform microorganisms. The microorganism to be transformed for the purpose of expressing a variant CBH2 according to the present disclosure may advantageously comprise a strain derived from *Trichoderma* sp. Thus, a preferred mode for preparing variant CBH2 cellulases according to the present disclosure comprises transforming a *Trichoderma* sp. host cell with a DNA construct comprising at least a fragment of DNA encoding a portion or all of the variant CBH2. The DNA construct will generally be functionally attached to a promoter. The transformed host cell is then grown under conditions so as to express the desired protein. Subsequently, the desired protein product may be purified to substantial homogeneity.

However, it may in fact be that the best expression vehicle for a given DNA encoding a variant CBH2 may differ from *H. jecorina*. Thus, it may be that it will be most advantageous to express a protein in a transformation host that bears phylogenetic similarity to the source organism for the variant CBH2. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of an *Aspergillus* spp. expression system is provided for illustrative purposes only and as one option for expressing the variant CBH2 of the disclosure. One of skill in the art, however, may be inclined to express the DNA encoding variant CBH2 in a different host cell if appropriate and it should be understood that the source of the variant CBH2 should be considered in determining the optimal expression host. Additionally, the skilled worker in the field will be capable of selecting the best expression system for a particular gene through routine techniques utilizing the tools available in the art.

B. Variant CBH2 Polypeptides

The variant CBH2's of this disclosure have amino acid sequences that are derived from the amino acid sequence of a precursor CBH2. The amino acid sequence of the CBH2 variant differs from the precursor CBH2 amino acid sequence by the substitution, deletion or insertion of one or more amino acids of the precursor amino acid sequence. In a preferred embodiment, the precursor CBH2 is *Hypocrea jecorina* CBH2. The mature amino acid sequence of *H. jecorina* CBH2 is shown in SEQ ID NO:3. Thus, this disclosure is directed to CBH2 variants which contain amino acid residues at positions which are equivalent to the particular identified residue in *H. jecorina* CBH2. A residue (amino acid) of an CBH2 homolog is equivalent to a residue of *Hypocrea jecorina* CBH2 if it is either homologous (i.e., corresponding in position in either primary or tertiary structure) or is functionally analogous to a specific residue or portion of that residue in *Hypocrea jecorina* CBH2 (i.e., having the same or similar functional capacity to combine, react, or interact chemically or structurally). As used herein, numbering is intended to correspond to that of the mature CBH2 amino acid sequence (SEQ ID NO:3).

Alignment of amino acid sequences to determine homology is preferably determined by using a "sequence comparison algorithm." Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. Visual inspection may utilize graphics packages such as, for example, MOE by Chemical Computing Group, Montreal Canada.

An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M'S, N'-4, and a comparison of both strands.

The BLAST algorithm then performs a statistical analysis of the similarity between two sequences (see, e.g., Karlin & Altschul, Proc. Nat'l. Acad. Sci. USA 90:5873-5787 (1993)).

One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

For purposes of the present disclosure, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polynucleotide sequence comparison: GAP creation penalty of 5.0 and GAP extension penalty of 0.3.

A structural alignment between a *T. reesei* CBH2 and other cellulases may be used to identify equivalent/corresponding positions in other cellulases having a moderate to high degree of homology, e.g., about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or even 99%, with *T. reesei* CBH2 (SEQ ID NO: 3). One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., FEBS Letters, 224:149-155, 1987) and reverse threading (Huber and Torda, Protein Science, 7:142-149, 1998).

An exemplary alignment of the mature form of various reference cellulases is provided as FIG. 3. The reference cellulases include: *Hypocrea jecorina* (also known as *T. reesei*) CBH2 (SEQ ID NO:3), *Hypocrea koningii* CBH2 (SEQ ID NO:4), *Humicola insolens* CBH2 (SEQ ID NO:5), *Acremonium cellulolyticus* CBH2 (SEQ ID NO:6), *Agaricus bisporus* CBH2 (SEQ ID NO:7), *Fusarium osysporum* EG (SEQ ID NO:8), *Phanerochaete chrysosporium* CBH2 (SEQ ID NO:9), *Talaromyces emersonii* CBH2 (SEQ ID NO:10), *Thermobifida fusca* 6B/E3 CBH2 (SEQ ID NO:11), *Thermobifida fusca* 6A/E2 EG (SEQ ID NO:12), and *Cellulomonas fimi* CenA EG (SEQ ID NO:13). Sequences were aligned using the ClustalW and the MUSCLE multiple sequence alignment algorithms. A matrix showing the percent identity of cellulases of the sequence alignment of FIG. 3 is provided in Table 1.

TABLE 1

Cellulase Percent Identity Matrix*

| Percent_ID | 3 | 4 | 5 | 6 | 7 | 8 | 9 | 10 | 11 | 12 | 13 |
|---|---|---|---|---|---|---|---|---|---|---|---|
| 3 | 100 | 95.5 | 62.3 | 64.7 | 59.6 | 63.1 | 55.4 | 63.4 | 31.9 | 13.5 | 27 |
| 4 | 95.5 | 100 | 61.6 | 64 | 59.1 | 63.6 | 54.7 | 63 | 32.9 | 13.5 | 26.8 |
| 5 | 62.3 | 61.6 | 100 | 59.1 | 57.6 | 61.3 | 54 | 58.8 | 31.9 | 15.9 | 26.6 |
| 6 | 64.7 | 64 | 59.1 | 100 | 58.6 | 56.4 | 54 | 72.6 | 32.8 | 13.5 | 29.2 |
| 7 | 59.6 | 59.1 | 57.6 | 58.6 | 100 | 55.8 | 69.1 | 58.1 | 34.9 | 17.5 | 27.6 |
| 8 | 63.1 | 63.6 | 61.3 | 56.4 | 55.8 | 100 | 48.7 | 54.8 | 31.1 | 13.9 | 25.2 |
| 9 | 55.4 | 54.7 | 54 | 54 | 69.1 | 48.7 | 100 | 52.6 | 32.4 | 15.4 | 25.6 |
| 10 | 63.4 | 63 | 58.8 | 72.6 | 58.1 | 54.8 | 52.6 | 100 | 33.9 | 13.2 | 27.3 |
| 11 | 31.9 | 32.9 | 31.9 | 32.8 | 34.9 | 31.1 | 32.4 | 33.9 | 100 | 15.9 | 36.3 |
| 12 | 13.5 | 13.5 | 15.9 | 13.5 | 17.5 | 13.9 | 15.4 | 13.2 | 15.9 | 100 | 12.8 |
| 13 | 27 | 26.8 | 26.6 | 29.2 | 27.6 | 25.2 | 25.6 | 27.3 | 36.3 | 12.8 | 100 |

*Numbers in the top row and left column correspond to the SEQ ID NOS of the aligned sequences of FIG. 3.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

V. Expression of Recombinant CBH2 Variants

The methods of the disclosure rely on the use cells to express variant CBH2, with no particular method of CBH2 expression required. The variant CBH2 is preferably secreted from the cells. The disclosure provides host cells which have been transduced, transformed or transfected with an expression vector comprising a variant CBH2-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding variant CBH2, such that variant CBH2 is expressed in the cell line.

A. Nucleic Acid Constructs/Expression Vectors.

Natural or synthetic polynucleotide fragments encoding variant CBH2 ("CBH2-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of variant CBH2. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces,* 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for variant CBH2 may be produced by introducing a heterologous nucleic acid construct comprising the variant CBH2 coding sequence into the cells of a selected strain of the filamentous fungi.

Once the desired form of a variant cbh2 nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant cbh2 coding sequence may be inserted into a suitable vector according to well-known recombinant techniques and used to transform filamentous fungi capable of CBH2 expression. Due to the inherent degeneracy of the genetic code, other nucleic acid sequences which encode substantially the same or a functionally equivalent amino acid sequence may be used to clone and express variant CBH2. Therefore it is appreciated that such substitutions in the coding region fall within the sequence variants covered by the present disclosure. Any and all of these sequence variants can be utilized in the same way as described herein for a parent CBH2-encoding nucleic acid sequence.

The present disclosure also includes recombinant nucleic acid constructs comprising one or more of the variant CBH2-encoding nucleic acid sequences as described above. The constructs comprise a vector, such as a plasmid or viral vector, into which a sequence of the disclosure has been inserted, in a forward or reverse orientation.

Heterologous nucleic acid constructs may include the coding sequence for variant cbh2. (i) in isolation; (ii) in combination with additional coding sequences; such as fusion protein or signal peptide coding sequences, where the cbh2 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the cbh2 coding sequence is a heterologous gene.

In one aspect of the present disclosure, a heterologous nucleic acid construct is employed to transfer a variant CBH2-encoding nucleic acid sequence into a cell in vitro, with established filamentous fungal and yeast lines preferred. For long-term, production of variant CBH2, stable expression is preferred. It follows that any method effective to generate stable transformants may be used in practicing the disclosure.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1.alpha. promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a variant CBH2 polypeptide. Such linkage comprises positioning of the promoter with respect to the initiation codon of the DNA sequence encoding the variant CBH2 polypeptide in the disclosed expression vectors. The promoter sequence contains transcription and translation control sequence which mediate the expression of the variant CBH2 polypeptide. Examples include the promoters from the *Aspergillus niger, A. awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* (*T. reesei*) cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from *A. nidulans*, which make it possible to replicate in *A. niger*.

The practice of the present disclosure will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, Animal Cell Culture, 1987; Ausubel, et al., 1993; and Coligan et al., Current Protocols in Immunology, 1991.

B. Host Cells and Culture Conditions For CBH2 Production (i) Filamentous Fungi

Thus, the present disclosure provides filamentous fungi comprising cells which have been modified, selected and cultured in a manner effective to result in variant CBH2 production or expression relative to the corresponding non-transformed parental fungi.

Examples of species of parental filamentous fungi that may be treated and/or modified for variant CBH2 expression include, but are not limited to *Trichoderma*, e.g., *Trichoderma reesei*, *Trichoderma longibrachiatum*, *Trichoderma viride*, *Trichoderma koningii*; *Penicillium* sp., *Humicola* sp., including *Humicola insolens*; *Aspergillus* sp., *Chrysosporium* sp., *Fusarium* sp., *Hypocrea* sp., and *Emericella* sp.

CBH2 expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28.degree. C. in shaker cultures or fermenters until desired levels of CBH2 expression are achieved.

Preferred culture conditions for a given filamentous fungus may be found in the scientific literature and/or from the source of the fungi such as the American Type Culture Collection (ATCC; www.atcc.org/). After fungal growth has been established, the cells are exposed to conditions effective to cause or permit the expression of variant CBH2.

In cases where a CBH2 coding sequence is under the control of an inducible promoter, the inducing agent, e.g., a sugar, metal salt or antibiotics, is added to the medium at a concentration effective to induce CBH2 expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al., Curr. Genet (2002) 41: 89-98). Other strains of *Aspergillus niger* var *awamori* such as GCDAP3, GCDAP4 and GAP3-4 are known (Ward et al., Appl. Microbiol. Biotechnol. 39:738-743, 1993).

In another embodiment, the strain comprises *Trichoderma reesei*, which is a useful strain for obtaining overexpressed protein. For example, RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH2.

Where it is desired to obtain the variant CBH2 in the absence of potentially detrimental native cellulolytic activity, it is useful to obtain a *Trichoderma* host cell strain which has had one or more cellulase genes deleted prior to introduction of a DNA construct or plasmid containing the DNA fragment encoding the variant CBH2. Such strains may be prepared by the method disclosed in U.S. Pat. No. 5,246,853 and WO 92/06209, which disclosures are hereby incorporated by reference. By expressing a variant CBH2 cellulase in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding EG III and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of an *Aspergillus* sp. gene may be used which if lacking in the host strain results in the host strain displaying an auxotrophic phenotype. Similarly, selectable markers exist for *Trichoderma* sp.

In one embodiment, a pyrG– derivative strain of *Aspergillus* sp. is transformed with a functional pyrG gene, which thus provides a selectable marker for transformation. A pyrG– derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG-derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, Curr. Genet. 19:359-365 (1991), and van Hartingsveldt et al., (1986) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker.

In a second embodiment, a pyr4.– derivative strain of *Hyprocrea* sp. (*Hyprocrea* sp. (*Trichoderma* sp.)) is transformed with a functional pyr4 gene, which thus provides a selectable marker for transformation. A pyr4.sup.– derivative strain may be obtained by selection of *Hyprocrea* sp. (*Trichoderma* sp.) strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4.sup.– derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, 1991). Selection of derivative strains is easily performed using the FOA resistance technique referred to above, and thus, the pyr4 gene is preferably employed as a selectable marker.

To transform pyrG.– *Aspergillus* sp. or pyr4– *Hyprocrea* sp. (*Trichoderma* sp.) so as to be lacking in the ability to express one or more cellulase genes, a single DNA fragment comprising a disrupted or deleted cellulase gene is then isolated from the deletion plasmid and used to transform an appropriate pyr– *Aspergillus* or pyr– *Trichoderma* host. Transformants are then identified and selected based on their ability to express the pyrG or pyr4, respectively, gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the appropriate pyr selectable markers.

Although the specific plasmid vectors described above relate to preparation of pyr-transformants, the present disclosure is not limited to these vectors. Various genes can be deleted and replaced in the *Aspergillus* sp. or *Hyprocrea* sp. (*Trichoderma* sp.) strain using the above techniques. In addition, any available selectable markers can be used, as discussed above. In fact, any host, e.g., *Aspergillus* sp. or *Hyprocrea* sp., gene that has been cloned, and thus identified, can be deleted from the genome using the above-described strategy.

As stated above, the host strains used may be derivatives of *Hyprocrea* sp. (*Trichoderma* sp.) that lack or have a nonfunctional gene or genes corresponding to the selectable marker chosen. For example, if the selectable marker of pyrG is chosen for *Aspergillus* sp., then a specific pyrG– derivative strain is used as a recipient in the transformation procedure.

Also, for example, if the selectable marker of pyr4 is chosen for a *Hyprocrea* sp., then a specific pyr4-derivative strain is used as a recipient in the transformation procedure. Similarly, selectable markers comprising *Hyprocrea* sp. (*Trichoderma* sp.) genes equivalent to the *Aspergillus nidulans* genes amdS, argB, trpC, niaD may be used. The corresponding recipient strain must therefore be a derivative strain such as argB-, trpC-, niaD-, respectively.

DNA encoding the CBH2 variant is then prepared for insertion into an appropriate microorganism. According to the present disclosure, DNA encoding a CBH2 variant comprises the DNA necessary to encode for a protein that has functional cellulolytic activity. The DNA fragment encoding the CBH2 variant may be functionally attached to a fungal promoter sequence, for example, the promoter of the glaA gene in *Aspergillus* or the promoter of the cbh1 or egl1 genes in *Trichoderma*.

It is also contemplated that more than one copy of DNA encoding a CBH2 variant may be recombined into the strain to facilitate overexpression. The DNA encoding the CBH2 variant may be prepared by the construction of an expression vector carrying the DNA encoding the variant. The expression vector carrying the inserted DNA fragment encoding the CBH2 variant may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker may also be contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences.

For example, in *Aspergillus*, pRAX is such a general-purpose expression vector. Genes or part thereof can be inserted downstream of the strong glaa promoter.

For example, in *Hypocrea*, pTEX is such a general-purpose expression vector. Genes or part thereof can be inserted downstream of the strong cbh1 promoter.

In the vector, the DNA sequence encoding the CBH2 variant of the present disclosure should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the CBH2 variant. The DNA encoding the signal sequence is preferably that which is naturally associated with the gene to be expressed, however the signal sequence from any suitable source, for example an exo-cellobiohydrolase or endoglucanase from *Trichoderma*, is contemplated in the present disclosure.

The procedures used to ligate the DNA sequences coding for the variant CBH2 of the present disclosure with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Hyprocrea* sp. (*Trichoderma* sp.) is very low. Accordingly, uptake of the desired DNA sequence, gene or gene fragment is at best minimal. There are a number of methods to increase the permeability of the *Hyprocrea* sp. (*Trichoderma* sp.) cell wall in the derivative strain (i.e., lacking a functional gene corresponding to the used selectable marker) prior to the transformation process.

The preferred method in the present disclosure to prepare *Aspergillus* sp. or *Hyprocrea* sp. (*Trichoderma* sp.) for transformation involves the preparation of protoplasts from fungal mycelium. See Campbell et al. Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host strain, (*Aspergillus* sp. or *Hyprocrea* sp. (*Trichoderma* sp.), is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the host cell, by way of example either *Aspergillus* sp. or *Hyprocrea* sp. strain, and the plasmid DNA is transferred to the nucleus. This fusion frequently leaves multiple copies of the plasmid DNA integrated into the host chromosome.

Usually a suspension containing the *Aspergillus* sp. protoplasts or cells that have been subjected to a permeability treatment at a density of $10^5$ to $10^6$/mL, preferably $2 \times 10^5$/mL are used in transformation. Similarly, a suspension containing the *Hyprocrea* sp. (*Trichoderma* sp.) protoplasts or cells that have been subjected to a permeability treatment at a density of $10^8$ to $10^9$/mL, preferably $2 \times 10^8$/mL are used in transformation. A volume of 100.mu.L of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0.degree. C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present disclosure that is suitable to grow the desired transformants. However, if Pyr.sup.+ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and, in *Trichoderma*, for example, the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the CBH2 variant(s) are recovered in active form from the host cell after growth in liquid media as a result of the appropriate post translational processing of the CBH2 variant.

(ii) Yeast

The present disclosure also contemplates the use of yeast as a host cell for CBH2 production. Several other genes encoding hydrolytic enzymes have been expressed in various strains of the yeast *S. cerevisiae*. These include sequences encoding for two endoglucanases (Penttila et al., Yeast vol. 3, pp 175-185, 1987), two cellobiohydrolases (Penttila et al., Gene, 63: 103-112, 1988) and one beta-glucosidase from *Trichoderma reesei* (Cummings and Fowler, Curr. Genet. 29:227-233, 1996), a xylanase from *Aureobasidlium pullulans* (Li and Ljungdahl, Appl. Environ. Microbiol. 62, no. 1, pp. 209-213, 1996), an alpha-amylase from wheat (Rothstein et al., Gene 55:353-356, 1987), etc. In addition, a cellulase gene cassette encoding the Butyrivibrio fibrisolvens endo-[beta]-1,4-glucanase (END1), *Phanerochaete chrysosporium* cellobiohydrolase (CBH1), the *Ruminococcus flavefaciens* cellodextrinase (CEL1) and the Endomyces fibrilizer cellobiase (Bgl1) was successfully expressed in a laboratory strain of *S. cerevisiae* (Van Rensburg et al., Yeast, vol. 14, pp. 67-76, 1998).

C. Introduction of a CBH2-Encoding Nucleic Acid Sequence into Host Cells.

The disclosure further provides cells and cell compositions which have been genetically modified to comprise an exogenously provided variant CBH2-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

The methods of transformation of the present disclosure may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

Other methods for introducing a heterologous nucleic acid construct (expression vector) into filamentous fungi (e.g., *H. jecorina*) include, but are not limited to the use of a particle or gene gun, permeabilization of filamentous fungi cells walls prior to the transformation process (e.g., by use of high concentrations of alkali, e.g., 0.05 M to 0.4 M $CaCl_2$ or lithium acetate), protoplast fusion or *Agrobacterium* mediated transformation. An exemplary method for transformation of filamentous fungi by treatment of protoplasts or spheroplasts with polyethylene glycol and $CaCl_2$ is described in Campbell, E. I. et al., Curr. Genet. 16:53-56, 1989 and Penttila, M. et al., Gene, 63:11-22, 1988.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

In addition, heterologous nucleic acid constructs comprising a variant CBH2-encoding nucleic acid sequence can be transcribed in vitro, and the resulting RNA introduced into the host cell by well-known methods, e.g., by injection.

The disclosure further includes novel and useful transformants of filamentous fungi such as *H. jecorina* and *A. niger* for use in producing fungal cellulase compositions. The disclosure includes transformants of filamentous fungi especially fungi comprising the variant CBH2 coding sequence, or deletion of the endogenous cbh coding sequence.

Following introduction of a heterologous nucleic acid construct comprising the coding sequence for a variant cbh2, the genetically modified cells can be cultured in conventional nutrient media modified as appropriate for activating promoters, selecting transformants or amplifying expression of a variant CBH2-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the variant CBH2-encoding nucleic acid sequence found in the heterologous nucleic acid construct.

The disclosure further includes novel and useful transformants of filamentous fungi such as *H. jecorina* for use in producing fungal cellulase compositions. *Aspergillus niger* may also be used in producing the variant CBH2. The disclosure includes transformants of filamentous fungi especially fungi comprising the variant cbh 2 coding sequence, or deletion of the endogenous cbh2 coding sequence.

Stable transformants of filamentous fungi can generally be distinguished from unstable transformants by their faster growth rate and, in *Trichoderma*, for example, the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VI. Isolation and Purification of Recombinant CBH2 Protein

In general, a variant CBH2 protein produced in cell culture is secreted into the medium and may be purified or isolated, e.g., by removing unwanted components from the cell culture medium. However, in some cases, a variant CBH2 protein may be produced in a cellular form necessitating recovery from a cell lysate. In such cases the variant CBH2 protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatographic methods (Goyal et al., Bioresource Technol. 36:37-50, 1991; Fliess et al., Eur. J. Appl. Microbiol. Biotechnol. 17:314-318, 1983; Bhikhabhai et al., J. Appl. Biochem. 6:336-345, 1984; Ellouz et al., J. Chromatography 396:307-317, 1987), including ion-exchange using materials with high resolution power (Medve et al., J. Chromatography A 808:153-165, 1998), hydrophobic interaction chromatography (Tomaz and Queiroz, J. Chromatography A 865:123-128, 1999), and two-phase partitioning (Brumbauer, et al., Bioseparation 7:287-295, 1999).

Typically, the variant CBH2 protein is fractionated to segregate proteins having selected properties, such as binding affinity to particular binding agents, e.g., antibodies or receptors; or which have a selected molecular weight range, or range of isoelectric points.

Once expression of a given variant CBH2 protein is achieved, the CBH2 protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods in Enzymology, vol. 182, no. 57, pp. 779, 1990; Scopes, Methods Enzymol. 90: 479-91, 1982. The purification step(s) selected will depend, e.g., on the nature of the production process used and the particular protein produced.

VII. Utility of CBH2 and CBH2

It can be appreciated that the variant cbh nucleic acids, the variant CBH2 protein and compositions comprising variant CBH2 protein activity find utility in a wide variety applications, some of which are described below.

New and improved cellulase compositions that comprise varying amounts BG-type, EG-type and variant CBH-type cellulases find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

In one approach, the cellulase of the disclosure finds utility in detergent compositions or in the treatment of fabrics to improve the feel and appearance.

Since the rate of hydrolysis of cellulosic products may be increased by using a transformant having at least one additional copy of the cbh gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the variant CBH type cellulase of the disclosure finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive variant CBH and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

The methods of the present disclosure can be used in the production of monosaccharides, disaccharides, and polysaccharides as chemical or fermentation feedstocks for microorganism for the production of organic products, chemicals and fuels, plastics, and other products or intermediates. In particular, the value of processing residues (dried distillers grain, spent grains from brewing, sugarcane bagasse, etc.) can be increased by partial or complete solubilization of cellulose or hemicellulose. In addition to ethanol, some chemicals that can be produced from cellulose and hemicellulose include, acetone, acetate, glycine, lysine, organic acids (e.g., lactic acid), 1,3-propanediol, butanediol, glycerol, ethylene glycol, furfural, polyhydroxyalkanoates, cis, cis-muconic acid, animal feed and xylose.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petrochemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase finds use in the hydrolysis of cellulose to its sugar components. In one embodiment, a variant cellobiohydrolase is added to the biomass prior to the addition of a fermentative organism. In a second embodiment, a variant cellobiohydrolase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

The major product of CBH2 action on cellulose is cellobiose which is available for conversion to glucose by BG activity (for instance in a fungal cellulase product). Either by the pretreatment of the cellulosic biomass or by the enzymatic action on the biomass, other sugars, in addition to glucose and cellobiose, can be made available from the biomass. The hemi-cellulose content of the biomass can be converted (by hemi-cellulases) to sugars such as xylose, galactose, mannose and arabinose. Thus, in a biomass conversion process, enzymatic saccharification can produce sugars that are made available for biological or chemical conversions to other intermediates or end-products. Therefore, the sugars generated from biomass find use in a variety of processes in addition to the generation of ethanol. Examples of such conversions are fermentation of glucose to ethanol (as reviewed by M. E. Himmel et al. pp 2-45, in "Fuels and Chemicals from Biomass", ACS Symposium Series 666, ed B. C. Saha and J. Woodward, 1997) and other biological conversions of glucose to 2,5-diketo-D-gluconate (U.S. Pat. No. 6,599,722), lactic acid (R. Datta and S-P. Tsai pp 224-236, ibid), succinate (R. R. Gokarn, M. A. Eiteman and J. Sridhar pp 237-263, ibid), 1,3-propanediol (A-P. Zheng, H. Biebl and W-D. Deckwer pp 264-279, ibid), 2,3-butanediol (C. S. Gong, N. Cao and G. T. Tsao pp 280-293, ibid), and the chemical and biological conversions of xylose to xylitol (B. C. Saha and R. J. Bothast pp 307-319, ibid). See also, for example, WO 98/21339.

The detergent compositions of this disclosure may employ besides the cellulase composition (irrespective of the cellobiohydrolase content, i.e., cellobiohydrolase-free, substantially cellobiohydrolase-free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH2 type components," which is incorporated herein by reference.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

In addition the variant CBH2 nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knockout (reverse genetics, targeted knock-out, viral induced gene silencing (VIGS, see Baulcombe, 100 Years of Virology, Calisher and Horzinek eds., Springer-Verlag, New York, N.Y. 15:189-201, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

EXPERIMENTAL

The present disclosure is described in further detail in the following Examples which are not in any way intended to limit the scope of the disclosure as claimed. The attached Figures are meant to be considered as integral parts of the specification and description of the disclosure. The following Examples are offered to illustrate, but not to limit the claimed disclosure In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minuteo); $H_2O$ (water); $dH_2O$ (deionized water); HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); CNPG (chloro-nitro-phenyl-beta-D-glucoside); CNP (2-chloro-4-nitrophenol); APB (acid-pretreated bagasse); PASC (phosphoric acid swollen cellulose) PCS (acid-pretreated corn stover); Pi or PI (performance index); PAGE (polyacrylamide gel electrophoresis); PCR (polymerase chain reaction); RT-PCR (reverse transcription PCR); and HPLC (high pressure liquid chromatography).

Example 1

Chemical Modification of a *Trichoderma* sp. Cellulase Preparation and Assays for Testing CBH2 Variants This Example describes the treatment of a commercial *Trichoderma* sp. cellulase preparation (LAMINEX BG enzyme complex (Genencor Division, Danisco US, Inc.) with succinic anhydride to acetylate the lysine residues. Acetylation of the lysine residues of the LAMINEX BG enzyme complex alters the net charge of the proteins (e.g., increased negative charge). Other similar chemical modifications can be used to also convert the positive charge of the lysine to a negative charged group (for example with acetoxysuccinic anhydride, maleic anhydride, tartaric anhydride and phthalic anhydride treatment) or even to two negative charges (for example with trimellitic anhydride, cis-aconitic anhydride and 4-nitrophthalic anhydride treatment). Other chemical modifications can be used to remove the positive charges of lysine residues resulting in a noncharged residue (for example acetic anhydride, butyric anhydride, isobutyric anhydride, hexanoic anhydride, valeric anhydride, isovaleric anhydride and pivalic anhydride treatment).

Lysine residues on a cellulase preparation were modified using succinic anhydride, using a variation of published methods (Lundblad, Chemical Reagents for Protein Modification, Editor: R. Lundblad, $3^{rd}$ Edition CRC press, 1984). For this reaction, a 236 mg sample of LAMINEX BG enzyme complex was prepared in 1 mL of 500 mM HEPES buffer pH 8. A succinic anhydride (Aldrich) solution was prepared by dissolving the powder in DMSO to a 500 mg/mL final concentration before addition of the enzyme complex. An aliquot of succinic anhydride was added such that a ratio of >1:100 lysine to succinic acid was achieved in the reaction tube. Another reaction tube was set up with DMSO and enzyme only, using similar volumes, to serve as the unmodified protein control. The tubes were vortexed and left at room temp overnight. The following day, a 1:10 volume of 1M glycine pH 3 was added to each tube to quench the succinic anhydride reaction.

Chemical modification was confirmed by comparing modified and unmodified proteins on native gels. Aliquots from each reaction (chemically-modified and unmodified) were analyzed on gradient 8-25%, native gels run at pH 8.8 at 100 volts (Phast System gels, GE Healthcare). Proteins were visualized after Coomassie blue staining of the gel, to confirm that the modification was successful. Staining revealed shifts in protein band migration, confirming the changes in charge of the various protein components of the cellulase preparation. Modified samples of *Trichoderma* sp. cellulase preparation were more negativity charged than unmodified samples.

To isolate the modified and unmodified (control) proteins, 80 μl aliquots of each sample were desalted using spin desalt columns (Pierce). The absorbance at 280 nm of desalted samples (including the control without modification) was measured using a NanoDrop™ spectrophotometer (Thermo), in duplicates after a 1:10 sample dilution to determine the total protein concentration of the samples.

Zeta Potential Determinations

This Example describes determining the zeta potential of an enzyme and a substrate. The presence of a charge on the surface of a particle influences the distribution of ions in the surrounding interfacial region. The result is an increased concentration of counter ions of opposite charge to that of the particle near the particle surface. As one moves away from the particle surface, the heterogeneous distribution of ions will eventually become homogeneous. The distance at which a homogenous distribution is obtained is called the Debye length ($1/\kappa$) or screening distance, and is dependent upon the ionic strength as shown in the expression below, where $\in_0$ is the permittivity of free space ($8.854\times10^{-12}$ F m$^{-1}$), $\in_r$ is the permittivity of the liquid, k is the Boltzmann constant ($1.38\times 10^{-23}$ J K$^{-1}$), T is the temperature in Kelvin, e is the electronic charge ($1.6022\times10^{-19}$ C), I is the molar ionic strength, and NA is Avogadro's constant ($6.022\times10^{23}$ mol$^{-1}$).

$$\text{Debye Length} = \frac{1}{k} = \sqrt{\frac{e_0 e_r kT}{NAe^2 2I}} \quad (0.1)$$

The molar ionic strength can be calculated from the following equation, where $C_i$ is the ionic species concentration and $Z_i$ is the valency.

$$I = \frac{1}{2}åC_i Z_i^2 \quad (0.2)$$

For water at 298 K, the Debye length expression reduces to the following form.

$$k^{-1} = 0.304(I^{-0.5}) \quad (0.3)$$

The liquid layer surrounding the particle exists as two parts; an inner region (Stern layer) where the ions are strongly bound and an outer (diffuse) region where they are less firmly associated. Within the diffuse layer there is a boundary inside which the ions and particles form a stable entity. When a particle moves, ions within this boundary move with it. Those ions beyond the boundary do not travel with the particle. The electric potential at this boundary, also called the surface of hydrodynamic shear, is defined as the zeta potential.

In electrophoretic light scattering, the zeta potential z is calculated from the measured electrophoretic mobility u using the Henry equation shown below, where $\in$ is the dielectric constant, h is the solution viscosity, $\kappa$ is the inverse Debye length, a is the particle radius, and f(ka) is the Henry function.

$$u = \frac{2ez}{3h} f(ka) \quad (0.4)$$

The units of $\kappa$ are reciprocal length, with $1/\kappa$ being the "thickness" of the electrical double layer (Debye length). The parameter a refers to the radius of the particle, and therefore, $\kappa a$ is the ratio of the particle radius to the electrical double layer thickness. The Henry function, f(ka) depends on particle shape, but is known for a sphere. In the expression above it ranges from f(0)=1 (Hückel limit) to f(¥)=1.5 (Smoluchowski limit). For small particles such as proteins in a low dielectric (or low ionic strength) medium, the Hückel limit of f(ka)=1 is the more appropriate model.

Zeta potentials of proteins were measured with the Zetasizer NS (Malvern Instruments, UK) according to the principle outlined above. Zeta potentials of BMI-stained fabrics were measured with the SurPass (Anton-Paar, Austria) using the streaming potential implementation of the above principle. From the definition of surface charge, usually expressed in Coulombs:

$$q_s = 4pe_o e_r a(1+ka)z \quad (0.5)$$

This can also be expressed as a net charge z multiplied by the elementary charge e $1.6*10$-$19$ C:

$$q_s = ze \quad (0.6)$$

Therefore the expected change in zeta potential due to a net charge increment is given by:

$$\frac{Dz}{Dz} = \frac{e}{4pe_o e_r a(1+ka)} \quad (0.7)$$

It is also possible to measure zeta potentials using a native gel technique (Sparks et al., Journal of Lipid Research, 33:123-130, 1992) as described in Example 1. Electrophoretic mobility measured with native gels is usually less than in solution due to retardation caused by the gel matrix. Zeta potentials calculated this way are usually lower compared to solution-based methods. We therefore refer to them as apparent zeta potentials when obtained via the native gel technique.

The effective charge in a given formulation is enumerated as its zeta potential. The use of zeta potential as a common charge scale allows comparison of enzyme variants having different folds (e.g., serine proteases, metalloproteases, etc.), as well as interactions with different substrates (e.g., BMI microswatch) under the conditions of interest (e.g., AATCC HDL detergent). Although zeta potential is preferred for comparing different protein folds, electrophoretic mobilities or measured charges also provide an absolute scale and are adequate for comparisons. BMI performance as a function of enzyme zeta potential is well described by a standard normal distribution, indicated by the solid line, with a mean μ equal to −9.68 mV, standard deviation σ of 11.39 mV and peak value of 0.4056 [A600-background]. This distribution is indicated in standard reduced coordinates by the BMI activity divided by the peak value on the right Y-axis as a function of the Z score on the top X-axis. The Z score is defined as usual as (X−μ)/σ where X in this case is zeta potential.

TABLE 1-1

BMI Microswatch Activity of Proteases

| Performance Level | Z Score | Zeta Potential $\zeta$ Window* For BMI Microswatch Activity |
|---|---|---|
| 90% | ±0.46 | $-14.92 < \zeta < -4.44$ |
| 80% | ±0.65 | $-17.08 < \zeta < -2.28$ |
| 70% | ±0.84 | $-19.25 < \zeta < -0.11$ |
| 60% | ±1.00 | $-21.07 < \zeta < +1.71$ |
| 50% | ±1.18 | $-23.12 < \zeta < +3.76$ |

*Mean μ = −9.68 mV, standard deviation σ = 11.39 mV, Zeta potential $\zeta$ = Z * σ + μ

Reference buffer: 5 mM HEPES pH 8.0, 2.5 mM NaCl

The normal distribution is unique to each substrate stain under given reaction conditions (pH, conductivity, type of salt, detergent chelators, etc.). Different benefits or favorable outcomes follow a normal distribution with a physical property that holds across enzymes from various folds, as is for instance, the case of expression levels and zeta potentials for ASP and NprE charge ladder variants. In a normal distribution the peak value occurs at the mean. Comparison of enzyme and substrate charges on a common zeta potential scale reveals that optimum BMI performance occurs when the mean enzyme zeta potential in this case −9.68 mV, essentially matches the substrate stain zeta potential, in this case −8.97 mV, measured under the same conditions.

Performance levels of standard normal distributions are conveniently described in terms of their z scores as indicated in Table 1-1 (See, Abramowitz and Stegun, Handbook of Mathematical Functions with Formulas, Graphs, and Mathematical Tables, Dover, N.Y., 9th Ed., 1964). Conversion to zeta potentials is straightforward given knowledge of the mean and standard deviation defining the distribution for a given application. In this example measured cleaning performance for a protein fold is confined to zeta potential values between −40 mV and +20 mV. Variants with a cleaning performance above 80% of their fold optimum (i.e., $z=\pm 0.65$), are confined to zeta potential values between −17.08 mV and −2.28 mV. Variants with a cleaning performance above 90% of their fold optimum (i.e., $z=\pm 0.46$), are confined to zeta potential values between −14.92 mV and −4.44 mV.

Different substrate stains (e.g., grass, body soils, tomato) have different zeta potentials under the same formulation and the same substrate stain has different zeta potentials under different formulations (e.g., North American HDL, European powder dishwashing detergent). Regardless, while the substrate stain charge varies, the standard deviation of the normal distribution is expected to remain constant. Knowledge of enzyme and substrate zeta potentials in a given detergent formulation allows rapid identification of the expected performance level for that variant, as well as the direction and magnitude of charge change needed in order to achieve optimal performance levels. Measurement of the substrate zeta potential in the desired reaction medium allows optimization of the enzyme reaction on the particulate substrate in that medium. Any enzyme reaction in any medium can be optimized using a similar process.

Optimizing Reactions on Substrates Exhibiting Variable Charge

Cellulose conversion was evaluated by techniques known in the art (See, e.g., Baker et al., Appl Biochem Biotechnol, 70-72:395-403, 1998). A standard cellulosic conversion assay was used in the experiments. In this assay enzyme and buffered substrate were placed in containers and incubated at a temperature over time. The reaction was quenched with enough 100 mM glycine, pH 11, to bring the pH of the reaction mixture to at least pH 10. Once the reaction was quenched, an aliquot of the reaction mixture was filtered through a 0.2 micron membrane to remove solids. The filtered solution was then assayed for soluble sugars by HPLC according to the methods described in Baker et al., above.

Determination of Zeta-Potential of Pretreated Corn Stover (PCS)

Corn stover was pretreated with 2% w/w $H_2SO_4$ as described (Schell et al., J Appl Biochem Biotechnol, 105:69-86 [2003]) and followed by multiple washes with deionized water to obtain a pH of 4.5. Sodium acetate was added to make a final concentration of 50 mM and the solution was titrated to pH 5.0. The cellulose concentration in the reaction mixture was approximately 7%.

PCS aliquots before and after saccharification by a commercial cellulase mixture, Spezyme CP and Indiage 44L, were dosed into 1.5 mL Eppendorf centrifugation tubes and occupied about one third of the volume. Samples were centrifuged at 6,000 rpm for 5 min, the supernatant exchanged for Milli-Q™ water and the process repeated 5 times. A 100 mg/mL stock solution in MIlli-Q™ water was prepared from the rinsed corn stover. This stock was diluted to 1 mg/mL into a 50 mM sodium acetate buffer pH 5.0 for zeta potential measurements. 1 mL aliquot of each substrate sample was transferred to a clean Malvern Instruments (UK) disposable Zetasizer NS™ cuvette.

Table 1-2 indicates that throughout the course of the saccharification reaction the PCS substrate charge, expressed as zeta potential, nearly became twice as negative. Without being bound by theory, there are many explanations for a net negative charge increase including but not limited to enrichment in lignin, the non-reactive portion of this substrate, as well as non-productive binding or fouling of whole cellulases and other proteins. There is an optimal enzyme zeta potential for performance (e.g., extent of reaction and reaction rate), which matches the substrate zeta potential under reaction medium conditions. Different biomass pretreatments may dramatically influence initial substrate charge. If the enzyme or the substrate become zeta potential mismatched throughout the course of the reaction, the enzyme-substrate interaction will no longer be optimal. This effect will be dramatic for changes of nearly 10 mV, which are the case for biomass conversion.

Strategies to remedy this situation include but are not limited to supplying an enzyme blend spanning various charges; a fed-batch process approach where enzymes possessing different charges at the new optimum are supplied at different reaction times and/or extents of conversion; control of substrate surface charge through addition of formulation agents, particularly surfactants (ionic and non-ionic) or other proteins; control of substrate surface charge through pH adjustments; ionic strength adjustments throughout the reaction in order to shift the enzyme charge optima; membrane filtration, particularly reverse osmosis and nanofiltration, to control ionic strength throughout the reaction; addition of chelators to control ionic strength through elimination of salts; and control of biomass substrate charge through pretreatment processes.

TABLE 1-2

| Zeta Potential Of Acid Pretreated Corn Stover | |
|---|---|
| PCS Condition | Zeta Potential |
| Initial (before saccarification) | −12.0 ± 7.00 mV |
| After saccharification by Spezyme CP | −22.2 ± 8.67 mV |
| After saccharification by Indiage 44L | −22.7 ± 6.84 mV |

The following assays were used in the examples described below. Any deviations from the protocols provided below are indicated in the examples. In these experiments, a spectrophotometer was used to measure the absorbance of the products formed after the completion of the reactions.

Hexokinase Assay for Measurement of Residual Glucose

Residual glucose from *H. jecorina* culture supernatants expressing CBH2 variants was measured using a hexokinase assay. A volume of 5 µl of supernatant was added to 195 µl glucose hexokinase assay (Instrumentation Laboratory, Breda, Netherlands) in a 96-well microtiterplate (Costar Flat Bottom PS). The plates were incubated at room temperature for 15 min. Following incubation, the absorbance was measured at 340 nm OD. Supernatants of cultures expressing residual glucose were excluded from pooling for further studies.

HPLC Assay for Protein Content Determination

The concentration of CBH2 variant proteins from pooled culture supernantants was determined using an Agilent 1100 (Hewlet Packard) HPLC equipped with a Proswift RP 2H column (Dionex). Ten microliters of sample, mixed with 50 μl of 10% acetonitrile in filtered demineralized water was injected following equilibration of the HPLC column with 10% acetonitrile containing 0.01% trifluoroacetic acid. Compounds were eluted using a gradient of 10% to 30% acetonitrile from 0.3 min to 1 min, followed by a gradient of 30% to 65% from 1 min to 4 mins. Protein concentrations of CBH2 variants were determined from a calibration curve generated using purified wild-type CBH2 (6.25, 12.5, 25, 50 μg/ml). To calculate performance index ($P_i$ or PI), the ratio of the (average) total protein produced by a variant and (average) total protein produced by the wild-type at the same dose were averaged.

Specific Activity Determination by Phosphoric Acid Swollen Cellulose (PASC) Hydrolysis Assay Cellulose Hydrolysis:

Phosphoric acid swollen cellulose (PASC) was prepared from Avicel according to a published method (Walseth, Tappi 35:228, 1971; and Wood, Biochem J, 121:353-362, 1971). This material was diluted with buffer and water to achieve a 1% w/v mixture such that the final concentration of sodium acetate was 50 mM, pH 5.0. One hundred microliters of a 1% suspension of PASC in 50 mM sodium acetate buffer (pH5.0) was dispensed in a 96-well microtiterplate (Costar Flat Bottom PS). Ten microliters of a 5 mg/ml culture supernatant from a CBH2 deleted strain was added to the PASC, and 5, 10, 15, or 20 μl of pooled culture supernatants from *H. jecorina* cells expressing either wild-type CBH2 or CBH2 variants were added to it. Deletion of the CBH2 gene from *Hypocrea jecorina* (also referred to as *Trichoderma reesei*) is described in U.S. Pat. Nos. 5,861,271 and 5,650,322. Compensating volumes of acetate buffer were added to make up for differences in total volume. The microtiterplate was sealed and incubated in a thermostatted incubator at 50° C. under continuous shaking at 900 rpm. After two hours, the hydrolysis reaction was stopped by the addition of 100 glycine buffer, pH 10 to each well. The hydrolysis reaction products were analyzed with the PAHBAH assay.

PAHBAH Assay:

Aliquots of 150 μl of PAHBAH reducing sugar reagent (5% w/v p-hydroxybenzoic acid hydrazide (PAHBAH, Sigma #H9882, dissolved in 0.5 N HCl), (Lever, Anal Biochem, 47:273-279, 1972) were added to all wells of an empty microtiter plate. Ten microliters of the hydrolysis reaction supernatants were added to the PABAH reaction plate. All plates were sealed and incubated at 69° C. under continuous shaking of 900 rpm. After one hour the plates were placed on ice for five minutes and centrifuged at 720×g at room temperature for five minutes. Samples of 80 μL of the developed PAHBAH reaction mixtures were transferred to a fresh (read) plate and absorbance was measured at 410 nm in a spectrophotometer. A cellobiose standard was included as control. A dose response curve was generated for wild-type CBH2 protein. To calculate performance index ($P_i$ or PI), the ratio of the (average) total sugar produced by a variant and (average) total sugar produced by the wild-type at the same dose were averaged.

Specific Activity Determination by Hydrolysis of Dilute Acid Pretreated Corn Stover (PCS)

Pretreated Corn Stover (PCS):

Corn stover was pretreated with 2% w/w $H_2SO_4$ as described (Schell et al., J Appl Biochem Biotechnol, 105:69-86, 2003) and followed by multiple washes with deionized water to obtain a paste having a pH of 4.5. Sodium acetate buffer (pH 5.0) was then added to a final concentration of 50 mM sodium acetate and, if necessary, this mixture was then titrated to pH 5.0 using 1N NaOH. The cellulose concentration in the reaction mixture was approximately 7%. Sixty-five microliters of this cellulose suspension was added per well to a 96-well microtiterplate (Nunc Flat Bottom PS). Ten microliters of a 5 mg/ml culture supernatant from a CBH2 deleted strain was added to the PCS, and 5, 10, 15, or 20 μl of pooled culture supernatants from *H. jecorina* cells expressing either wild-type CBH2 or CBH2 variants were added to it. Compensating volumes of acetate buffer were added to make up for differences in total volume. After sealing of the plate, the plates were placed in a thermostatted incubator at 50° C. under continuous shaking of 1300 rpm for 5 minutes. The plates were then incubated at 50° C. while shaking at 220 rpm under 80% humidity to prevent drying. After 7 days the plates were put on ice for 5 min and the hydrolysis reaction was stopped by the addition of 100 μl glycine buffer, pH 10 to each well. The hydrolysis reaction products were analyzed with the PAHBAH assay.

PAHBAH Assay:

Aliquots of 150 μl of PAHBAH reducing sugar reagent (5% w/v p-hydroxybenzoic acid hydrazide (PAHBAH, Sigma #H9882, dissolved in 0.5 N HCl), (Lever, Anal Biochem, 47:273-279, 1972) were added to all wells of an empty microtiter plate. Ten microliters of the hydrolysis reaction supernatants were added to the PABAH reaction plate. All plates were sealed and incubated at 69° C. under continuous shaking of 900 rpm. After one hour the plates were placed on ice for five minutes and centrifuged at 720×g at room temperature for five minutes. Samples of 80 μL of the developed PAHBAH reaction mixtures were transferred to a fresh (read) plate and absorbance was measured at 410 nm in a spectrophotometer. A cellobiose standard was included as control. A dose response curve was generated for wild-type CBH2 protein. To calculate performance index ($P_i$ or PI), the ratio of the (average) total sugar produced by a variant and (average) total sugar produced by the wild-type at the same dose were averaged.

Stability of CBH2 Variants in Presence of Ethanol

The stability of wild-type CBH2 and CBH2 variants was tested in the presence of 4.5% ethanol (EtOH) at 49° C. Pooled culture supernatants (80 μL) of *H. jecorina* cells expressing CBH2 variants were added to a 96-well plate (Greiner V-bottom PS) containing 10 μl of 40.5% EtOH per well. The plates were sealed and incubated in a thermostated incubator at 49° C. for 16 hours with shaking at 900 rpm. Following incubation, the plates were placed on ice for 5 minutes. Residual CBH2 activity was determined using the phosphoric acid swollen cellulose (PASC) hydrolysis assay as described above.

To calculate residual activity, the value of the product formed by the addition of 5, 10, 15 and 20 μl of EtOH-incubated CBH2 to the residual activity PASC assay was divided by the value of the product formed by the addition of 5, 10, 15 and 20 μl of EtOH-free CBH2 to the PASC assay. The individual values of these four ratios were then averaged to give the average residual activity. To determine PI value for the variant, the value of average residual activity for the variants was then divided by the average of the residual activity values of the wild-type CBH2 controls.

Thermostability of CBH2 Variants

The thermostability of wild-type CBH2 and CBH2 variants was tested at 53° C. Pooled culture supernatant (80 μL) of *H. jecorina* cells expressing CBH2 variants were added to a 96-well plate (Greiner V-bottom PS). The plates were sealed and incubated in a thermostatted incubator at 53° C. for 16 hours with shaking at 900 rpm. Following incubation, the plates were placed on ice for 5 minutes. Residual CBH2 activity was determined using the phosphoric acid swollen cellulose (PASC) hydrolysis assay as described above.

To calculate residual activity, the value of the product formed by the addition of 5, 10, 15 and 20 μl of heat-treated CBH2 to the residual activity PASC assay was divided by the value of the product formed by the addition of 5, 10, 15 and 20 μl of unheated CBH2 to the PASC assay. The individual values of these four ratios were then averaged to give the average residual activity. To determine PI value for the variant, the value of average residual activity for the variants was then divided by the average of the residual activity values of the wild-type CBH2 controls.

Example 2

Evaluation of Lignin Binding

Lignin, a complex biopolymer of phenylpropanoid, is the chief non-carbohydrate constituent of wood that binds to cellulose fibers to harden and strengthen cell walls of plants. Because it is cross-linked to other cell wall components, lignin minimizes the accessibility of cellulose and hemicellulose to cellulose degrading enzymes. Hence, lignin is generally associated with reduced digestibility of all plant biomass. In particular the binding of cellulases to lignin reduces the degradation of cellulose by cellulases. Lignin is hydrophobic and apparently negatively charged. Thus the addition of negative charges to cellulases is contemplated to reduce their binding to lignin.

As described herein a reaction was set up to measure the effect of chemical modification on the ability of a *Trichoderma* sp. cellulase preparation to bind a component of plant polymers, namely lignin. Lignin was recovered by extensive digestion of acid pretreated sugar cane bagasse by cellulases (100 mg Laminex BG/g of cellulose) followed by hydrolysis of the cellulases by nonspecific serine protease exactly as described in Berlin et al. (Applied Biochemistry and Biotechnology, 121:163-170, 2005), except that sonication, drying, grinding and screening were not done and an acid wash (0.1 N HCl) to remove the protease followed by repeated washes with acetate buffer (50 mM sodium acetate pH 5) to return the sample to a of pH 5 were added to the procedure. Briefly 50 μL of 1.16% lignin (recovered from complete saccharification of bagasse) prepared in 50 mM sodium acetate buffer at pH 5 was combined with 4 μl of a desalted modified or an unmodified *Trichoderma* sp. cellulase preparation. Microfuge tubes containing the reaction mixture were incubated at room temperature for 1 hour, and then centrifuged at high speed to separate soluble from insoluble materials. Ten μl of the supernatant from each tube was collected. The reaction tubes were re-mixed and incubated for an additional 2 hours after which second 10 μl aliquots of the supernatant from each tube were collected. The supernatant samples were analyzed by SDS-PAGE. Reduction of the band intensity in modified *Trichoderma* sp. cellulase preparations was indicative of a reduction in lignin binding.

Example 3

Evaluation of Bagasse Binding

Bagasse is the biomass that remains after sugarcane has been crushed to extract its juice. A solution containing 2% cellulose of bagasse (acid treated, 28% solid, 57% glycan) was prepared in 50 mM sodium acetate at pH 5. Samples of unmodified or chemically-modified *Trichoderma* sp. cellulase preparations were diluted ten fold in the same sodium acetate buffer. Aliquots of the diluted enzymes were mixed with either bagasse solution or buffer alone and incubated for 1 hr at room temperature. The supernatant was collected and assayed for activity of a component of cellulase, namely beta-glucosidase.

Beta-glucosidase activity was measured using the chloro-nitro-phenyl-beta-D-glucoside (CNPG) assay. The CNPG assay is a kinetic assay in which β-glucosidase converts CNPG to the colored product 2-chloro-4-nitrophenol (CNP). OD is measured at 405 nm over a period of 10 minutes at 37° C. Rates are obtained as Vmax using the SpectraMax software and then converted to specific activity (μM CNP/sec/mg Protein). Briefly, 200 μl of 50 mM sodium acetate buffer pH 5.0 was added to each well of a 96-well microtiter plate. The plate was covered and placed in an Eppendorf Thermomixer at 37° C. for 15 minutes to allow it to equilibrate to temperature. Five μl of the enzyme samples, serially diluted in 50 mM sodium acetate buffer, pH 5.0 were added to each well after equilibration. A 10 mM CNPG stock solution was diluted 1:5 using 50 mM sodium acetate buffer, pH5.0, then 20 μl of the diluted CNPG solution (2 mM) was added to each well containing enzyme samples. The microtiter plate was transferred to a spectrophotometer (SpectraMAX, type 340; Molecular Devices) set at 37° C. and OD was read at 405 nm for 0-15 min, reading at ≤9 sec intervals.

The amount of beta-glucosidase activity of the cellulase enzyme samples that remained unbound to the bagasse substrate was considerably greater in the case of the chemically-modified *Trichoderma* sp. cellulase preparation. In particular as determined by the CNPG assay, less than 50% of the unmodified beta-glucosidase remained unbound (e.g., 50% bound) to the bagasse substrate, while nearly 80% of the modified bglu remained unbound (e.g., 20% bound) to the bagasse substrate. Taken together the modified cellulase binding data indicate that reducing the positive charges on cellulase leads to reduced binding to a more negatively-charged plant polymer substrate. In this case the plant polymer substrate was lignin remaining in acid treated biomass. Acid treated biomass from corn stover, a plant biopolymer of similar chemical composition, was demonstrated to adopt an increasingly more negative charged during the course of saccharification, as determined by measurement of zeta potential (See, Table 1-2).

Example 4

Saccharification of Acid-Pretreated Bagasse

Figure 1A:
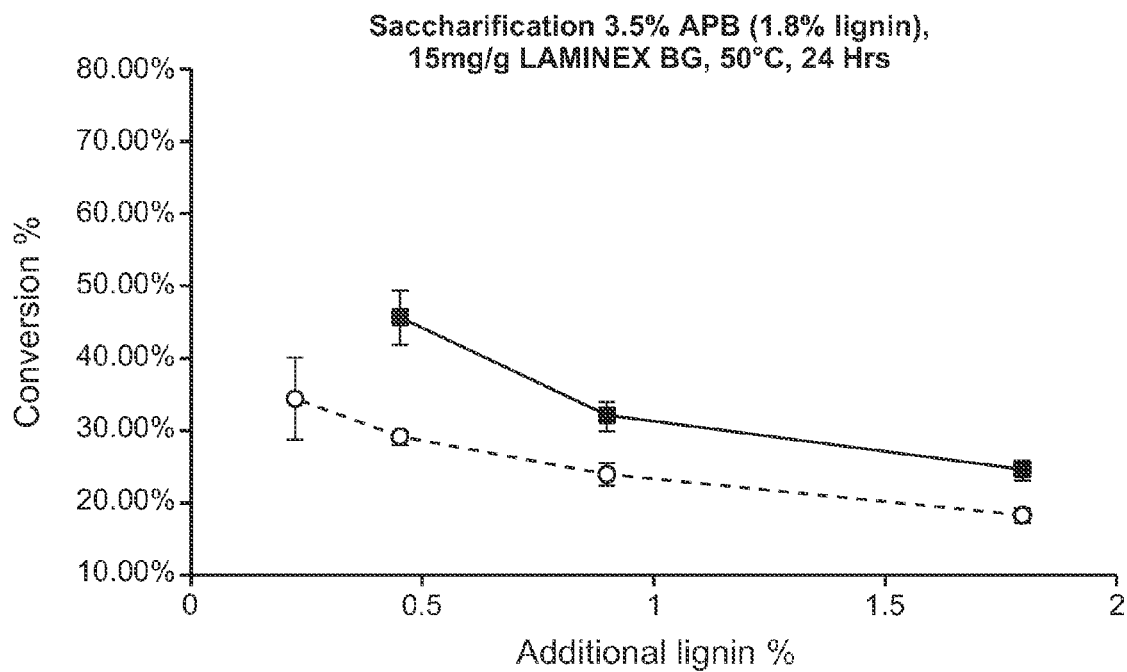
FIG. 1A and FIG. 1B shows results after 24 and 48 hour incubations, respectively.
Figure 1B:
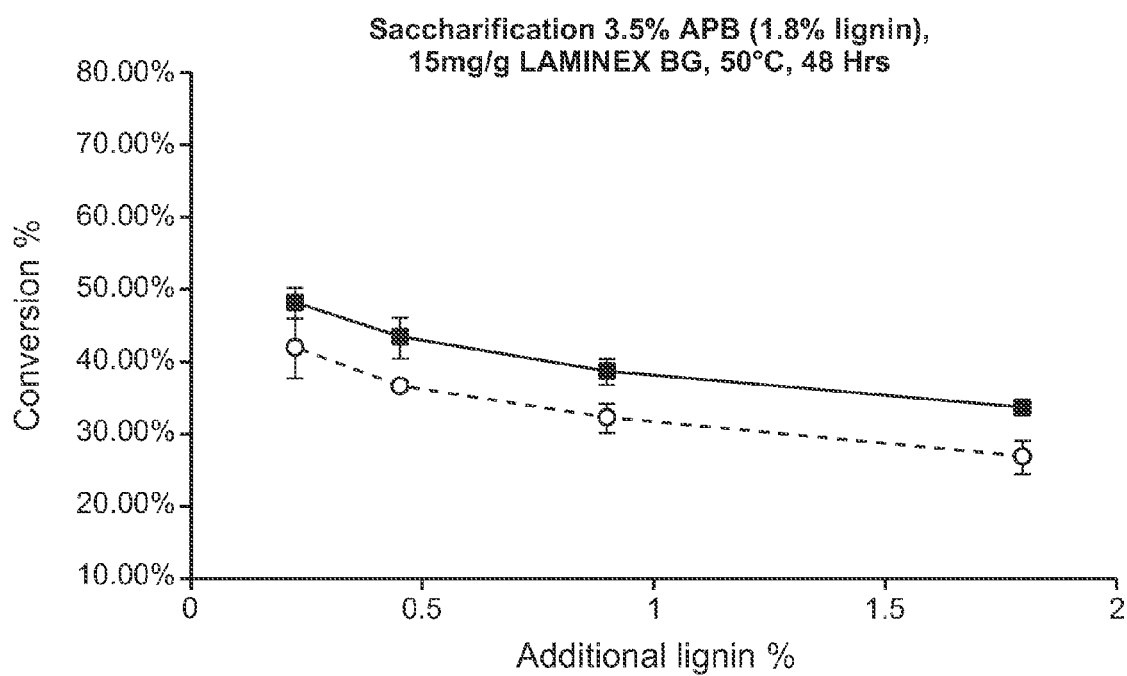

Saccharification of cellulose present in acid-pretreated bagasse (APB) containing varying amounts of additional lignin was evaluated using chemically-modified and unmodified *Trichoderma* sp. cellulase preparations and assayed by HPLC to monitor release of sugars, DP1 to DP7. The results are shown on in FIG. 1 as percent conversion of the polymer substrate. In a microtiter plate, 200 μL of APB (3.5% glucan) was prepared in 50 mM sodium acetate buffer at pH 5, and adjusted to varying amounts of lignin. Twenty microliters of cellulase enzyme solution (unmodified or modified LAMINEX BG) was added to the wells. The plates were covered with aluminum plate sealers and placed in incubators at 50° C., with shaking, for 24 hrs or 48 hrs. The reaction was terminated by adding 100 μl 100 mM glycine pH 10 to each well. Following thorough mixing, the contents of the microtiter plate wells were filtered through a Millipore 96-well filter plate (0.45 μm, PES). The filtrate was diluted into a plate containing 100 μl 10 mM Glycine pH 10 and the amount of soluble sugars (DP1 through DP7) produced measured by HPLC. The Agilent 1100 series HPLC was equipped with a de-ashing/guard column (Biorad Catalog No. 125-0118) and an Aminex lead based carbohydrate column (Aminex Catalog No. HPX-87P). The mobile phase used was water with a 0.6 ml/min flow rate. Soluble sugar standards (DP1-DP7) obtained from Sigma were all diluted in Milli-Q water to 100 mg/mL and used for converting peak area for the individual sugars to actual sugar concentrations. The percent of conversion was calculated by dividing the sugars measured from HPLC by 100% conversion of cellulose to glucose.

Cellulase binding to lignin will decrease its efficiency of degrading cellulose. This is demonstrated as a reduction in cellulose conversion in the presence of increasing amounts of lignin present in the saccharification reactions. This trend persists in the modified cellulase preparations. However, there is a 10% increase in cellulose conversion in the modified cellulase samples as compared to unmodified cellulase samples. This result indicates that increasing negative charge of the cellulase reduces the nonproductive binding of cellulase to lignin.

Example 5

Chemical Modified CBH2 Increased Saccharification of APB

Purified *Trichoderma* CBH1, CBH2 variant, EG1, EG2 and beta-glucosidase were chemically modified as described in example 1. CBH2 variant used in this experiment has multiple substitutions (P98L/M134V/T154A/I2112V/S316P/S413Y with numbers corresponding to the wild type mature CBH2 cellulase) as described in US Pub. No. 2006/0205042. The amino acid sequence of the mature CBH2 variant is as follows:

```
                                                     (SEQ ID NO: 14)
QACSSVWGQCGGQNWSGPTCCASGSTCVYSNDYYSQCLPGAASSSSSTRAASTT

SRVSPTTSRSSSATPPPGSTTTRVPPVGSGTATYSGNPFVGVTLWANAYYASEVSSLAIPS

LTGAMATAAAAVAKVPSFVWLDTLDKTPLMEQTLADIRAANKNGGNYAGQFVVYDLP

DRDCAALASNGEYSIADGGVAKYKNYIDTIRQIVVEYSDVRTLLVIEPDSLANLVTNLGT

PKCANAQSAYLECINYAVTQLNLPNVAMYLDAGHAGWLGWPANQDPAAQLFANVYK

NASSPRALRGLATNVANYNGWNITSPPPYTQGNAVYNEKLYIHAIGPLLANHGWSNAFF

ITDQGRSGKQPTGQQQWGDWCNVIGTGFGIRPSANTGDSLLDSFVWVKPGGECDGTSD

SSAPRFDYHCALPDALQPAPQAGAWFQAYFVQLLTNANPSFL.
```

Chemical modifications of CBH1, CBH2 variant, EG1, EG2 and beta-glucosidase were verified by their shifted mobility on the native gel compared to the unmodified proteins. Modified CBH1, CBH2 variant, EG1, EG2 and beta-glucosidase have more negative charges. All the protein concentrations were measured using a NanoDrop™ spectrophotometer (Thermo). A saccharification reaction was set up in microtiter plate, in each well of a microtiter plate, 150 uL of APB (7% glucan prepared as described above for PCS) was prepared in 50 mM sodium acetate buffer at pH 5, 20 µl of enzyme mix of 21 µg total protein was added so that the final protein to cellulose ratio in each well is 20 mg/g. Six enzyme mixes were made by adding purified modified or unmodified Bglu, CBH2 variant, EG1, or EG2 to a *T. reesei* background in which the genes encoding cellobiohydrolase I (CBHI, Cel7a), cellobiohydrolase II (CBHII, Cel6a), endo-glucanase I (EGI, Cel7b), and endoglucanase II (EGII, Cel5a) have been inactivated (See, US 2007/0128690). In each mix, 72.5% *T. reesei* background, 2.5% Bglu, 15% CBH2 variant, 5% EG1, 5% EG2 were added, the first four mixes have one protein that is not modified, the fifth mix has all the protein not modified, and the sixth mix has all the protein modified. The plate was incubated at 50 C for 72 hours. The reaction was terminated by adding 100 µl 100 mM glycine pH 10 to each well. Following thorough mixing, the contents of the microtiter plate wells were filtered through a Millipore 96-well filter plate (0.45 µm, PES). The filtrate was diluted into a plate containing 100 µl 10 mM Glycine pH 10 and the amount of soluble sugars (DP1 through DP7) produced measured by HPLC. The Agilent 1100 series HPLC was equipped with a de-ashing/guard column (Biorad Catalog No. 125-0118) and an Aminex lead based carbohydrate column (Aminex Catalog No. HPX-87P). The mobile phase used was water with a 0.6 ml/min flow rate. Soluble sugar standards (DP1-DP7) obtained from Sigma were all diluted in Milli-Q water to 100 mg/mL and used for converting peak area for the individual sugars to actual sugar concentrations. The percent of conversion was calculated by dividing the sugars measured from HPLC by 100% conversion of cellulose to glucose.

Figure 2A:
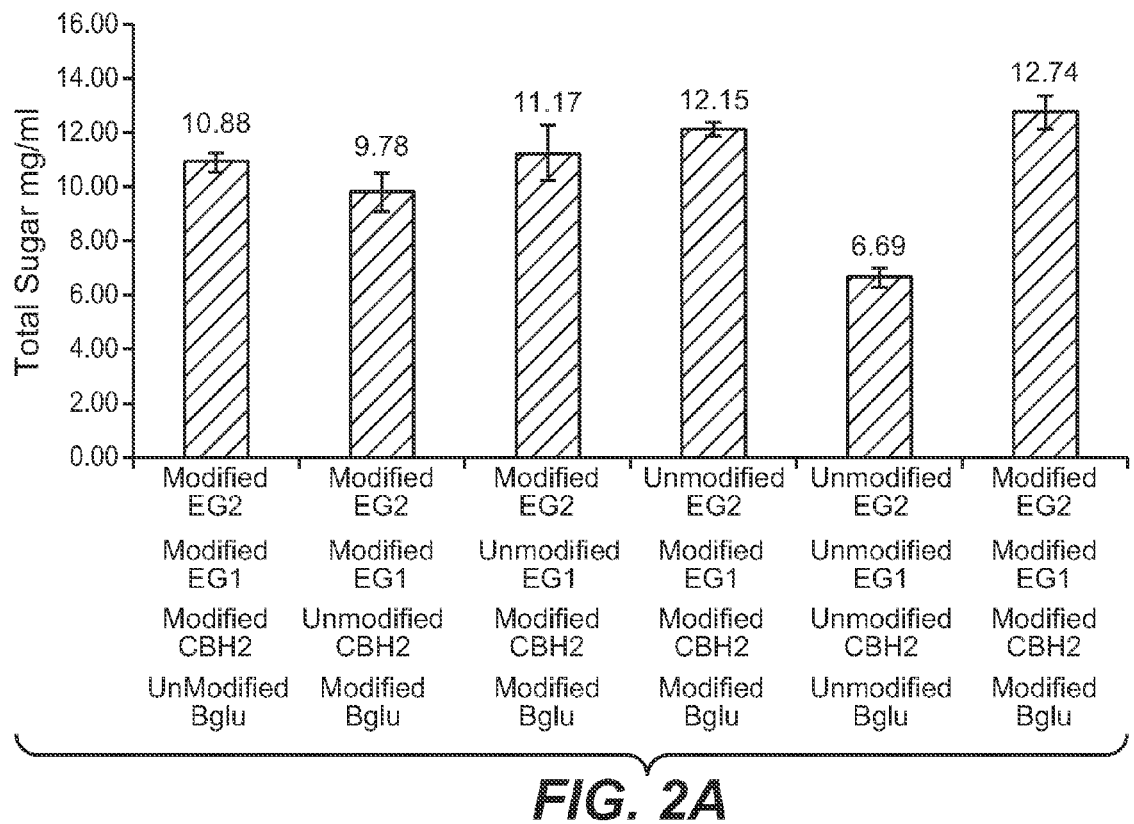
FIG. 2A illustrates saccharification comparing modified cellulases and FIG. 2B shows the difference of saccharification using modified and unmodified cellulases.
Figure 2B:
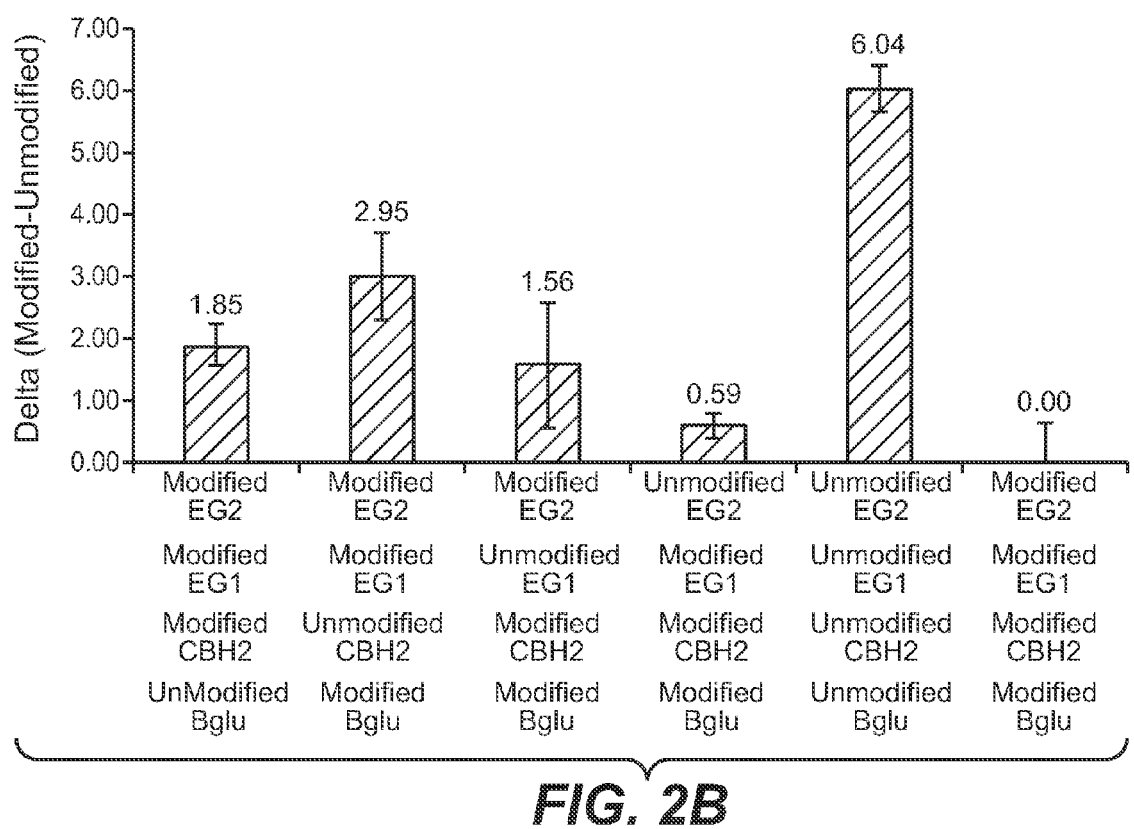

FIG. 2A shows that for the sixth enzyme mix (modified EG2, EG1, CBH2 variant and beta-glucosidase) with all protein modified has the highest cellulose conversion, and fifth enzyme mix with all protein unmodified has the lowest conversion. Comparing the first four enzyme mixes, the second enzyme mix with the unmodified CBH2 gave next lowest conversion. FIG. 2B shows the advantages of modified proteins over unmodified proteins in cellulose conversion.

Example 6

Preparation of *T. reesei* CBH2 Charge Ladder Variants

As determined during development of the present disclosure, succinylation of surface lysine residues of CBH2 improved performance on APB, and on pretreated corn stover. The charge of modified CBH2 variant was about −17 compared to unmodified CBH2 variant. With this in mind, a charge ladder of CBH2 was designed for determination of the optimal surface charge in cellulase performance applications.

SEQ ID NO:1 sets forth the reference *Hypocrea jecorina* CBH2 coding DNA sequence:

atgattgtcggcattctcaccacgctggctacgctggccacactcgcagctagtgtgcctctagaggagcggcaagcttgctcaagcgtctg gggccaatgtggtggccagaattggtcgggtccgacttgctgtgcttccggaagcacatgcgtctactccaacgactattactcccagtgtct tcccggcgctgcaagctcaagctcgtccacgcgcgccgcgtcgacgacttctcgagtatcccccacaacatcccggtcgagctccgcgac gcctccacctggttctactactaccagagtacctccagtcggatcgggaaccgctacgtattcaggcaaccctttgttggggtcactccttgg gccaatgcatattacgcctctgaagttagcagcctcgctattcctagcttgactggagccatggccactgctgcagcagctgtcgcaaaggtt ccctcttttatgtggctagatactcttgacaagacccctctcatggagcaaaccttggccgacatccgcaccgccaacaagaatggcggtaa ctatgccggacagtttgtggtgtatgacttgccggatcgcgattgcgctgcccttgcctcgaatggcgaatactctattgccgatggtggcgtc gccaaatataagaactatatcgacaccattcgtcaaattgtcgtggaatattccgatatccggaccctcctggttattgagcctgactctcttgcc aacctggtgaccaacctcggtactccaaagtgtgccaatgctcagtcagcctaccttgagtgcatcaactacgccgtcacacagctgaaccttt ccaaatgttgcgatgtatttggacgctggccatgcaggatggcttggctggccggcaaaccaagacccggccgctcagctatttgcaaatgt ttacaagaatgcatcgtctccgagagctcttcgcggattggcaaccaatgtcgccaactacaacgggtggaacattaccagcccccatcgt acacgcaaggcaacgctgtctacaacgagaagctgtacatccacgctattggacctcttcttgccaatcacggctggtccaacgccttcttca tcactgatcaaggtcgatcgggaaagcagcctaccggacagcaacagtggggagactggtgcaatgtgatcggcaccggatttggtattc gcccatccgcaaacactggggactcgttgctggattcgtttgtctgggtcaagccaggcggcgagtgtgacggcaccagcgacagcagtg cgccacgatttgactcccactgtgcgctcccagatgccttgcaaccggcgcctcaagctggtgcttggttccaagcctactttgtgcagcttct cacaaacgcaaacccatcgttcctgtaa*

SEQ ID NO:2 sets forth the *Hypocrea jecorina* CBH2 full length protein sequence:

MIVGILTTLATLATLAASVPLEERQACSSVWGQCGGQNWSGPTCCASGSTCVYSNDYYSQCLPGA

ASSSSSTRAASTTSRVSPTTSRSSSATPPPGSTTTRVPPVGSGTATYSGNPFVGVTPWANAYYAS

EVSSLAIPSLTGAMATAAAAVAKVPSFMWLDTLDKTPLMEQTLADIRTANKNGGNYAGQFVVYDL

PDRDCAALASNGEYSIADGGVAKYKNYIDTIRQIVVEYSDIRTLLVIEPDSLANLVTNLGTPKCA

NAQSAYLECINYAVTQLNLPNVAMYLDAGHAGWLGWPANQDPAAQLFANVYKNASSPRALRGLAT

NVANYNGWNITSPPSYTQGNAVYNEKLYIHAIGPLLANHGWSNAFFITDQGRSGKQPTGQQQWGD

WCNVIGTGFGIRPSANTGDSLLDSFVWVKPGGECDGTSDSSAPRFDSHCALPDALQPAPQAGAWF

QAYFVQLLTNANPSFL*

SEQ ID NO:3 sets forth the *Hypocrea jecorina* CBH2 mature protein sequence:

QACSSVWGQCGGQNWSGPTCCASGSTCVYSNDYYSQCLPGAASSSSSTRAASTTSRVSPTTSRSS

SATPPPGSTTTRVPPVGSGTATYSGNPFVGVTPWANAYYASEVSSLAIPSLTGAMATAAAAVAKV

PSFMWLDTLDKTPLMEQTLADIRTANKNGGNYAGQFVVYDLPDRDCAALASNGEYSIADGGVAKY

KNYIDTIRQIVVEYSDIRTLLVIEPDSLANLVTNLGTPKCANAQSAYLECINYAVTQLNLPNVAM

YLDAGHAGWLGWPANQDPAAQLFANVYKNASSPRALRGLATNVANYNGWNITSPPSYTQGNAVYN

EKLYIHAIGPLLANHGWSNAFFITDQGRSGKQPTGQQQWGDWCNVIGTGFGIRPSANTGDSLLDS

FVWVKPGGECDGTSDSSAPRFDSHCALPDALQPAPQAGAWFQAYFVQLLTNANPSFL*

Residues selected to be mutagenized included non-conserved, exposed lysine, arginine, asparigine, and glutamine residues, which were selected for substitution to introduce negative charges. Succinylated lysines in modified CBH2 were identified by mass spectrometry and selected for mutagenesis to glutamate, resulting in a −2 charge difference per substitution. Other residues were selected for substitution by analysis of CBH2 three-dimensional structure combined with amino acids alignment of homologous CBH2 sequences (See, e.g., FIG. 3 of US Pub. No. US 2006/0205042, herein incorporated by reference).

Surface residues that were highly variable in the CBH2 amino acid sequence alignment were candidates for mutagenesis. However, accumulation of substitutions in close proximity was avoided. Arginine was replaced with glutamine (charge −1), and glutamine and asparagine were substituted with the respective carboxyl variants (charge −1). In addition, aspartate and glutamate residues were selected for substitution to the respective amine residues for completion of the charge ladder (charge +1). Specific CBH2 substitutions are shown in Table 6-1, with all positions shown with the exception of R63 and R77, located in the CBH2 catalytic domain. A net positive charge can be created by either removal of a negatively charged residue or by introduction of a positively charged residue. Likewise a net negative charge can be created by either removal of a positively charged residue or by introduction of a negatively charged residue.

TABLE 6-1

CBH2 Substitutions

| Introduction of negative charge and removal of positive charge Lysine | Removal of positive charge Arginine | Introduction of negative charge Asparagine | Introduction of negative charge Glutamine | Removal of negative charge Aspartate | Removal of negative charge Glutamate |
|---|---|---|---|---|---|
| K157E | R153Q | N382D | Q204E | D189N | E208Q |
| K129E | R294Q | N344D | Q147E | D211N | E244Q |
| K288E | R203Q | N237D | Q239E | D405N | E146Q |
| K194E | R378Q | N339D | Q281E | D277N | |
| K356E | R63Q | N289D | | D151N | |
| K327E | R77Q | N161D | | | |
| | | N285D | | | |
| | | N197D | | | |
| | | N254D | | | |
| | | N247D | | | |

For preparation of a CBH2 charge ladder, ten CBH2 charge variants (C-1 to C-10) were designed spanning a charge range of +8 to −32, compared to the wild-type CBH2 in steps of 4 as shown in Table 6-2.

TABLE 6-2

CBH2 Charge Ladder

| C-1 | C-2 | CBH2 | C-3 | C-4 | C-5 | C-6 | C-7 | C-8 | C-9 | C-10 |
|---|---|---|---|---|---|---|---|---|---|---|
| 8 | 4 | 0 | −4 | −8 | −12 | −16 | −20 | −24 | −28 | −32 |
| D189N | D189N | WT | K157E | K157E | K157E | K157E | K157E | K157E | K157E | K157E |
| E208Q | E208Q | | K129E | K129E | K129E | K129E | K129E | K129E | K129E | K129E |
| D211N | D211N | | | K288E | K288E | K288E | K288E | K288E | K288E | K288E |
| D405N | D405N | | | K194E | K194E | K194E | K194E | K194E | K194E | K194E |
| E244Q | | | | | K356E | K356E | K356E | K356E | K356E | K356E |
| D277N | | | | | K327E | K327E | K327E | K327E | K327E | K327E |
| D151N | | | | | | R153Q | R153Q | R153Q | R153Q | R153Q |
| E146Q | | | | | | R294Q | R294Q | R294Q | R294Q | R294Q |
| | | | | | | R203Q | R203Q | R203Q | R203Q | R203Q |
| | | | | | | R378Q | R378Q | R378Q | R378Q | R378Q |
| | | | | | | | N382D | N382D | N382D | N382D |
| | | | | | | | N344D | N344D | N344D | N344D |
| | | | | | | | N237D | N237D | N237D | N237D |
| | | | | | | | N339D | N339D | N339D | N339D |
| | | | | | | | | N289D | N289D | N289D |
| | | | | | | | | N161D | N161D | N161D |
| | | | | | | | | Q204E | Q204E | Q204E |
| | | | | | | | | Q147E | Q147E | Q147E |
| | | | | | | | | | N285D | N285D |
| | | | | | | | | | N197D | N197D |
| | | | | | | | | | N254D | N254D |
| | | | | | | | | | N247D | N247D |
| | | | | | | | | | | Q239E |
| | | | | | | | | | | Q281E |
| | | | | | | | | | | R63Q |
| | | | | | | | | | | R77Q |

The amino acid sequences of the variants were back translated to DNA and codon optimized for expression in *Trichoderma reesei* using GeneDesigner software (DNA2.0). The codon-optimized cbh2 variant genes were synthesized and the DNA of the CBH2 surface charge variants (SCVs) was amplified from the DNA2.0 constructs by PCR with using primers: GGHTK22 forward 5'-CACCATGATCGTGG-GAATTCTTACTACTC-3' (SEQ ID NO:15); and GGTHK23 reverse 5'-CTACAAAAACGAAGGGTTCGCATT-3' (SEQ ID NO:16). In one experiment, site directed mutagenesis was used to introduce K129E and K157E mutations (cbh2 charge variant C-3) in the genomic DNA of wild type CBH2. CBH2 charge variant C-3 was cloned into pTrex3GM and expressed as described below.

The PCR products were purified and cloned into pENTR/TOPO for transformation of *E. coli* TOP10 cells. Plasmid DNA was isolated from single colonies and the correct sequence was verified. CBH2 SCVs were cloned into pTrex3GM, pTTTpyr(pcbh1), and pTTTpyr(pstp1) as shown in Table 6-3.

TABLE 6-3

Expression Clones of CBH2 Surface Charge Variants

| CBH2 Variant | Destination vectors | | |
|---|---|---|---|
| | pTrex3gM | pTTTpyr ($P_{cbh1}$) | pTTTpyr($P_{stp1}$) |
| C-1 (pTK354a) | 1 | 11 | 21 |
| C-2 (pTK355a) | 2 | 12 | 22 |
| C-3 (pTK356a) | 3 | 13 | 23 |
| C-4 (pTK357a) | 4 | 14 | 24 |
| C-5 (pTK358a) | 5 | 15 | 25 |
| C-8 (pTK361a) | 6 | 16 | 26 |
| C-6 (pTK359a) | (7) | (17) | (27) |
| C-7 (pTK360a) | 8 | 18 | 28 |
| C-9 (pTK362a) | 9 | 19 | 29 |
| C-10 (pTK363b) | 10 | 20 | 30 |

CBH2 surface charge variants (SCV) in *T. reesei*. Biolistic transformation of *T. reesei* with the pTrex3gM expression vector containing the cbh2 charge variant C3 (with K129E and K157E mutations) open reading frame was performed using the following protocol. *T. reesei* in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated was used.). Transformation of the *Trichoderma reesei* strain by the biolistic transformation method was accomplished using a Biolistic® PDS-1000/he Particle Delivery System from Bio-Rad (Hercules, Calif.) following the manufacturer's instructions (See WO 05/001036 and US 2006/0003408). Transformants were transferred to new acetamide selection plates. Stable transformants were inoculated into filter microtiter plates (Millipore), containing 200 ul/well of glycine minimal media (6.0 g/L glycine; 4.7 g/L $(NH_4)_2SO_4$; 5.0 g/L $KH_2PO_4$; 1.0 g/L $MgSO_4.7H_2O$; 33.0 g/L PIPPS; p.H. 5.5) with post sterile addition of ~2% glucose/sophorose mixture as the carbon source, 10 ml/L of 100 g/L of $CaCl_2$, 2.5 ml/L of *T. reesei* trace elements (400×): 175 g/L Citric acid anhydrous; 200 g/L $FeSO_4.7H_2O$; 16 g/L $ZnSO_4.7H_2O$; 3.2 g/L $CuSO_4.5H_2O$; 1.4 g/L $MnSO_4.H_2O$; 0.8 g/L $H_3BO_3$. Transformants were grown in liquid culture for 5 days in $O_2$ rich chamber housed in a 28° C. incubator. The supernatant samples from the filter microtiter plate were obtained by using a vacuum manifold. Samples were run on 4-12% NuPAGE gels (Invitrogen) according to the manufactures instructions. The gel was stained with Simply Blue stain (Invitrogen). Expression of additional CHB2 surface charge variants may be accomplished using this method.

Example 7

Generation of CBH2 Charge Variants in *T. reesei*

The pTTTpyr-cbh2 plasmid containing the *Hypocrea jecorina* CBH2 protein encoding sequence (SEQ ID NO:1) was sent to BASEClear (Leiden, The Netherlands), GeneArt AG (Regensburg, Germany), and Sloning BioTechnology GmbH (Puchheim, Germany) for the generation of Site Evaluation Libraries (SELs). The plasmid map of pTTTpyr-cbh2 is shown in FIG. 5. A request was made to the vendors for the generation of positional libraries at each of the sites in *Hypocrea jecorina* CBH2 mature protein (SEQ ID NO:3). The amino acid sequence of CBH2 full length protein is shown in SEQ ID NO:2.

SEQ ID NO:1 sets forth the reference *Hypocrea jecorina* CBH2 coding DNA sequence:

```
atgattgtcggcattctcaccacgctggctacgctggccacactcgcagctagtgtgcctctagaggagcggcaagcttgctcaagcgtctg gggccaatgtggtggccagaattggtcgggtccgacttgctgtgcttccggaagcacatgcgtctactccaacgactattactcccagtgtct tcccggcgctgcaagctcaagctcgtccacgcgcgccgcgtcgacgacttctcgagtatcccccacaacatcccggtcgagctccgcgac gcctccacctggttctactactaccagagtacctccagtcggatcgggaaccgctacgtattcaggcaaccctttgttggggtcactccttgg gccaatgcatattacgcctctgaagttagcagcctcgctattcctagcttgactggagccatggccactgctgcagcagctgtcgcaaaggtt ccctcttttatgtggctagatactcttgacaagacccctctcatggagcaaaccttggccgacatccgcaccgccaacaagaatggcggtaa ctatgccggacagtttgtggtgtatgacttgccggatcgcgattgcgctgcccttgcctcgaatggcgaatactctattgccgatggtggcgtc gccaaatataagaactatatcgacaccattcgtcaaattgtcgtggaatattccgatatccggaccctcctggttattgagcctgactctcttgcc aacctggtgaccaacctcggtactccaaagtgtgccaatgctcagtcagcctaccttgagtgcatcaactacgccgtcacacagctgaacctt ccaaatgttgcgatgtatttggacgctggccatgcaggatggcttggctggccggcaaaccaagacccggccgctcagctatttgcaaatgt ttacaagaatgcatcgtctccgagagctcttcgcggattggcaaccaatgtcgccaactacaacgggtggaacattaccagcccccccatcgt acacgcaaggcaacgctgtctacaacgagaagctgtacatccacgctattggacctcttcttgccaatcacggctggtccaacgccttcttca tcactgatcaaggtcgatcgggaaagcagcctaccggacagcaacagtggggagactggtgcaatgtgatcggcaccggatttggtattc
```

```
-continued
gcccatccgcaaacactggggactcgttgctggattcgtttgtctgggtcaagccaggcggcgagtgtgacggcaccagcgacagcagtg cgccacgatttgactcccactgtgcgctcccagatgccttgcaaccggcgcctcaagctggtgcttggttccaagcctactttgtgcagcttct cacaaacgcaaacccatcgttcctgtaa*
```

SEQ ID NO:2 sets forth the *Hypocrea jecorina* CBH2 full length protein sequence:

MIVGILTTLATLATLAASVPLEERQACSSVWGQCGGQNWSGPTCCASGSTCVYSNDYYSQCLPGA

ASSSSSTRAASTTSRVSPTTSRSSSATPPPGSTTTRVPPVGSGTATYSGNPFVGVTPWANAYYAS

EVSSLAIPSLTGAMATAAAAVAKVPSFMWLDTLDKTPLMEQTLADIRTANKNGGNYAGQFVVYDL

PDRDCAALASNGEYSIADGGVAKYKNYIDTIRQIVVEYSDIRTLLVIEPDSLANLVTNLGTPKCA

NAQSAYLECINYAVTQLNLPNVAMYLDAGHAGWLGWPANQDPAAQLFANVYKNASSPRALRGLAT

NVANYNGWNITSPPSYTQGNAVYNEKLYIHAIGPLLANHGWSNAFFITDQGRSGKQPTGQQQWGD

WCNVIGTGFGIRPSANTGDSLLDSFVWVKPGGECDGTSDSSAPRFDSHCALPDALQPAPQAGAWF

QAYFVQLLTNANPSFL*

SEQ ID NO:3 sets forth the *Hypocrea jecorina* CBH2 mature protein sequence:

QACSSVWGQCGGQNWSGPTCCASGSTCVYSNDYYSQCLPGAASSSSSTRAASTTSRVSPTTSRSS

SATPPPGSTTTRVPPVGSGTATYSGNPFVGVTPWANAYYASEVSSLAIPSLTGAMATAAAAVAKV

PSFMWLDTLDKTPLMEQTLADIRTANKNGGNYAGQFVVYDLPDRDCAALASNGEYSIADGGVAKY

KNYIDTIRQIVVEYSDIRTLLVIEPDSLANLVTNLGTPKCANAQSAYLECINYAVTQLNLPNVAM

YLDAGHAGWLGWPANQDPAAQLFANVYKNASSPRALRGLATNVANYNGWNITSPPSYTQGNAVYN

EKLYIHAIGPLLANHGWSNAFFITDQGRSGKQPTGQQQWGDWCNVIGTGFGIRPSANTGDSLLDS

FVWVKPGGECDGTSDSSAPRFDSHCALPDALQPAPQAGAWFQAYFVQLLTNANPSFL*

Purified pTTTpyr-cbh2 plasmids (p$_{cbh1}$, Amp$^R$, Acetamide$^R$) containing open reading frames encoding CBH2 variant sequences were obtained from the vendors specified above. Protoplasts of *H. jecorina* strain (Δeg1, Δeg2, Δcbh1 Δcbh2) were transformed with the pTTTpyr constructs and grown on selective agar containing acetamide at 28° C. for 7 days. Briefly, biolistic transformation of *H. jecorina* was performed using the following protocol and a strain in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated. Transformation of the *H. jecorina* by the biolistic transformation method was accomplished using a Biolistic® PDS-1000/he Particle Delivery System from Bio-Rad (Hercules, Calif.) following the manufacturer's instructions (See WO 05/001036 and US 2006/0003408). Spores were harvested, replated on acetamide agar, and incubated at 28° C. for 7 days. Spores were harvested in 15% glycerol and stored at −20° C. for further use. For CBH2 variant protein production, a volume of 10 μl spore suspension was added to 200 μl glycine minimal medium supplemented with 2% glucose/sophorose mixture in a PVDF filter plate: 6.0 g/L glycine, 4.7 g/L $(NH_4)_2SO_4$; 5.0 g/L $KH_2PO_4$; 1.0 g/L $MgSO_4·7H_2O$; 33.0 g/L PIPPS; pH 5.5; with post sterile addition of ~2% glucose/sophorose mixture as the carbon source, 10 ml/L of 100 g/L of $CaCl_2$, 2.5 ml/L of *T. reesei* trace elements (400×): 175 g/L Citric acid anhydrous; 200 g/L $FeSO_4·7H_2O$; 16 g/L $ZnSO_4·7H_2O$; 3.2 g/L $CuSO_4·5H_2O$; 1.4 g/L $MnSO_4·H_2O$; 0.8 g/L $H_3BO_3$. Each CBH2 variant was grown in quadruplicate. After sealing the plate with an oxygen permeable membrane, the plates were incubated at 28° C. for 6 days, while shaking at 220 rpm. Supernatant was harvested by transferring the culture medium to a microtiter plate under low pressure and tested for residual glucose using the hexokinase assay as described in Example 1.

Example 8

Expression, Activity and Performance of CBH2 Variants

*H. jecorina* CBH2 charge variants were tested for various properties of interest. In particular, the cellulase variants were tested for protein expression using the HPLC assay (HPLC), specific activity using the PASC hydrolysis assay (Act. PASC) and the PCS hydrolysis assay (Act. PCS), stability in the presence of ethanol (EtOH ratio) and thermostability (heat ratio) as described in Example 1. Performance data for CBH2 charge variants are shown in Table 8-1. Performance index (PI) is the ratio of performance of the variant cellulase to the parent or reference cellulase. Various terms set forth below are used to describe the mutation: up mutations have a PI>1; neutral mutations have a PI≥0.5, non-deleterious mutations have a PI>0.05; deleterious mutations have a PI=0.05; combinable mutations are those mutations for which the variant has Performance index values≥0.5 for at least one property. Combinable mutations are mutations that can be combined to deliver proteins with appropriate performance indices for one or more desired properties. Positions at which mutations occur are classed as follows: Non-restrictive positions have ≥20% neutral mutations for at least one property; and Restrictive positions have <20% neutral mutations for activity and stability. Fully Restrictive positions have no neutral mutations for activity or stability.

These data may be used to engineer any CBH2. Even if the CBH2 to be engineered has an amino acid different from that of *Hypocrea jecorina* CBH2 at a particular position, these data may be used to find a substitution that will alter the desired properties by identifying the best choice substitution, including substitution to the *Hypocrea jecorina* CBH2 wild type amino acid.

Table 8-11 shows performance index values (Pi or PI) for variants of *Hypocrea jecorina* CBH2. Performance indices less than or equal to 0.05 were fixed to 0.05 and indicated in bold italics in the table.

TABLE 8-1

Performance Indexes of CBH2 Charge Variants

| Variant | HPLC | PASC sp. ac. | PCS sp. ac. | Res EtOH | Res Heat |
|---|---|---|---|---|---|
| R63A | 1.21 | 1.03 | 0.94 | 0.97 | 1.00 |
| R63C | 1.47 | 1.02 | 1.05 | 0.96 | 1.06 |
| R63D | 0.12 | 0.11 | 0.19 | *0.05* | 1.02 |
| R63E | 0.88 | 0.94 | 0.98 | 0.96 | 1.05 |
| R63F | 0.91 | 0.95 | 0.85 | 0.94 | 1.09 |
| R63G | 0.71 | 0.96 | 0.95 | 1.08 | 1.20 |
| R63I | 0.81 | 0.93 | 1.11 | 1.03 | 1.09 |
| R63L | 0.94 | 0.96 | 0.91 | 1.06 | 1.29 |
| R63M | 1.22 | 0.99 | 1.10 | 1.05 | 1.09 |
| R63N | 1.23 | 1.02 | 1.11 | 1.03 | 1.07 |
| R63P | 0.96 | 0.99 | 1.17 | 1.04 | 1.09 |
| R63Q | 0.87 | 0.99 | 1.01 | 0.99 | 1.13 |
| R63S | 0.59 | 0.92 | 1.09 | 1.00 | 0.94 |
| R63T | 0.43 | 0.87 | 0.94 | 0.91 | 0.84 |
| R63V | 1.00 | 0.99 | 0.89 | 1.03 | 1.06 |
| R63W | 0.98 | 0.97 | 0.91 | 1.08 | 1.10 |
| R63Y | 1.29 | 1.03 | 0.99 | 1.06 | 1.07 |
| R77F | 0.25 | 0.81 | 0.58 | 0.92 | 0.81 |
| R77G | 0.41 | 1.02 | 0.75 | 1.00 | 0.93 |
| R77L | 0.14 | 0.53 | 0.36 | 0.94 | 0.79 |
| R77N | 0.83 | 0.99 | 0.87 | 1.00 | 1.02 |
| K129A | 0.23 | 1.03 | 0.81 | 0.74 | 0.57 |
| K129L | 0.80 | 0.94 | 0.80 | 0.82 | 0.71 |
| K129N | 0.15 | 0.93 | 0.65 | 0.73 | 0.61 |
| K129Q | 0.41 | 1.30 | 0.89 | 1.01 | 0.99 |
| K129S | 0.37 | 1.05 | 0.92 | 0.84 | 0.84 |
| K129T | 0.16 | 0.87 | 0.37 | 0.81 | 0.69 |
| K129V | 0.17 | 0.93 | 0.91 | 0.63 | 0.45 |
| K129Y | 0.35 | 0.95 | 0.82 | 0.68 | 0.46 |
| Q147E | 0.86 | 1.00 | 0.88 | 1.07 | 1.05 |
| R153A | 0.23 | 0.50 | 0.72 | 0.63 | 0.64 |
| R153C | 0.26 | 0.51 | 0.86 | 0.94 | 0.88 |
| R153D | 0.35 | 0.35 | 0.54 | 0.75 | 0.72 |
| R153E | 0.27 | 0.69 | 0.75 | 0.79 | 0.80 |
| R153F | 0.21 | 0.38 | 0.69 | 0.68 | 0.58 |
| R153G | 0.21 | 0.31 | 0.59 | 0.62 | 0.92 |
| R153I | 0.22 | 0.28 | 0.37 | 0.63 | 1.09 |
| R153L | 0.19 | 0.30 | 0.40 | 0.94 | 0.44 |
| R153M | 0.31 | 0.70 | 0.86 | 0.92 | 1.05 |
| R153N | 0.22 | 0.20 | 0.42 | 1.12 | 1.23 |
| R153P | 0.23 | 0.14 | 0.10 | 0.39 | 2.17 |
| R153Q | 0.24 | 0.52 | 0.99 | 0.77 | 1.05 |
| R153S | 0.41 | 0.78 | 0.99 | 0.93 | 0.93 |
| R153T | 0.31 | 0.63 | 0.74 | 0.84 | 0.94 |
| R153V | 0.23 | 0.28 | 0.59 | 0.63 | 0.81 |
| R153W | 0.42 | 0.77 | 1.07 | 0.90 | 0.87 |
| R153Y | 0.32 | 0.60 | 0.73 | 0.84 | 0.90 |
| K157A | 0.68 | 1.04 | 0.93 | 1.01 | 0.91 |
| K157D | 0.69 | 0.96 | 1.01 | 1.12 | 0.90 |
| K157E | 0.10 | 0.92 | 0.75 | 1.03 | 0.73 |
| K157F | 0.40 | 1.01 | 0.94 | 1.07 | 0.95 |
| K157G | 0.50 | 0.98 | 0.76 | 1.04 | 0.93 |
| K157I | 0.71 | 1.00 | 0.81 | 1.05 | 0.94 |
| K157L | 0.18 | 0.88 | 0.60 | 1.04 | 0.75 |
| K157M | 0.33 | 0.99 | 0.77 | 0.99 | 0.88 |
| K157P | 0.11 | 0.57 | 0.63 | 3.04 | 1.86 |
| K157Q | 0.50 | 1.00 | 0.70 | 1.00 | 0.88 |
| K157T | 0.14 | 0.79 | 0.47 | 1.02 | 0.83 |
| K157V | 0.46 | 0.99 | 0.86 | 0.99 | 0.91 |
| K157W | 1.06 | 0.95 | 0.84 | 1.04 | 0.93 |
| K157Y | 0.77 | 0.98 | 0.92 | 1.00 | 0.84 |
| N161E | 0.76 | 1.03 | 1.07 | 1.12 | 1.12 |
| D189A | 0.29 | 0.77 | 0.73 | 0.79 | 0.69 |
| D189C | 0.38 | 0.89 | 0.82 | 0.90 | 0.76 |
| D189E | 0.44 | 0.98 | 0.84 | 0.94 | 0.89 |
| D189F | 0.39 | 0.82 | 0.64 | 0.94 | 0.99 |
| D189G | 0.27 | 0.87 | 0.86 | 0.88 | 0.71 |
| D189H | 0.39 | 0.91 | 0.52 | 0.91 | 0.83 |
| D189I | 0.16 | 0.52 | 0.39 | 0.63 | 0.61 |
| D189K | 0.37 | 0.96 | 0.78 | 0.89 | 0.73 |
| D189L | 0.33 | 1.04 | 0.82 | 0.89 | 0.85 |
| D189N | 0.55 | 0.95 | 1.05 | 1.00 | 0.96 |
| D189P | 0.12 | 0.30 | 0.22 | 0.72 | 0.76 |
| D189Q | 0.73 | 0.98 | 0.72 | 0.93 | 0.86 |
| D189R | 0.38 | 0.96 | 0.82 | 0.94 | 0.88 |
| D189S | 0.14 | 0.60 | 0.32 | 0.86 | 1.22 |
| D189T | 0.21 | 0.84 | 0.84 | 0.85 | 0.76 |
| D189V | 0.36 | 1.03 | 0.99 | 1.03 | 0.91 |
| D189W | 0.13 | 0.18 | 0.34 | 0.45 | 1.06 |
| D189Y | 0.32 | 0.52 | 0.46 | 1.30 | 1.34 |
| K194A | 0.30 | 0.67 | 0.86 | 0.95 | 1.00 |
| K194C | 0.22 | 1.08 | 1.72 | 0.88 | 0.88 |
| K194D | 0.61 | 0.98 | 1.07 | 1.00 | 1.03 |
| K194E | 0.44 | 1.00 | 1.14 | 1.02 | 1.14 |
| K194F | 0.67 | 1.03 | 0.94 | 1.04 | 1.13 |
| K194G | 0.43 | 0.92 | 0.65 | 0.92 | 0.96 |
| K194I | 0.24 | 0.38 | 0.49 | 0.50 | 0.59 |
| K194L | 0.61 | 0.98 | 0.90 | 1.01 | 1.22 |
| K194M | 0.61 | 1.02 | 0.86 | 1.03 | 1.17 |
| K194N | 0.54 | 0.99 | 1.02 | 1.04 | 1.17 |
| K194P | 0.32 | 0.39 | 0.55 | 0.46 | 0.38 |
| K194Q | 0.64 | 1.00 | 1.00 | 1.03 | 1.17 |
| K194S | 0.66 | 1.00 | 0.83 | 1.12 | 1.03 |
| K194T | 0.08 | 0.11 | 1.09 | 1.17 | 9.80 |
| K194V | 0.23 | 0.30 | 0.71 | 0.55 | 0.62 |
| K194W | 0.43 | 0.93 | 0.98 | 0.98 | 1.01 |
| K194Y | 0.08 | 0.11 | 0.36 | 0.60 | 2.65 |
| N197D | 1.50 | 1.12 | 1.08 | 1.06 | 1.07 |
| R203A | 0.71 | 0.93 | 0.75 | 0.69 | 0.88 |
| R203F | 0.85 | 0.92 | 0.99 | 0.67 | 0.87 |
| R203G | 0.60 | 1.07 | 1.13 | 0.66 | 1.39 |
| R203I | 0.39 | 0.70 | 0.64 | 1.46 | 3.02 |
| R203L | 0.46 | 1.14 | 0.54 | 1.08 | 1.24 |
| R203M | 0.58 | 0.88 | 0.91 | 0.99 | 1.25 |
| R203N | 0.36 | 1.08 | 0.82 | 1.06 | 1.20 |
| R203P | 0.29 | 0.49 | 0.28 | 2.85 | 4.58 |
| R203Q | 0.80 | 0.99 | 0.78 | 0.84 | 0.86 |
| R203S | 0.54 | 1.19 | 0.53 | 1.99 | 1.96 |
| R203T | 0.66 | 1.04 | 0.82 | 0.99 | 0.91 |
| R203V | 0.85 | 0.94 | 0.89 | 0.73 | 0.78 |
| R203W | 0.39 | 1.10 | 0.63 | 2.28 | 2.42 |
| R203Y | 0.57 | 1.09 | 1.03 | 1.03 | 1.18 |
| Q204D | 1.23 | 1.04 | 0.73 | 1.00 | 1.00 |
| Q204E | 1.08 | 1.12 | 1.05 | 0.93 | 1.04 |
| Q239D | 0.59 | 0.98 | 0.91 | 0.92 | 0.92 |
| Q239E | 0.70 | 1.10 | 1.16 | 1.00 | 1.04 |
| N247D | 1.18 | 0.76 | 0.67 | 0.58 | 0.96 |
| N254E | 0.20 | 0.84 | 0.56 | 0.76 | 0.91 |
| Q281D | 1.10 | 0.60 | 0.43 | 1.33 | 0.95 |
| Q281E | 2.50 | 0.89 | 0.85 | 1.10 | 0.63 |
| N285D | 0.35 | 0.70 | 0.59 | 1.99 | 2.24 |
| K288A | 0.41 | 0.61 | 0.68 | 1.52 | 2.84 |
| K288C | 0.41 | 0.95 | 0.63 | 0.72 | 1.49 |
| K288D | 0.23 | 0.23 | *0.05* | 5.77 | 5.10 |
| K288E | 0.38 | 0.89 | 0.81 | 0.65 | 1.60 |
| K288F | 0.36 | 0.75 | 0.29 | 1.53 | 2.74 |
| K288G | 0.23 | 0.40 | 0.12 | 2.22 | 4.09 |
| K288H | 0.32 | 0.90 | 0.48 | 1.09 | 1.54 |
| K288I | 0.40 | 0.75 | 0.37 | 1.51 | 2.48 |

TABLE 8-1-continued

Performance Indexes of CBH2 Charge Variants

| Variant | HPLC | PASC sp. ac. | PCS sp. ac. | Res EtOH | Res Heat |
|---|---|---|---|---|---|
| K288L | 0.80 | 0.96 | 0.81 | 0.60 | 0.82 |
| K288N | 0.71 | 0.98 | 0.84 | 1.08 | 1.68 |
| K288P | 0.26 | 0.34 | *0.05* | 5.00 | 5.39 |
| K288Q | 0.23 | 0.80 | 0.18 | 1.23 | 2.51 |
| K288S | 0.19 | 0.71 | 0.21 | 2.02 | 2.72 |
| K288T | 0.25 | 0.71 | 0.35 | 1.27 | 2.96 |
| K288V | 0.31 | 0.84 | 0.38 | 1.67 | 1.87 |
| N289D | 0.84 | 0.96 | 0.87 | 0.93 | 0.92 |
| N289E | 0.13 | 0.26 | 0.63 | 1.03 | 1.48 |
| R294A | 0.97 | 1.06 | 0.89 | 0.92 | 0.77 |
| R294C | 0.70 | 1.15 | 0.74 | 1.01 | 1.16 |
| R294D | 0.75 | 0.94 | 0.85 | 0.94 | 1.09 |
| R294E | 0.73 | 0.82 | 0.66 | 1.02 | 1.20 |
| R294F | 0.37 | 0.52 | 0.54 | 0.90 | 1.56 |
| R294G | 1.25 | 0.93 | 0.84 | 0.71 | 0.87 |
| R294I | 0.77 | 0.84 | 0.72 | 0.98 | 1.01 |
| R294L | 0.54 | 1.06 | 1.03 | 1.05 | 1.22 |
| R294M | 0.34 | 0.76 | 0.78 | 0.81 | 1.78 |
| R294N | 0.50 | 0.80 | 0.64 | 1.30 | 1.06 |
| R294P | 0.48 | 0.86 | 0.74 | 0.74 | 0.99 |
| R294Q | 0.50 | 0.79 | 0.75 | 1.23 | 1.30 |
| R294S | 0.64 | 1.00 | 0.57 | 1.32 | 1.47 |
| R294T | 1.12 | 1.03 | 0.97 | 1.02 | 1.10 |
| R294V | 0.83 | 0.96 | 0.83 | 0.82 | 1.03 |
| R294W | 1.08 | 1.01 | 0.57 | 0.56 | 0.58 |
| R294Y | 0.26 | 0.43 | 0.31 | 2.39 | 3.19 |
| K327A | 0.86 | 1.03 | 0.98 | 0.76 | 0.76 |
| K327C | 0.42 | 0.93 | 1.25 | 1.28 | 1.02 |
| K327D | 0.31 | 0.73 | 0.76 | 1.13 | 1.81 |
| K327E | 0.73 | 0.84 | 0.85 | 1.05 | 0.87 |
| K327F | 0.24 | 0.61 | 0.44 | 1.91 | 2.14 |
| K327G | 0.24 | 0.83 | 0.16 | 1.65 | 1.30 |
| K327I | 0.31 | 0.74 | 0.23 | 1.44 | 1.37 |
| K327L | 0.26 | 0.94 | 0.60 | 0.89 | 1.30 |
| K327M | 0.41 | 0.90 | 0.90 | 0.87 | 1.44 |
| K327N | 0.41 | 0.90 | 1.04 | 0.74 | 1.33 |
| K327P | 0.21 | 0.58 | *0.05* | 1.65 | 2.77 |
| K327Q | 1.32 | 1.06 | 1.42 | 1.15 | 0.77 |
| K327S | 0.20 | 0.63 | 0.58 | 2.39 | 2.92 |
| K327T | 0.21 | 0.29 | 0.09 | 3.69 | 7.57 |
| K327V | 0.28 | 0.86 | 0.58 | 0.66 | 1.26 |
| K327W | 0.28 | 1.05 | 0.74 | 0.93 | 1.57 |
| K327Y | 0.93 | 1.04 | 1.08 | 0.49 | 0.60 |
| N339D | 0.92 | 1.04 | 1.05 | 1.04 | 1.10 |
| N339E | 0.94 | 1.03 | 0.83 | 1.08 | 1.13 |
| N344D | 0.29 | 0.85 | 1.10 | 1.43 | 1.31 |
| K356A | 1.22 | 1.03 | 0.88 | 0.23 | 0.25 |
| K356C | 0.62 | 0.92 | 0.98 | 0.29 | 0.45 |
| K356D | 0.42 | 0.87 | 0.57 | 0.22 | 0.42 |
| K356E | 0.43 | 0.98 | 0.71 | 0.28 | 0.43 |
| K356F | 0.69 | 0.99 | 0.45 | 0.15 | 0.39 |
| K356G | 0.97 | 0.98 | 0.20 | 0.20 | 0.40 |
| K356I | 0.76 | 0.96 | 0.60 | 0.26 | 0.46 |
| K356L | 0.67 | 1.00 | 0.68 | 0.45 | 0.39 |
| K356M | 0.68 | 0.99 | 0.88 | 0.54 | 0.53 |
| K356N | 0.98 | 1.04 | 0.72 | 0.19 | 0.37 |
| K356P | 0.23 | 0.52 | 0.33 | 1.09 | 0.99 |
| K356Q | 0.77 | 0.99 | 0.77 | 0.41 | 0.43 |
| K356S | 0.58 | 0.88 | 0.48 | 0.22 | 0.41 |
| K356T | 0.63 | 1.00 | 0.49 | 0.28 | 0.43 |
| K356V | 0.91 | 0.90 | 0.75 | 0.35 | 0.31 |
| K356W | 0.39 | 0.90 | 0.42 | 0.24 | 0.47 |
| K356Y | 0.52 | 0.96 | 0.47 | 0.20 | 0.51 |
| R378A | 0.21 | 0.76 | 0.79 | 0.25 | 0.54 |
| R378C | 0.25 | 0.34 | 0.42 | 0.74 | 1.01 |
| R378D | 0.19 | 0.23 | 0.33 | 0.49 | 0.58 |
| R378E | 0.17 | 0.18 | 0.30 | 0.92 | 0.94 |
| R378F | 0.13 | 0.39 | 1.34 | 0.12 | 0.38 |
| R378G | 0.08 | 0.22 | 1.48 | 0.19 | 0.82 |
| R378I | 0.19 | 0.42 | 0.33 | 0.38 | 0.69 |
| R378L | 0.21 | 0.75 | 0.79 | 0.33 | 0.53 |
| R378M | 0.14 | 0.52 | 0.77 | 0.37 | 0.47 |
| R378N | 0.12 | 0.19 | 0.48 | 0.38 | 0.81 |
| R378P | 0.17 | 0.65 | 0.54 | 0.48 | 0.62 |
| R378Q | 0.20 | 0.82 | 0.94 | 0.56 | 0.59 |
| R378S | 0.18 | 0.65 | 0.47 | 0.45 | 0.64 |
| R378T | 0.18 | 0.52 | 1.03 | 0.25 | 0.43 |
| R378V | 0.36 | 1.01 | 0.98 | 1.06 | 1.19 |
| R378W | 0.09 | 0.10 | 0.64 | 0.34 | 0.30 |
| R378Y | 0.24 | 0.60 | 0.62 | 0.23 | 0.53 |
| N382D | 0.71 | 0.81 | N.D. | 1.17 | 1.15 |
| N382E | 2.21 | 0.16 | N.D. | 6.19 | 5.56 |
| D405A | 1.75 | 0.82 | 0.33 | 0.32 | 0.60 |
| D405C | 0.45 | 0.63 | 0.57 | 0.72 | 0.97 |
| D405E | 0.85 | 0.81 | 0.63 | 0.50 | 0.65 |
| D405F | 0.79 | 0.95 | 0.24 | 0.56 | 0.82 |
| D405G | 0.77 | 0.87 | 0.16 | 0.56 | 0.86 |
| D405H | 0.27 | 0.38 | 0.25 | 3.35 | 3.59 |
| D405I | 0.62 | 1.04 | 0.49 | 0.83 | 1.02 |
| D405K | 0.63 | 0.65 | 0.24 | 0.43 | 0.72 |
| D405L | 0.41 | 0.95 | 0.76 | 0.38 | 0.43 |
| D405M | 0.52 | 1.31 | 0.58 | 0.59 | 0.69 |
| D405N | 0.74 | 1.04 | 0.78 | 1.34 | 1.32 |
| D405P | 0.77 | 0.80 | 0.19 | 0.99 | 1.02 |
| D405Q | 0.71 | 1.12 | 0.39 | 1.10 | 1.21 |
| D405R | 0.93 | 1.20 | 0.36 | 0.56 | 0.61 |
| D405S | 0.95 | 1.24 | 0.40 | 0.75 | 0.96 |
| D405T | 0.74 | 1.17 | 0.32 | 0.64 | 0.83 |
| D405V | 0.39 | 1.05 | 0.60 | 1.32 | 1.24 |
| D405W | 1.12 | 1.17 | 0.40 | 0.42 | 0.48 |
| D405Y | 1.56 | 1.07 | 0.39 | 0.31 | 0.07 |

Example 9

Effect of Charge Change on the Activity of CBH2 Variants

In this example, the effect of charge change on the activity of CBH2 in a pretreated corn stover (PCS) assay of cellulase activity was assessed. Briefly, the number of PCS winners in the CBH2 SELs was determined as a property of net charge change. In Table 9-1, the ratio of observed to expected (o/e) winners was determined in the PCS assay. Values in bold italics are significantly different from the average of 10 random distributions plus or minus the number of standard deviations (sd) listed in the respective columns.

TABLE 9-1

Charge Effect on Activity of CBH2 Variants in a PCS Assay

| PCS Charge change | o/e 1 sd | o/e 2 sd | o/e 3 sd | Results |
|---|---|---|---|---|
| −2.00 | *1.20* | *1.20* | *1.20* | >90% confident more than expected |
| −1.00 | *1.40* | *1.40* | *1.40* | >99% confident more than expected |
| 0.00 | *1.03* | *1.03* | *1.03* | as expected |
| 1.00 | *0.46* | *0.46* | *0.46* | >95% confident less than expected |
| 2.00 | *0.00* | *0.00* | *0.00* | as expected |

As shown in Table 9-1 and FIG. 4, decreasing charge (e.g., −1, −2) results in a significantly higher frequency of CBH2 winners in the PCS assay, while increasing charge (e.g., +1) results in a significantly lower frequency of CBH2 winners in the PCS assay. In conclusion, CBH2 activity on PCS correlates with decrease in charge.

We claim:

1. A cellulase variant obtained from a parent cellulase, wherein said variant is a mature form having cellulase activity, comprises a sequence that is at least 95% identical to the amino acid sequence of SEQ ID NO:3, and comprises a substitution at position 203, wherein the positions are numbered by correspondence with the amino acid sequence of SEQ ID NO:3, and wherein the substitution causes the cellulase variant to have a more negative net charge in comparison to the parent cellulase.

2. The cellulase variant of claim 1, wherein the substitution at position 203 comprises removal of one or more positive charges.

3. The cellulase variant of claim 2, wherein the removal of one or more positive charges comprises a replacement of an arginine with a neutral amino acid.

4. The cellulase variant of claim 1, wherein the substitution at position 203 comprises addition of one or more negative charges.

5. The cellulase variant of claim 1, wherein the substitution at position 203 comprises removal of one or more positive charges and addition of one or more negative charges.

6. The cellulase variant of claim 5, wherein the removal of one or more positive charges and addition of one or more negative charges comprises a placement of an arginine with a negatively charged amino acid.

7. The cellulase variant of claim 1, wherein the variant comprises a further substitution at one or more further positions selected from the group consisting of 146, 151, 189, 208, 211, 244, 277 and 405, wherein the further positions are numbered by correspondence with the amino acid sequence of SEQ ID NO:3.

8. The cellulase variant of claim 7, wherein the further substitution at one or more further positions comprises a replacement of aspartic acid or glutamic acid with a neutral amino acid.

9. The cellulase variant of claim 7, wherein the further substitution at one or more further positions comprises one or more of the group consisting of D151N, D189N, D211N, D277N, D405N, E146Q, E208Q, and E244Q, wherein the positions are numbered by correspondence with the amino acid sequence of SEQ ID NO:3.

10. The cellulase variant of claim 1, wherein the parent cellulase is selected from the group consisting of *Hypocrea*

*jecorina* CBH2, *Hypocrea koningii* CBH2, *Humicola insolens* CBH2, *Acremonium cellulolyticus* CBH2, *Agaricus bisporus* CBH2, *Fusarium osysporum* EG, *Phanerochaete chrysosporium* CBH2, *Talaromyces emersonii* CBH2, *Thermobifida fusca* 6B/E3 CBH2, *Thermobifida fusca* 6A/E2 EG, and *Cellulomonas fimi* CenA EG.

11. The cellulase variant of claim 1, wherein the parent cellulase is at least 97% identical to a member of the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

12. The cellulase variant of claim 1, wherein the more negative net charge is a −1 or −2 in comparison to the parent cellulase.

13. A method of converting biomass to sugars comprising contacting said biomass with the cellulase variant of claim 1.

14. A method of producing a fuel comprising:
contacting a biomass composition with an enzymatic composition comprising the cellulase variant of claim 1 to yield a sugar solution; and
culturing the sugar solution with a fermentative microorganism under conditions sufficient to produce a fuel.

* * * * *